United States Patent [19]
Chang et al.

[11] Patent Number: 5,552,404
[45] Date of Patent: Sep. 3, 1996

[54] OPIOID COMPOUNDS AND METHODS FOR USING SAME

[75] Inventors: Kwen-Jen Chang, Chapell Hill; Dulce G. Bubacz, Cary; Ann O. Davis, Raleigh; Robert W. McNutt, Jr.; Michael J. Bishop, both of Durham, all of N.C.

[73] Assignee: Delta Pharmaceuticals, Inc., Chapel Hill, N.C.

[21] Appl. No.: 431,377

[22] Filed: Apr. 28, 1995

Related U.S. Application Data

[60] Division of Ser. No. 285,313, Aug. 3, 1994, which is a continuation-in-part of Ser. No. 169,879, Dec. 17, 1993, abandoned, which is a continuation-in-part of Ser. No. 98,333, Jul. 30, 1993, abandoned.

[51] Int. Cl.$^6$ .................. A61K 31/495; A61K 31/445
[52] U.S. Cl. ........................................... 514/255
[58] Field of Search ............................... 514/255

[56] References Cited

U.S. PATENT DOCUMENTS

| | | |
|---|---|---|
| 2,630,435 | 3/1953 | Baltzly et al. |
| 4,518,711 | 5/1985 | Hruby et al. |
| 4,816,586 | 3/1989 | Portoghese |

FOREIGN PATENT DOCUMENTS

| | | |
|---|---|---|
| 0133323A1 | 2/1985 | European Pat. Off. |
| 0287339A2 | 10/1988 | European Pat. Off. |
| 0458160A2 | 11/1991 | European Pat. Off. |
| 0506468A1 | 9/1992 | European Pat. Off. |
| 864522 | 12/1986 | South Africa |
| 90/15599 | 12/1990 | WIPO |
| PCT/US92/07754 | 2/1992 | WIPO |

OTHER PUBLICATIONS

Pakarinen, E. D., "Effects of Convulsant Agents on Learning and Memory in Squirrel Monkeys", Dissertation Abstracts International. 54(01B), 189 (Mar. 31, 1993—entered in the Louisiana State University online catalog).

Calderon, S. N., "Synthesis and Absolute Configuration of Optically Pure Enantiomers of (=)-BW373U86, A Nonpeptidic δ-Opioid Receptor Agonist", College on Problems of Drug Dependence, Inc., Fifty-fifth Annual Scientific Meeting. Toronto. Canada. Poster Presentation. (Jun. 12–17, 1993).

Selley, D. E., "BW373U86 A Non–peptide δ Opioid Agonist With Novel Receptor–G–Protein–Mediated Actions", Meeting of the International Narcotics Research Conference (INRC). Skoevde, Sweden, Abstract (Jul. 11–16, 1993).

Corner, S. D., "BW 373U86:Behavioral Pharmacology of a Putative Non–Peptide, Systemically–Active Delta Opiod Agonist", Disertation Abstracts International, 53(5B), 2578 (Jul. 1, 1992—entered in the University of Michigan online catalog).

Chang, K. –J., "Identification of a novel, potent and selective non–peptidic delta–selective agonist BW 373U86", Meeting of the International Narcotics Research Conference (INRC). Keystone, Colorado, Oral Presentation. (Jun. 23–27, 1992).

Comer, S. D., "BW 373U86: Delta–receptor–mediation of convulsions and refractoriness." Meeting of the International Narcotics Research Conference (INRC). Keystone, Colorado, Oral Presentation. (Jun. 23–27, 1992).

Dykstra, L., "Behavioral effects of a novel and selective opioid delta agonist in the monkey." Meeting of the International Narcotics Research Conference (INRC). Keystone. Colorado. Oral Presentation. (Jun. 23–27, 1992).

Porreca, F. "Multiple opioid delta receptors." Meeting of the International Narotics Research Conference (INRC). Keystone, Colorado. Oral Presentation. (Jun. 23–27).

Broadbent, J. et al., "Role of opioid receptor subtypes in the discriminative stimulus effects of cocaine." Meeting of the International Narcotics Research Conference (INRC), Keystone, Colorado. Abstract, (Jun. 23–27, 1992).

Dworkin, S. I. et al., "Effects of δ-opiate agonists and antagonists on cocaine and heroin self administration in rats." Meeting in the International Narcotics Research Conference (INRC). Keystone, Colorado, Abstract (Jun. 23–27, 1992).

Dykstra, L., et al. "Effects of a novel delta opioid agonist in squirrel monkeys responding under a schedule of shock tritration." Meeting of the International Narcotics Research Conference (INRC). Keystone, Colorado, Abstract (Jun. 23–27, 1992).

Lee, P. H. K., et al., "A non–peptide delta–opioid receptor agonist BW 373U86 suppresses naloxone–precipiated morphine abstience." Meeting of the International Narcotics Research Conference (INRC). Keystone, Colorado, Abstract (Jun. 23–27, 1992).

Porreca, F., et al., "Pharmacology of Multiple Opioid Delta Receptors", National Institute on Drug Abuse Research Monograph Series 132, Problems of Drug Dependence, 1992: Proceeding of the 54th Annual Scientific Meeting, 430–436 (1993).

Iwanoto, T. et a., "Calcium Antagonism by KB–2796, a New Diphenylpiperazine Analogue, in Dog Vascular Smooth Muscle", J. Pharm. Pharmacol., 43. 535–539 (1991).

(List continued on next page.)

Primary Examiner—Marianne M. Cintins
Assistant Examiner—Keith MacMillan
Attorney, Agent, or Firm—Steven J. Hultquist

[57] ABSTRACT

Diarylmethyl piperazine compounds having utility as exogenous receptor combinant species for binding with receptors such as delta, mu, sigma, and/or kappa receptors are disclosed. Compounds of the invention may be employed as conjugates in agonist/antagonist pairs for transductional monitoring and assays of neurotransmitter function, and also variously exhibit therapeutic utility, including mediating analgesia, and possessing utility for the treatment of diarrhea, urinary incontinence, mental illness, drug and alcohol addiction/overdose, lung edema, depression, asthma, emphysema, cough, and apnea, respiratory depression, cognitive disorders, emesis and gastrointestinal disorders.

20 Claims, No Drawings

OTHER PUBLICATIONS

Goenechea, V. S. et al., "Untersuchungen zur Biotransformation von Meclozin im menschlichen Köper", J. Clin. Chem. Clin. Biochem., 26. 105–115 (1988)—See Specification. p. 4, last paragraph and *Chemical Abstracts* 108: 215746g.

Iwamoto, T. et al., "Effects of KB–2796, a New Calcium Antagonist, and Other Diphenlpiperazines on [$^3$H]Nitrendipine Binding", Japan. J. Pharmacol., 48. 241–247 (1988).

Natsuka, K. et al., "Synthesis and Structure–Activity Relationships of 1–Substituted 4–(1,2–Diphenylethyl)piperazine Derivatives Having Narcotic Agonist and Antagonist Activity". J. Med. Chem., 30(10), 1779–1787 (1987).

Meuldermans, W. et al., "Plasma Levels, Biotransformation and Excretion of Oxatomide (R 35 443) in Rats, Dogs and Man", Xenobiotica. 14(6), 445–462 (1984).

Krishnamurthy, S., "A Highly Efficient and General N–Monomethylation of Functionalized Primary Amines Via Formylation—Borane: Methyl Sulfide Reduction". Tetrahedron Letters. 23(33), 3315–3318, (1982).

Lord. J. A. H. et al., "Endogenous Opioid Peptides: Multiple Agonists and Receptors", Nature. 267, 495–499 (1977).

Chang et al., "A Novel, Potent and Selective Nonpeptide *Delta* Opioid Receptor Agonist BW 373U86", J. Pharmacol. Exp. Ther., 267, 852–857 (1993).

Childers et al., "BW373U86: A Non–peptidic δ–Opioid Agonist With Novel Receptor–g Protein–mediated Actions in Rats Brain Membrane and Neuroblastoma Cells", Molec. Pharmacol., 44, 827–834 (1993).

Comer et al., "Convulsive Effects of Systemic Administration of the *Delta* Opioid Agonist BW373U86 in Mice", J. Pharmacol. Exp. Ther., 267, 888–895 (1993).

Comer et al., "Discriminative Stimulus Effects of BW373U86: A Non–peptide Ligand With Selectivity for *Delta* Opioid Receptors". J. Pharmacol. Exp. Ther., 267, 866–874 (1993).

Dykstra et al., "A Novel *Delta* Opioid Agonist, BW373U86, in Squirrel Monkeys Responding Under a Schedule of Shock Titration", J. Pharmacol. Exp. Ther., 267, 875–882 (1993).

Lee et al., "A Nonpeptidic Delta–opioid Receptor Agonist. BW373U86, Attenuates the Development and Expression of Morphine Abstinence Precipitated by Naloxone in Rat . . .". J. Pharmacol. Exp. Ther., 267, 883–887 (1993).

Negus et al., "Effects of Opioid Agonist Selective for *Mu, Kappa and Delta* Opioid Receptors on Schedule–controlled Responding in Rhesus Monkeys: Antagonism by Quadazocine", J. Pharmacol. Exp. Ther., 267, 896–903 (1993).

Wild et al., "Binding of 373U86, A Non–peptidic δ–Opioid Receptor Agonist is Not Regulated by Guanine Nucleotides and Sodium", Eur. J. Pharmacol.—Molec. Pharmacol., Section 246, 289–292 (1993).

Wild et al., "Antinociceptive Actions of BW373U86 in the Mouse", J. Pharmacol, Exp. Ther. 267, 858–865, 1993.

Xu et al., "Differential Binding of Opioid Peptides and Other Drugs to Two Subtypes of Opioid $δ_{ncx}$ Binding Sites in Mouse Brian: Further Evidence of δ Receptor Heterogeneity", Peptides 14, 893–907 (1993).

"A General Route to 4–Substituted Imidazoles", J. Chem. Soc., Perkin Trans. I, 1989, pp. 1139–1145.

"The Synthesis of Secondary and Tertiary Amines by Borohydride Reduction", Department of Chemistry, Harvard University, Cambridge, Mass., Nov. 1963, pp. 3259–61.

"Diastereoselektive Synthese neuartiger Mannich–Basen[1]) mittels Titanderivaten[2])", Helvetica Chimica Acta, vol. 67 (1984), pp. 1593–1597.

"Copper Salts Catalysis of N–Phenylation of Amines by Trivalent Organobismuth Compounds", Tetrahedron Letters, vol. 28, No. 8, pp. 887–890, 1987.

"Organic Chemistry of L–Tyrosine. 1. General Synthesis of Chiral Piperazines from Amino Acids", J. Org. Chem., 1985, 50, 4909–4913.

"Synthesis of Primary Amines via Alkylation of the Sodium Salt of Trifluoroacetamide: An Alternative to the Gabriel Synthesis", Communications, Department of Chemistry, University of Lancaster, Lancaster, Great Britain, pp. 941–944, 1985.

Review: "Iontophoretic Devices for Drug Delivery", Pharmaceutical Reserach, vol. 3, No. 6, 1986, pp. 318–326.

OPIOID COMPOUNDS AND METHODS FOR USING SAME

This is a Divisional of application Ser. No. 08/285,313 filed Aug. 3, 1994, which in turn is a Continuation-in-Part of application Ser. No. 08/169,879 filed Dec. 17, 1993, now abandoned which in turn is a Continuation-in-Part of application Ser. No. 08/098,333 filed Jul. 30, 1993, now abandoned which in turn is a Continuation-in-Part of International Patent Application No. PCT/GB93/00216, filed Feb. 2, 1993, now published as WO93/15062, and designating therein the United States as a Designated State.

BACKGROUND OF THE INVENTION

1. Field of the Invention

This invention relates generally to diarylmethyl piperazine compounds having utility in medical therapy especially as receptor-binding species, e.g., as conjugates in agonist/antagonist pairs for verifying/assaying receptor and neurotransmitter function. The compounds of the invention are useful as opioid receptor compounds having utility in treatment of pain, combatting drug addiction, alcohol addiction, drug overdose, mental illness, urinary incontinence, cough, lung edema, emesis, diarrhea, depression, and cognitive, respiratory, and gastro-intestinal disorders. The invention also relates to pharmaceutical formulations of such compounds, methods of treating certain disorders with such compounds, and processes by which such compounds may be prepared.

2. Description of the Related Art

In the study of opioid biochemistry, a variety of endogenous opioid compounds and non-endogenous opioid compounds has been identified. In this effort, significant research has been focused on understanding the mechanism of opioid drug action, particularly as it relates to cellular and differentiated tissue opiate receptors.

Opioid drugs typically are classified by their binding selectivity in respect of the cellular and differentiated tissue receptors to which a specific drug species binds as a ligand. These receptors include mu ($\mu$), delta ($\delta$), sigma ($\sigma$) and kappa ($\kappa$)receptors.

The well-known narcotic opiates, such as morphine and its analogs, are selective for the opiate mu receptor. Mu receptors mediate analgesia, respiratory depression, and inhibition of gastrointestinal transit. Kappa receptors mediate analgesia and sedation. Sigma receptors mediate various biological activities.

The existence of the opioid delta receptor is a relatively recent discovery which followed the isolation and characterization of endogenous enkephalin peptides which are ligands for the delta receptor. Research in the past decade has produced significant information about the delta receptor, but a clear picture of its function has not yet emerged. Delta receptors mediate analgesia, but do not appear to inhibit intestinal transit in the manner characteristic of mu receptors.

Opioid agents frequently are characterized as either agonists or antagonists. Agonists and antagonists are agents which recognize and bind to receptors, affecting (either initiating or blocking) biochemical/physiological sequences, a process known as transduction. Agonists inhibit or suppress neurotransmitter outputs in tissues containing receptors, e.g., inhibiting pain responses, or affecting other output-related phenomena. Antagonists also bind to receptors, but do not inhibit neurotransmitter outputs. Thus, antagonists bind to the receptor sites and block the binding of agonist species which are selective for the same receptor.

Concerning specific receptor ligands, the distinction between delta receptor agonists and antagonists heretofore has been made by their activity in the electrically stimulated mouse vas deferens assay, which typically has been considered the appropriate diagnostic tissue for the delta receptor. By contrast, mu receptor agonists are generally characterized by their activity in the electrically stimulated guinea pig ileum assay.

Only a relatively small number of essentially pure delta receptor-selective agents is known, and with the exception of the delta opioid receptor antagonists disclosed in Portoghese U.S. Pat. No. 4,816,586, all known delta receptor-selective opioid compounds are peptides, including endogenous enkephalins and other endorphins, as well as exogenous peptide analogs. The previously synthesized exogenous peptide analogs have various associated disadvantages in terms of their stability, their potentially suitable delivery routes as administered drug agents, and their in vivo tissue distribution.

Various physiological effects of the known peptide-based opioid ligands have been studied, including: analgesia; respiratory depression; gastrointestinal effects; mental, emotional, and cognitive process function; and mediation/modulation of other physiological processes.

The aforementioned U.S. Pat. No. 4,816,586, issued Mar. 28, 1989 to P. S. Portoghese, discloses various delta-opioid receptor antagonists of specified formula. The disclosed antagonist compounds are formed by fusion of an indole, benzofuran, benzopyrazine, or quinoline ring system, to the C-ring of naltrexone. These compounds are described as possessing a unique opioid receptor antagonist profile, including compounds which are highly selective for the delta opioid receptor.

U.S. Pat. No. 4,518,711 issued May 21, 1985 to V. J. Hruby et al. describes cyclic, conformationally constrained analogs of enkephalins. These compounds include both agonists and antagonists for the delta receptor.

In addition to the above-described references relating to opioid compounds, the art relevant to the compounds of the present invention includes the polyaryl piperazine compounds described in the various references identified below.

S. Goenechea, et al., in "Investigation of the Biotransformation of Meclozine in the Human Body," *J. Clin. Chem. Clin. Biochem.*, 1988 26(2), 105–15, describe the oral administration of a polyaryl piperazine compound in a study of meclozine metabolization in human subjects.

In "Plasma Levels, Biotransformation and Excretion of Oxatomide in Rats, Dogs, and Man," Meuldermans, W., et al., *Xenobiotica*, 1984, 15(6), 445–62, there is disclosed a metabolic study of plasma levels, biotransformation, and excretion of oxatomide.

T. Iwamoto, et al., in "Effects of KB-2796, A New Calcium Antagonist, and Other Diphenylpiperazines on [$^3$H] nitrendipine Binding," *Jpn. J. Pharmacol.*, 1988, 48(2), 241–7, describes the effect of a polyaryl piperazine of specified formula, as a calcium antagonist.

K. Natsuka, et al., in "Synthesis and Structure-Activity Relationships of 1-Substituted 4-(1,2-Diphenylethyl)piperazine Derivatives Having Narcotic Agonist and Antagonist Activity," *J. Med. Chem.*, 1987, 30 (10), 1779–1787, disclose racemates and enantiomers of 1-substituted 4-[2-(3-hydroxyphenyl)-1-phenylethyl]piperazine derivatives.

European Patent Application No. 458,160 published 27 Nov. 1991 describes substituted diphenylmethane derivatives which are said to be useful as analgesic and antiinflammatory agents, including compounds wherein the methylene bridging group (linking the two phenyl moieties) may have as a substituent on the methylene carbon a piperidinyl or piperazinyl group.

South African Patent Application No. 8604522 published 17 Dec. 1986 discloses N-substituted arylalkyl and arylalkylene substituted amino-heterocylic compounds, including piperidine derivatives, which are described as useful cardiovascular, antihistamine, and anti-secretory agents.

European Patent Application No. 133,323 published 20 Feb. 1985 discloses certain diphenylmethyl piperazine compounds useful as non-sedative antihistamines.

There is a continuing need in the art for improved opioid compounds, particularly compounds which are free of adverse side effects of conventional opiates such as morphine and pethidine.

SUMMARY OF THE INVENTION

The present invention relates to diarylmethyl piperazine compounds of the formula:

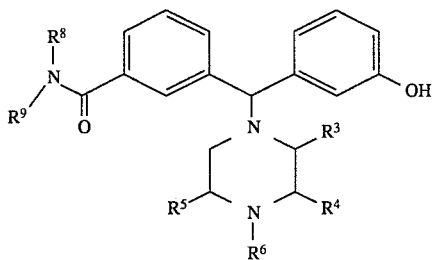

wherein:

$R^8$ and $R^9$ may be the same or different, and may be hydrogen, $C_1$–$C_6$ alkyl, $C_3$–$C_6$ cycloalkyl, $C_5$–$C_{10}$ aryl, or $C_5$–$C_{10}$ alkyl, or $R^8$ and $R^9$ together may form a ring of 5 or 6 atoms;

$R^3$, $R^4$, $R^5$=hydrogen or methyl, where the total number of methyl groups is one or two; and $R^6$=hydrogen, $C_1$–$C_6$ alkyl, $C_2$–$C_6$ methoxyalkyl, or $C_3$–$C_6$ cycloalkyl, or a pharmaceutically acceptable ether, ester, salt, or other physiologically functional derivative thereof.

The compounds of the invention have opioid receptor binding activity and have utility in medical therapy, in particular for the treatment of pain.

DETAILED DESCRIPTION OF THE INVENTION, AND PREFERRED EMBODIMENTS THEREOF

As used herein, in reference to the present invention, the term "alkyl" is intended to be broadly construed as encompassing: (i) alkyl groups of straight-chain as well as branched chain character; (ii) unsubstituted as well as substituted alkyl groups, wherein the substituents of substituted alkyl groups may include any sterically acceptable substituents which are compatible with such alkyl groups and which do not preclude the efficacy of the diarylmethyl piperazine compound for its intended utility (examples of substituents for substituted alkyl groups include halogen (e.g., fluoro, chloro, bromo, and iodo), amino, amido, $C_1$–$C_4$ alkyl, $C_1$–$C_4$ alkoxy, nitro, hydroxy, etc.); (iii) saturated alkyl groups as well as unsaturated alkyl groups, the latter including groups such as alkenyl-substituted alkyl groups (e.g., ally, methallyl, propallyl, butenylmethyl, etc.), alkynyl-substituted alkyl groups, and any other alkyl groups containing sterically acceptable unsaturation which is compatible with such alkyl groups and which does not preclude the efficacy of the diarylmethyl piperazine compound for its intended utility; and (iv) alkyl groups including linking or bridge moieties, e.g., heteroatoms such as nitrogen, oxygen, sulfur, etc.

As used herein, in reference to the present invention, the term "aryl" is intended to be broadly construed as referring to carbocyclic (e.g., phenyl, naphthyl) as well as heterocyclic aromatic groups (e.g., pyridyl, thienyl, furanyl, etc.) and encompassing unsubstituted as well as substituted aryl groups, wherein the substituents of substituted aryl groups may include any sterically acceptable substituents which are compatible with such aryl groups and which do not preclude the efficacy of the diarylmethyl piperazine compound for its intended utility. Examples of substituents for substituted aryl groups include one or more of halogen (e.g., fluoro, chloro, bromo, and iodo), amino, amido, $C_1$–$C_4$ alkyl, $C_1$–$C_4$ alkoxy, nitro, trifluoromethyl, hydroxy, hydroxyalkyl containing a $C_1$–$C_4$ alkyl moiety, etc.

By "physiologically functional derivative" is meant a pharmaceutically acceptable salt, ether, ester or salt of an ether or ester of the compound of formula (I) or any other compound which, upon administration to the recipient, is capable of providing (directly or indirectly) the said compound of formula (I) or an active metabolite or residue thereof. Phenolic $C_1$–$C_6$ alkyl ethers are a sub-class of physiologically functional derivatives of the compounds of formula (I).

In enantiomeric forms, compounds of the invention include individual enantiomers of the compounds of formula (I) in single species form substantially free of the corresponding enantiomer, as well as in admixture (in mixtures of enantiomeric pairs and/or in mixtures of multiple enantiomer species).

A sub-class of compounds within the scope of formula (I) are the pharmaceutically acceptable esters and salts thereof.

Examples of pharmaceutically acceptable esters of the invention include carboxylic acid esters of hydroxy groups in compounds of formula (I) in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl)aminocarbonyl); and inorganic esters (e.g. mono-, di- or triphosphate).

Examples of pharmaceutically acceptable salts of the compounds of formula (I) and physiologically functional derivatives thereof include salts derived from an appropriate base, such as an alkali metal (for example, sodium, potassium), an alkaline earth metal (for example, calcium, magnesium), ammonium and $NX_4^+$ (wherein X is $C_1$–$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxy group consist of the anion of said compound in combination with a suitable cation such as $Na^+$, $NH_4^+$, or $NX_4^+$ (wherein X is for example a $C_{1-4}$ alkyl group).

For therapeutic use, salts of compounds of formula (I) will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived from a pharmaceutically acceptable acid or base, are within the scope of the present invention.

A sub-class of compounds within the scope of formula (I) are compounds wherein $R^6$ is $C_1-C_6$ alkyl or $C_3-C_6$ cycloalkyl.

A sub-class of compounds within the scope of formula (I) are compounds wherein $R^3$ and $R^5$ are both methyl and $R^4$ is hydrogen.

A sub-class of compounds within the scope of formula (I) are compounds wherein one of $R^8$ and $R^9$ is phenyl optionally substituted with one or more substituents selected from the group consisting of halogen, $C_1-C_3$ alkoxy and trifluoromethyl.

Preferably, halogen is chloro or fluoro and $C_1-C_3$ alkoxy is methoxy.

A preferred sub-class of compounds of the above formula (I) include those in which the moiety $NR^8R^9$ is selected from the group consisting of:

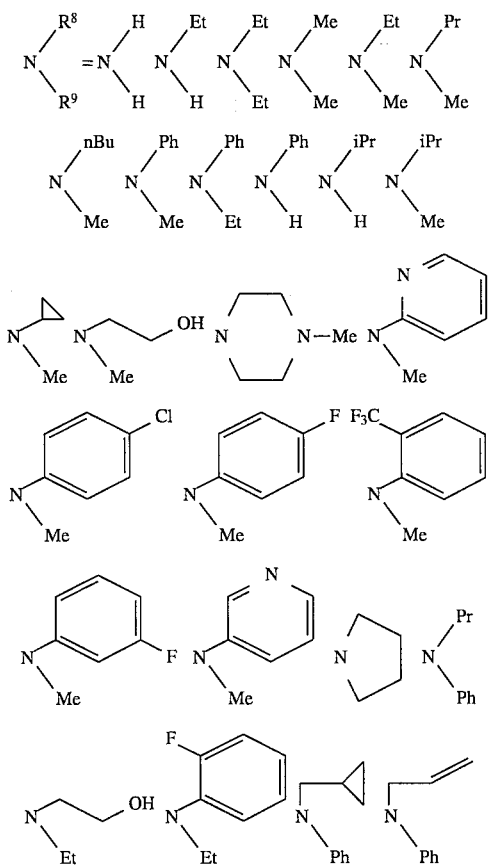

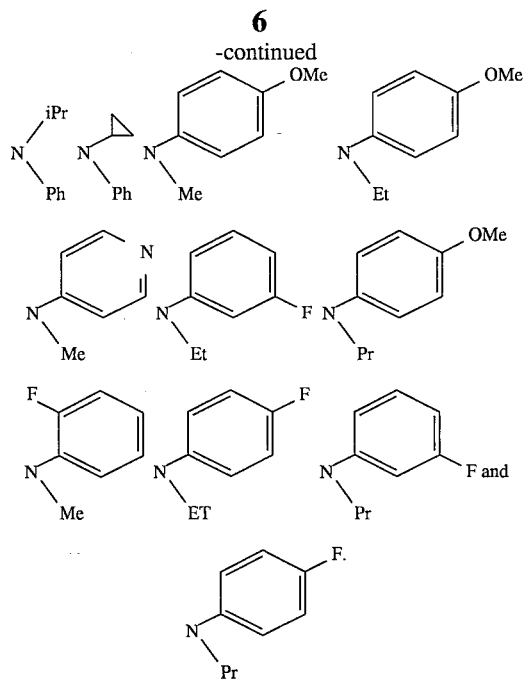

Another preferred sub-class of compounds within the scope of the present invention comprises compounds of the formula:

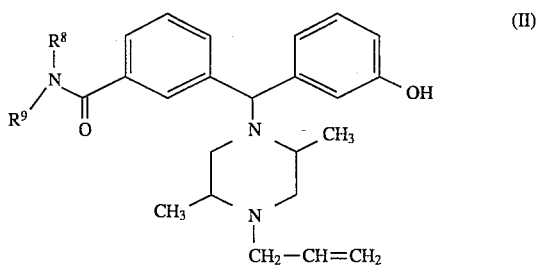

wherein:
$R^8$ and $R^9$ may be the same or different, and may be hydrogen, $C_1-C_6$ alkyl, $C_3-C_6$ cycloalkyl, $C_5-C_{10}$ aryl, or $R^8$ and $R^9$ together may form a ring of 5 or 6 atoms, or a pharmaceutically acceptable ether, ester, salt, or other physiologically functional derivative thereof.

A further preferred sub-class of compounds within the scope of the present invention comprises compounds of formula (II) wherein one of $R^8$ and $R^9$ is phenyl optionally substituted with one or more substituents selected from the group consisting of halogen, $C_1-C_3$ alkoxy, $C_1-C_3$ alkyl and trifluoromethyl, and the other of $R^8$ and $R^9$ is hydrogen or saturated $C_1-C_6$ hydrocarbyl or unsaturated $C_3-C_6$ hydrocarbyl,
or a pharmaceutically acceptable ether, ester, salt, or other physiologically functional derivative thereof.

As used herein, in reference to the present invention, the term "hydrocarbyl" is intended to encompass a group containing only carbon and hydrogen atoms which may contain double or triple bonds and which may be cyclic or aromatic in nature.

Illustrative compounds of the invention include the compounds identified below.

(+)-3-((αR)-α-((2S,5R)-4-Allyl-2,5-dimethyl-1-piperazinyl)-3-hydroxybenzyl)-N-(4-fluorophenyl)-N-methylbenzamide (+)-3-((αR)-α-((2S,5R)-4-Allyl-2,5-dimethyl-1-piperazinyl)-3-hydroxybenzyl)-N-methyl-N-phenylbenzamide (+)-3-((αR)-α-((2S,5R)-4-Allyl-2,5-dimethyl-1-piperazinyl)-3-hydroxybenzyl)-N,N-diethylbenzamide (+)-3-((αR)-α-((2S,5R)-4-Allyl-2,5-dimethyl-1-piperazinyl)-3-hydroxybenzyl)-N-(4-chlorophenyl)-N-methylbenzamide (+)-3-((αR)-α-((2S,5R)-4-Allyl-2,5-dimethyl-1-piperazinyl)-3-hydroxybenzyl)-N-ethyl-N-phenylbenzamide (+)-3-((αR)-α-((2S,5R)-4-Allyl-2,5-dimethyl-1-piperazinyl)-3-hydroxybenzyl)-N-methyl-N-(2-pyridyl)benzamide (−)-3-((αR)-α-((2S,5R)-4-Allyl-2,5-dimethyl-1-piperazinyl)-3-hydroxybenzyl)-N-phenylbenzamide 3-((αR)-α-(2S,5R)-4-Allyl-2,5-dimethyl-1-piperazinyl)-3-hydroxybenzyl)-N-methyl-N-(2-(trifluoromethyl)phenyl)-benzamide 3-((αR)-α-((2S,5R)-4-Allyl-2,5-dimethyl-1-piperazinyl)-3-hydroxybenzyl)-N-methyl-N-(2,4,6-trichlorophenyl)benzamide 3-((αR)-α-((2S,5R)-4-Allyl-2,5-dimethyl-1-piperazinyl)-3-hydroxybenzyl)-N-methyl-N-(4-pyridyl)benzamide 3-((αR)-α-((2S,5R)-4-Allyl-2,5-dimethyl-1-piperazinyl)-3-hydroxybenzyl)-N-methyl-N-(3-pyridyl)benzamide (+)-3-((αR)-α-((2S,5R)-4-Allyl-2,5-dimethyl-1-piperazinyl)-3-hydroxybenzyl)-N-benzyl-N-methylbenzamide (±)-cis-3-(α-(4-Allyl-3,5-dimethyl-1-piperazinyl)-3-hydroxybenzyl)-N,N-diethylbenzamide 3-((αR or αS)-α-((2S,5S)-4-Allyl-2,5-dimethyl-1-piperazinyl)-3-hydroxybenzyl)-N,N-diethylbenzamide 3-((αR or αS)-α-((2R,5R)-4-Allyl-2,5-dimethyl-1-piperazinyl)-3-hydroxybenzyl)-N,N-diethylbenzamide (+)-3-((αR)-α-((2S,5R)-4-Allyl-2,5-dimethyl-1-piperazinyl)-3-hydroxybenzyl)-N-methyl-N-phenethylbenzamide 3-((αR)-α-((2S,5R)-4-Allyl-2,5-dimethyl-1-piperazinyl)-3-hydroxybenzyl)-N-isopropyl-N-methylbenzamide (−)-3-((αR)-α-((2S,5R)-4-(Cyclopropylmethyl)-2,5-dimethyl-1-piperazinyl)-3-hydroxybenzyl)-N,N-diethylbenzamide (+)-3-((αR)-α-((2S,5R)-2,5-Dimethyl-1-piperazinyl)-3-hydroxybenzyl)-N,N-diethylbenzamide (+)-3-((αR)-α-((2S,5R)-2,5-Dimethyl-4-ethyl-1-piperazinyl)-3-hydroxybenzyl)-N,N-diethylbenzamide (−)-3-((αR)-α-((2S,5R)-2,5-Dimethyl-4-(2-propynyl)-1-piperazinyl)-3-hydroxybenzyl)-N,N-diethylbenzamide (±)-3-((αR*)-α-((2S*,5R*)-2,5-Dimethyl-4-propyl-1-piperazinyl)-3-hydroxybenzyl)-N,N-diethylbenzamide (+)-3-((αR)-α-((2S,5R)-2,4,5-Trimethyl-1-piperazinyl)-3-hydroxybenzyl)-N,N-diethylbenzamide (+)-3-((αR)-α-((2S,5R)-4-Allyl-2,5-dimethyl-1-piperazinyl)-3-hydroxybenzyl)-N-(3-fluorophenyl)-N-methylbenzamide (+)-3-((αR)-α-((2S,5R)-4-Allyl-2,5-dimethyl-1-piperazinyl)-3-hydroxybenzyl)-N-phenyl-N-propylbenzamide (+)-3-((αR)-α-((2S,5R)-4-Allyl-2,5-dimethyl-1-piperazinyl)-3-hydroxybenzyl)-N-(4-methoxyphenyl)-N-methylbenzamide (+)-3-((αR)-α-((2S,5R)-4-Allyl-2,5-dimethyl-1-piperazinyl)-3-hydroxybenzyl)-N-(2-fluorophenyl)-N-methylbenzamide (+)-3-((αR)-α-((2S,5R)-4-Allyl-2,5-dimethyl-1-piperazinyl)-3-hydroxybenzyl)-N-ethyl-N-(4-fluorophenyl)benzamide (+)-3-((αR)-α-((2S,5R)-4-Allyl-2,5-dimethyl-1-piperazinyl)-3-hydroxybenzyl)-N-allyl-N-phenylbenzamide (+)-3-((αR)-α-((2S,5R)-4-Allyl-2,5-dimethyl-1-piperazinyl)-3-hydroxybenzyl)-N-(cyclopropyl)methyl-N-phenylbenzamide 3-((αR)-α-((2S,5R)-4-Allyl-2,5-dimethyl-1-piperazinyl)-3-hydroxybenzyl)-N-isopropyl-N-phenylbenzamide 3-((αR)-α-((2S,5R)-4-Allyl-2,5-dimethyl-1-piperazinyl)-3-hydroxybenzyl)-N-cyclopropyl-N-phenylbenzamide 3-((αR)-α-((2S,5R)-4-Allyl-2,5-dimethyl-1-piperazinyl)-3-hydroxybenzyl)-N-(3-fluorophenyl)-N-propylbenzamide 3-((αR)-α-((2S,5R)-4-Allyl-2,5-dimethyl-1-piperazinyl)-3-hydroxybenzyl)-N-ethyl-N-(3-fluorophenyl)benzamide 3-((αR)-α-((2S,5R)-4-Allyl-2,5-dimethyl-1-piperazinyl)-3-hydroxybenzyl)-N-(2-fluorophenyl)-N-propylbenzamide 3-((αR)-α-((2S,5R)-4-Allyl-2,5-dimethyl-1-piperazinyl)-3-hydroxybenzyl)-N-ethyl-N-(2-fluorophenyl)benzamide 3-((αR)-α-((2S,5R)-4-Allyl-2,5-dimethyl-1-piperazinyl)-3-hydroxybenzyl)-N-(4-methoxyphenyl)-N-propylbenzamide 3-((αR)-α-((2S,5R)-4-Allyl-2,5-dimethyl-1-piperazinyl)-3-hydroxybenzyl)-N-ethyl-N-(4-methoxyphenyl)benzamide (+)-3-((αS)-α-((2S,5R)-4-Allyl-2,5-dimethyl-1-piperazinyl)-3-hydroxybenzyl)-N-methyl-N-phenylbenzamide (+)-3-((αR)-((2S,5R)-4-Allyl-2,5dimethyl-1-piperazinyl))-3-methoxybenzyl)-N-(3-fluorophenyl)-N-methylbenzamide (+)-3-((αR)-((2S,5R)-4-Allyl-2,5-dimethyl-1-piperazinyl)-3-methoxybenzyl)-N-ethyl-N-(4-fluorophenyl)benzamide 3-((R)-((2S,5R)-4-Allyl-2,5-dimethyl-1-piperazinyl)-3-(N-(3-fluorophenyl)-N-methylcarbamoyl)benzyl)phenyl monophosphate, and pharmaceutically acceptable salts thereof.

Compounds of the above general formula (I) exhibit binding selectivity for receptor(s). Depending on the structure and stereo-specificity of the particular formula (I) compounds, such compounds may exhibit binding ability to receptor(s) selected from the group consisting of delta receptors, mu receptors, kappa receptors, sigma receptors, and combinations of such receptors.

Various compounds within general formula (I) exhibit delta receptor agonist activity including mediating analgesia. Other compounds of such general formula exhibit delta receptor antagonist activity, as hereinafter more fully described. Still other compounds within the general formula exhibit mu receptor activity, and more particularly, in some instances, mixed mu receptor/delta receptor activity.

Compounds of the above general formula (I) and the illustrative compounds listed in the preceding paragraph have utility as exogenous receptor combinant compounds, i.e., compounds useful for binding with an opioid receptor. The combinant compound may be a conjugate in an agonist/antagonist pair which may be employed for transductional assay of neurotransmitter function in appertaining cellular or differentiated tissue systems. In addition to receptor assay, differential binding, and specificity applications for cellular, histological, and corporeal monitoring and assessment purposes, the compounds of the above general formula (I) variously exhibit specific bioactivity characteristics rendering them useful as treatment agents for various physiological and pathological conditions.

The compounds of the above general formula (I) include agonist species useful for the treatment of pain, diarrhea, depression, urinary incontinence, mental illness, cough, lung edema, respiratory depression, gastrointestinal disorders, spinal injury, and drug addiction.

The compounds of the above general formula (I) also include antagonist species which as mentioned are useful as agonist conjugates for neurotransmitter assay applications as well as antagonist species with utility for treatment of emesis, alcohol abuse, and drug overdose of opiate or other agonist species.

In addition, to the extent that degeneration or dysfunction of opioid receptors is present or implicated in a disease state involving tissue or discrete cellular loci, isotopically labeled versions of opioid compounds of the present invention find utility in diagnostic and imaging applications, e.g., diagnostic techniques involving positron emission tomography (PET) scans of the brain.

As mentioned hereinabove, opioid receptor sites are loci on cells which recognize and bind opiate and opioid drugs, which in turn can affect (initiate/block) biochemical/physiological sequences (transduction).

In the case of the non-peptide opioid agents contemplated by the present invention, the structure/activity pattern for the various compounds within the general formula (I) is highly diverse, and subtle differences such as changes in stereochemistry can result in different transductional effects. Thus, formula (I) comprehends agonist species as well as antagonist species.

In the case of delta receptor agonists, activity is generally distinguished and measured by activity in the electrically stimulated mouse vas deferens assay. Further, empirical determinations utilizing compounds of the present invention provide strong evidence of the existence of a delta receptor subtype in the brain that is different from the delta receptor in the mouse vas deferens.

In consequence of the existence of such delta receptor subtypes, other receptor binding assays or screening techniques, e.g., analgesia screening tests, may be employed as a further predictor of agonist or antagonist activity for specific compounds of the present invention.

In the case of mu receptor agonists, activity is generally distinguished and measured by activity in the electrically stimulated guinea pig ileum assay.

Particular preferred compounds from the above-listed illustrative compounds of the invention include (+)-3-(($\alpha$R)-$\alpha$-((2S,5R)-4-Allyl-2,5-dimethyl-1-piperazinyl)-3-hydroxybenzyl)-N-(4-fluorophenyl)-N-methylbenzamide (+)-3-(($\alpha$R)-$\alpha$-((2S,5R)-4-Allyl-2,5-dimethyl-1-piperazinyl)-3-hydroxybenzyl)-N-methyl-N-phenylbenzamide (+)-3-(($\alpha$R)-$\alpha$-((2S,5R)-4-Allyl-2,5-dimethyl-1-piperazinyl)-3-hydroxybenzyl)-N,N-diethylbenzamide (+)-3-(($\alpha$R)-$\alpha$-((2S,5R)-4-Allyl-2,5-dimethyl-1-piperazinyl)-3-hydroxybenzyl)-N-ethyl-N-phenylbenzamide (+)-3-(($\alpha$R)-$\alpha$-((2S,5R)-4-Allyl-2,5-dimethyl-1-piperazinyl)-3-hydroxybenzyl)-N-phenyl-N-propylbenzamide (+)-3-(($\alpha$R)-$\alpha$-((2S,5R)-4-Allyl-2,5-dimethyl-1-piperazinyl)-3-hydroxybenzyl)-N-(4-methoxyphenyl)-N-methylbenzamide (+)-3-(($\alpha$R)-$\alpha$-((2S,5R)-4-Allyl-2,5-dimethyl-1-piperazinyl)-3-hydroxybenzyl)-N-(2-fluorophenyl)-N-methylbenzamide (+)-3-(($\alpha$R)-$\alpha$-((2S,5R)-4-Allyl-2,5-dimethyl-1-piperazinyl)-3-hydroxybenzyl)-N-(3-fluorophenyl)-N-methylbenzamide (+)-3-(($\alpha$R)-$\alpha$-((2S,5R)-4-Allyl-2,5-dimethyl-1-piperazinyl)-3-hydroxybenzyl)-N-ethyl-N-(4-fluorophenyl)benzamide, and pharmaceutically acceptable salts thereof.

Table I below shows the chemical structure of the nine above-identified particularly preferred compounds of the present invention, denoted herein as compounds "A", "B", "C", "D", "E", "F", "G", "H", and "I", respectively.

TABLE I

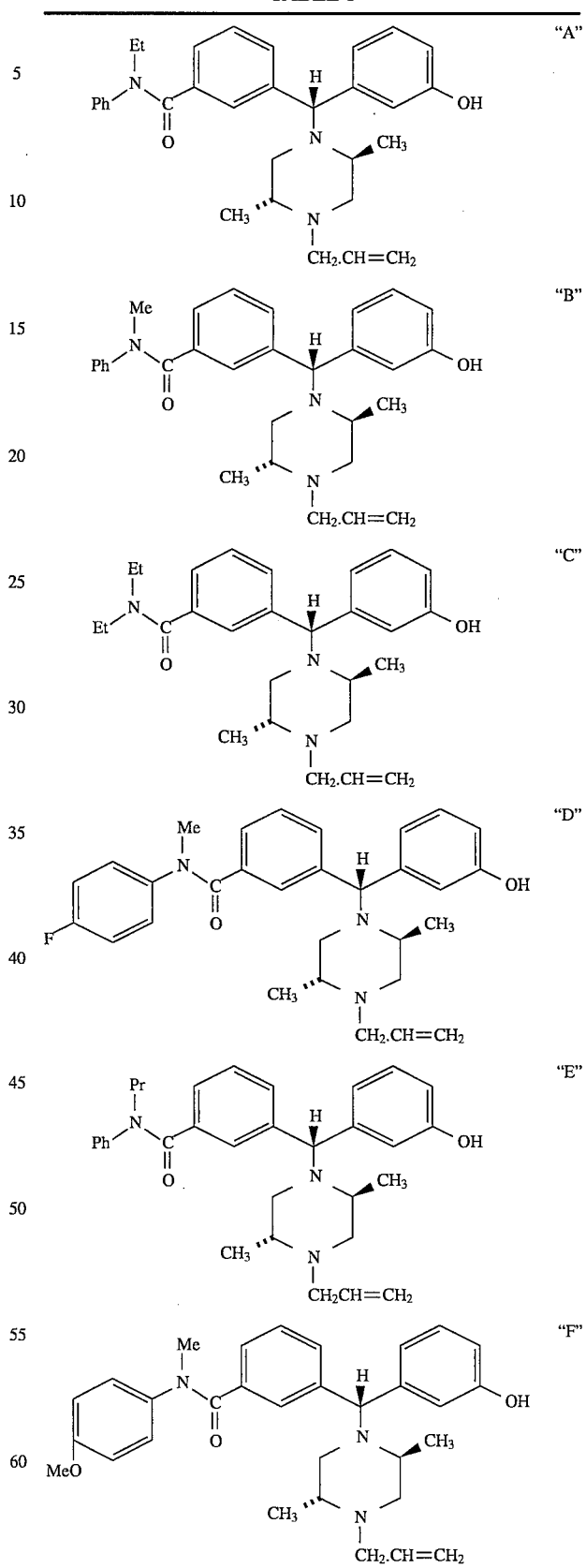

TABLE I-continued

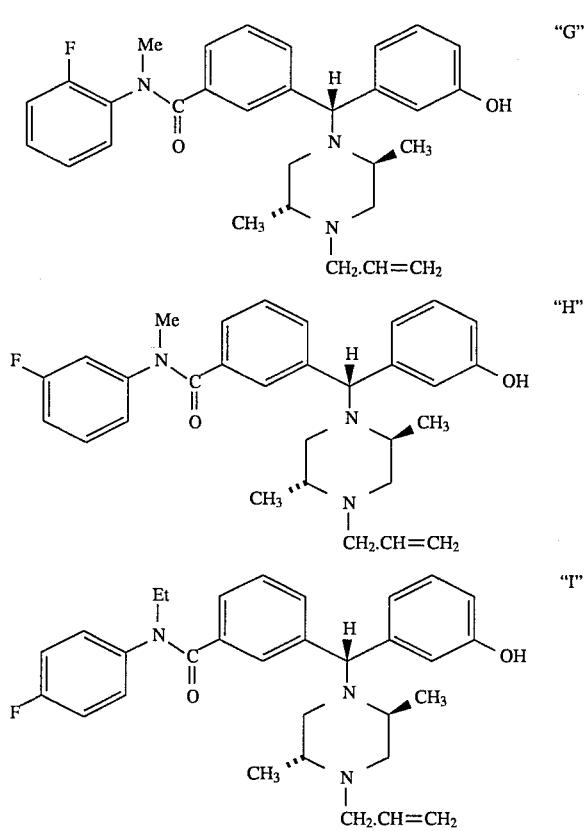

These compounds A, B, C, D, E, F, G, H and I are highly selective opioid receptor ligand species. All are efficacious in mediating analgesia. In general, the spectrum of analgesic utilities of diarylmethyl piperazine compounds of the invention may be readily determined without undue experimentation by simple receptor binding screening tests. In this respect, and merely by way of illustration, the diarylmethyl piperazine compounds of the invention which are predominantly mu receptor agonists may be utilized for example in mediating surgical analgesia. Diarylmethyl piperazine compounds of the invention which are predominantly delta receptor agonists may be utilized for example in mediating epidural analgesia. Diarylmethyl piperazine compounds of the invention which are mixed mu/delta opioid agonists, e.g., Compounds A, B, C, D, E, F, G, H, and I, may be utilized for example in mediating surgical and/or post-operative analgesia.

The mixed mu/delta receptor character of various compounds within the scope of the present invention entails a substantial advantage over various known mu receptor compounds currently employed as analgesics.

The vast majority of currently used high potency analgesics, including morphine, fentanyl, meperidine, sufentanil, and codeine, are mu receptor binding compounds. As is well established, these compounds, while highly efficacious for mediating analgesia, have accompanying side effects, including disorientation, attenuation of mental acuity, muscle rigidity, and respiratory depression, and withdrawal side-effects including nausea, vomiting, shakes, seizures, and sweats. Such side effects are typically absent or at least much reduced in use of analgesia-mediating delta receptor binding species. Accordingly, the use of mixed mu/delta receptor species of the present invention may attenuate or even eliminate the side effects normally attendant the use of mu receptor binding compounds.

The compounds of the invention when used in pharmaceutical or diagnostic applications desirably are prepared in substantially pure enantiomer form, with an enantiopurity of at least 90% enantiomeric excess (EE), preferably at least 95% EE, more preferably at least 98% EE, and most preferably at least 99% EE. Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

Compounds A, B, C, D, E, F, G, H, and I are enantiomerically pure analgesic agents exhibiting agonism at both mu and delta opioid receptors. In rodent test subjects, for example, these compounds produce analgesia comparable to mu-analgesic morphine, but produce a much reduced extent of muscle rigidity and respiratory depression. Further, rodent tests show these compounds to be free of proconvulsant activity, such as may be associated with structurally related pure delta agonists.

Although it might be assumed at first impression that all delta agonist compounds of the present invention would have similar in vivo profiles, with potencies parallel to mouse vas deferens activity, this is not invariably the case.

The diarylmethyl piperazine compounds of the invention include compounds which have significant potency in the receptor binding assay (rat brain), compounds that are predominantly active at one or the other of the delta receptor subtypes, and compounds having mu receptor activity or mixed mu receptor/delta receptor activity.

Binding assay and analgesia test results show that compounds of the present invention variously mediate analgesia in respect of a wide variety of stimuli and physiological perturbations. This in turn evidences a high level of complexity in neurotransmitter functions and stimulus-related responses associated with various opioid receptors, including mu receptors, delta receptors, delta receptor sub-types and kappa receptors.

A number of compounds of the present invention within formula (I), or their chemical precursors (which also in many instances constitute novel compounds and thus are contemplated within the scope of the present invention), evidence biological activities in addition to opioid activity, e.g., biological activity including sigma receptor binding affinity, and multidrug resistance activity.

As is apparent from the foregoing discussion, the compounds of the present invention have broad utility in the treatment of a wide variety of physiological conditions and disorders. The invention accordingly contemplates the use of such compounds in the manufacture of a medicament for the treatment or prophylaxis of such physiological conditions and disorders. In addition to those treatment applications already mentioned, other utilities for compounds of the present invention include the treatment of bronchial disorders such as asthma, emphysema, and apnea.

Further, endogenous opioids such as enkephalins and endorphins, and their neurological systems, have been identified in connection with various CNS disorders, such as compulsive behavior, depression, psychosis, etc., and agonist or antagonist species within formula (I) of the present invention have utility in combating such disorders.

Various agonist species as well as antagonist species of the compounds of formula (I) also find utility in the treatment of drug (opioid/narcotic) abuse/addiction, and thus have utility for replacement of methadone or other conventional opiate agents in drug rehabilitation programs, to the extent that conventional drug treatment agents have side effects or other disadvantages which contraindicate or limit their use.

Concerning drug addiction treatment with effective compounds within the broad scope of the present invention, it is noted that methadone is a mu-receptor opiate with actions similar to morphine, i.e., methadone is abusable and addictive. Methadone is used as a "maintenance therapy" agent for opiate addicts, so that such individuals can remain functional while satisfying their addictions in a safer and non-criminal manner. In this respect, compounds of the invention may have utility in place of, or as an adjunct to, currently used treatments for drug addiction, such as those involving naltrexone, methadone, clonidine, etc.

Certain compounds within the scope of the present invention, as discussed above, have utility in effecting local analgesia, such as spinal analgesia, and compounds of the invention may also find utility in appetite suppression applications, and the like.

Compounds of the present invention include various compounds which are delta-opioid agonists in the mouse vas deferens delta receptor subtype, as well as compounds which are antagonists at such delta receptor subtype. The compounds of the present invention also include compounds which are agonists or antagonists at the delta receptor in the brain, which appears, on the basis of empirical determinations, to be a different delta receptor subtype than the delta receptor in the mouse vas deferens. A substantial number of compounds of the aforementioned general formula (I) of the invention have either agonist or antagonist activity at both delta receptor subtypes. A number of these compounds have high activity at the mu-opioid receptor, either as pure mu receptor binding compounds or as mixed mu receptor/delta receptor binding compounds, and still other compounds within the broad scope of the present invention have significant affinity for the sigma receptor.

In in vitro tests for agonist/antagonist activity, such as receptor binding affinity tests, and inhibition of electrically stimulated muscle twitch tests, compounds of the present invention exhibit potency over a range of from nanomolar to micromolar concentrations, depending on the specific compound employed.

Compounds of the present invention have pharmaceutical activity, including, inter alia, analgesic activity, and are useful in treating animals, e.g., mammals such as humans, for conditions in which analgesia is desired.

A method of treating pain in an animal in need of such treatment comprises administering to the animal an effective analgesia-inducing amount of a compound of formula (I).

In addition, various compounds of the present invention having appertaining therapeutic utility may be usefully employed in the treatment of conditions including: drug and alcohol addiction/overdose; mental, emotional, and cognitive disorders; cough; lung edema; emesis; respiratory depression; and gastrointestinal disorders. Correspondingly, the present invention contemplates a method of treating an animal subject having condition(s) and in need of such treatment, comprising administering to such animal an effective amount of a compound of the present invention which is therapeutically effective for said condition.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered compounds of formula (I) at any suitable therapeutically effective and safe dosage, as may readily be determined within the skill of the art, and without undue experimentation.

In general, while the effective dosage of compounds of the invention for therapeutic use may be widely varied in the broad practice of the invention, depending on the specific application, condition, or disease state involved, as readily determinable within the skill of the art, suitable therapeutic doses of the formula (I) compounds, for each of the appertaining compositions described herein, and for achievement of therapeutic benefit in treatment of each of the conditions described herein, will be in the range of 1 microgram (µg) to 100 milligrams (mg) per kilogram body weight of the recipient per day, preferably in the range of 5 µg to 75 mg per kilogram body weight per day, and most preferably in the range of 10 µg to 50 mg per kilogram body weight per day. The desired dose is preferably presented as two, three, four, five, six, or more sub-doses administered at appropriate intervals throughout the day. These sub-doses may be administered in unit dosage forms, for example, containing from 10 µg to 1000 mg, preferably from 50 µg to 500 mg, more preferably from 50 µg to 250 mg, and most preferably from 50 µg to 10 mg of active ingredient per unit dosage form. Alternatively, if the condition of the recipient so requires, the doses may be administered as a continuous infusion.

The mode of administration and dosage forms will of course affect the therapeutic amounts of the compounds which are desirable and efficacious for the given treatment application.

For example, orally administered dosages typically are at least twice, e.g., 2–10 times, the dosage levels used in parenteral administration methods, for the same active ingredient. In oral administration for inducing analgesia, dosage levels for mu and/or mixed delta/mu receptor binding compounds of the invention may be on the order of 5–200 mg/70 kg body weight/day. Intrathecal administration dosage levels generally are on the order of about 10% of the levels characteristic of parenteral administration dosage levels. In tablet dosage forms, typical active agent dose levels suitable for inducing analgesia are on the order of 10–100 mg per tablet.

The compounds of formula (I) may be administered per se as well as in the form of pharmaceutically acceptable ethers, esters, salts, and other physiologically functional derivatives thereof.

The present invention also contemplates pharmaceutical formulations, both for veterinary and for human medical use, which comprise as the active agent one or more compound(s) of the invention.

In such pharmaceutical formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, nasal, ophthalmic, subcutaneous, intramuscular, intravenous, transdermal, spinal, intrathecal, intra-articular, intra-arterial, subarachnoid, bronchial, lymphatic, and intra-uterine administration. Formulations suitable for parenteral administration are preferred.

When the active agent is utilized in a formulation comprising a liquid solution, the formulation advantageously may be administered parenterally. When the active agent is employed in a liquid suspension formulation or as powder in a biocompatible carrier formulation, the formulation may be advantageously administered orally, rectally, or bronchially.

When the active agent is utilized directly in the form of a powdered solid, the active agent may advantageously administered orally. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier which constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The compounds of formula (I) and pharmaceutically acceptable esters, salts, and other physiologically functional derivatives thereof, may be formed by the exemplary synthetic techniques described in the aforementioned International Patent Application No. WO93/15062, filed Feb. 2, 1993.

The present invention also contemplates a process for the preparation of a compound of formula (I), as defined hereinabove, or a pharmaceutically acceptable ester, ether, salt, or other physiologically functional derivative thereof, said process comprising a synthesis procedure selected from the group consisting of synthesis procedures (A), (B) and (C) below.

(A) the alkylation of a piperazine of formula (IV) by an alkylating agent of formula (III),

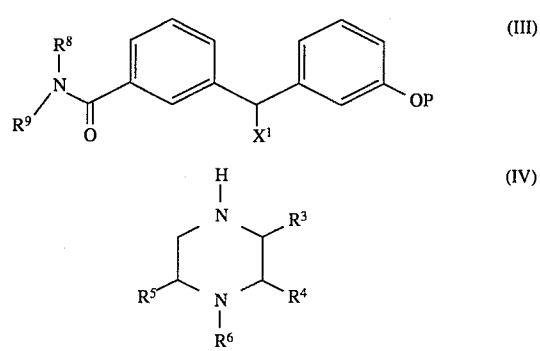

wherein $R^3$ to $R^6$ and $R^8$ and $R^9$ are as defined in any of the preceding claims, P is hydrogen or an hydroxy-protecting group and $X^1$ is a leaving group; and, when $R^6$ is hydrogen, optionally alkylating the resulting compound of formula (I) with an alkylating agent of the formula $R^6$—$X^1$, wherein $R^6$ is saturated $C_1$–$C_6$ hydrocarbyl, unsaturated $C_3$–$C_6$ hydrocarbyl or $C_2$–$C_6$ methoxyalkyl and $X^1$ is a leaving group, or optionally alkylating the resulting compound of formula (I) by reductive amination with a $C_1$–$C_6$ aldehyde in the presence of a reducing agent;

(B) reacting a compound of formula (V),

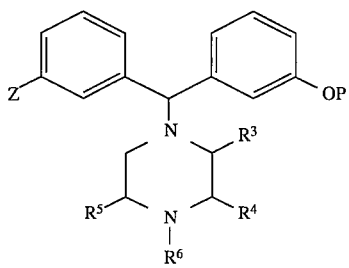

(V)

wherein $R^3$ to $R^6$ are as defined above, P is as defined above and Z is bromo, iodo or trifluoromethylsulfonyl as appropriate, with (a) in the case where Z is bromo or iodo; an alkyl metal, or suitably reactive metal, optionally transmetallating the resulting metallic compound with a transition metal species to provide a different metallic compound, reacting the resulting metallic compound with carbon dioxide and converting the resulting carboxylic acid to the corresponding acid chloride, anhydride or ester, and reacting the resulting acid chloride, anhydride or ester with an amine of the formula $HNR^8R^9$ wherein $R^8$ and $R^9$ are as defined herein or reacting the resulting metallic compound with an aminocarbonyl chloride compound of formula $ClCONR^8R^9$, wherein $R^8$ and $R^9$ are as defined herein; or (b) in the case where Z is bromo, iodo or trifluoromethylsulfonyl; a cyanating reagent, hydrolyzing the resulting nitrile with alkali or aqueous mineral acid, converting the resulting carboxylic acid to the corresponding acid chloride, anhydride or ester, and reacting the resulting acid chloride, anhydride or ester with an amine of the formula $HNR^8R^9$ wherein $R^8$ and $R^9$ are as defined herein; or (c) in the case where Z is bromo, iodo or trifluoromethylsulfonyl; excess amine of the formula $HNR^8R^9$ wherein $R^8$ and $R^9$ are as defined herein and carbon monoxide in the presence of a transition metal catalyst to yield a compound of formula (I), wherein $R^8$ and $R^9$ are as defined herein; or (C) reacting a compound of formula (VI), with a phenyl-metallic compound of formula (VII):

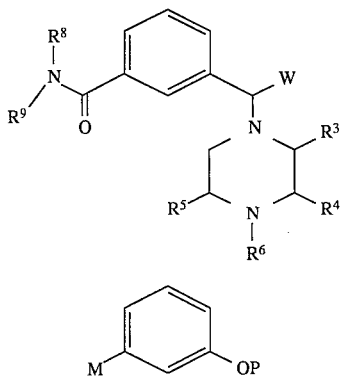

(VI)

(VII)

wherein $R^3$ to $R^6$ and $R^8$ and $R^9$ are as defined herein, P is hydrogen or a hydroxy-protecting group, M is a metal species and W is benzotriazolyl or trichlorotitaniumoxy; (Katritzky, A. R.; Yannakopoulou, K.; Lue, P.; Rasala, D.; Urogdi, L; J. Chem. Soc., Perkin Trans. 1, 1139, (1989); Seebach, D.; Betscart, C.; Schiess, M. Helv. Chim. Acta, 67, 1593. (1984)) and, when P is an hydroxy-protecting group, deprotecting the hydroxy group;

optionally converting the resulting compound of formula (I) into a pharmaceutically acceptable ether, ester or salt thereof or a physiologically functional derivative thereof.

Procedure A

The reaction between an alkylating agent of formula (III) and a piperazine of formula (IV) may be carried out in a solvent such as toluene or acetonitrile.

Alkylating agents of the formula $R^6$—$X^1$ are commercially available or may be prepared by published procedures. As an alternative to alkylation with an alkylating agent $R^6$—$X^1$, the method of reductive amination may be employed in which an appropriate commercially available $C_1$—$C_6$ aldehyde is reduced with a reducing agent such as sodium cyanoborohydride in solvents such as alcohols or ethers.

Procedure B (a) A compound of formula (I) may be prepared from a compound of formula (V), wherein Z is bromo or iodo and P is a hydroxy-protecting group, such as tert-butyldimethylsilyl, by low-temperature (e.g. −60° C. to −78° C.) metal exchange of the reactive halogen with an organometallic reagent, such as n-butyllithium, or an activated form of a metal, such as lithium or magnesium, to provide an intermediate metallic compound, followed by reaction with carbon dioxide to provide the carboxylic acid in an anhydrous solvent such as tetrahydrofuran, under an inert atmosphere (e.g. nitrogen). The carboxylic acid may then be converted to the carboxamide of formula (I) by the methods described below.

Alternatively, the intermediate metallic compound generated from a compound of formula (V) may be treated with an appropriate carbamoyl chloride ($ClCONR^8R^9$) to produce a compound of formula (I).

(b) A compound of formula (I) may also be prepared from a compound of formula (V) wherein Z is bromo, iodo or triflate (trifluoromethylsulfonyl) by treatment with a cyanating reagent, such as cuprous cyanide, in a suitable solvent such as dimethylformamide or N-methylpyrrolidinone, to provide the corresponding compound of formula (V) wherein Z is nitrile, which may be further hydrolyzed to the corresponding carboxylic acid with alkali or aqueous mineral acid. The carboxylic acid may then be converted to a compound of formula (I) by various means known in the art, such as formation of the acid chloride (e.g. with thionyl chloride or oxalyl chloride) or by formation of the mixed anhydride (e.g. with isobutyl chloroformate) or by formation of an activated ester with conventional peptide-coupling reagents (e.g. dicyclohexylcarbodiimide or benzotriazol-1-yloxytris(dimethylamino)phosphonium hexafluorophosphate), any of which activated intermediates may be converted to the desired carboxamide of formula (I) by reaction with an appropriate amine ($HNR^8R^9$) in a suitable solvent such as dichloromethane or dimethylformamide.

(c) A compound of formula (I) may also be prepared from a compound of formula (V), wherein Z is bromo, iodo or triflate, by treatment with a transition metal catalyst, such as tetrakis(triphenylphosphine)palladium, in the presence of excess amine and carbon monoxide in a solvent such as tetrahydrofuran or acetonitrile.

Procedure C

A compound of formula (VI) may be prepared as a reactive intermediate by combining an aldehyde of formula (VIII) with a piperazine of formula (IV)

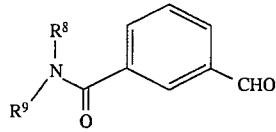

(VIII)

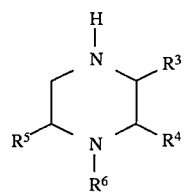

(IV)

wherein $R^3$ to $R^6$ and $R^8$ and $R^9$ are as defined herein, in the presence of titanium tetrachloride or benzotriazole in a suitable solvent such as toluene or dichloromethane, or for an intermediate of formula (VI) where W is benzotriazolyl, the reactive intermediate may be isolated, if desired, by crystallization or other appropriate means.

A compound of formula (I) may be obtained as a single enantiomeric species by classical resolution with an enantiopure acid, such as mandelic acid, or by formation of readily separable diastereomers by an enantiopure derivatizing agent, or by chiral chromatography, or by enzymatic resolution of a compound of formula (I) or a suitable derivative, or by preparation of the compound of formula (I) from enantiopure precursors, which may themselves be obtained as single enantiomers by similar means.

Compounds of formula (III) may be obtained from the appropriate alcohols of formula (IX), where the phenol is protected with a suitable protecting group P, by methods such as halogenation with thionyl chloride or triphenylphosphine/carbon tetrabromide, or reaction with methanesulfonyl chloride or toluenesulfonyl chloride, in a solvent such as dichloromethane.

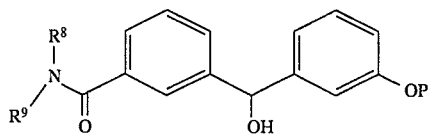

(IX)

Piperazines of formula (IV) are commercially available, or may be prepared by published procedures or variations of published procedures where $R^6$ is varied by appropriate alkylation with agents $R^6—X^1$.

Compounds of formula (V) may be prepared by alkylation of a piperazine of formula (IV) with an alkylating agent of formula (X), in similar fashion to the piperazine alkylation described above. Alkylating agents of formula (X) are likewise obtained from alcohols of formula (XI) by similar methods to those described above for compounds of formula (III).

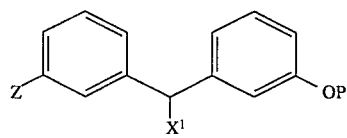

(X)

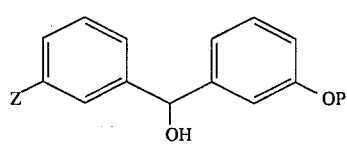

(XI)

Alcohols of formula (IX) or (XI) may be prepared by low-temperature (e.g. −60° C. to −78° C.) addition of substituted arylmetallic species, prepared from compounds of formula (XII), wherein Z is reactive halogen (e.g. iodine or bromine), by methods described hereinabove, to protected benzaldehydes of formula (XIII).

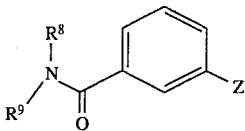

(XII)

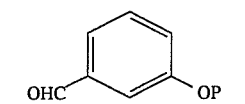

(XIII)

Conversely, compounds of formula (IX) or (XI) may also be formed by similar addition of aforementioned protected phenylmetallic species (VII) to benzaldehydes of formula (VIII).

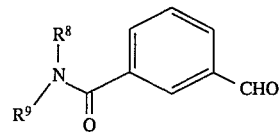

(VIII)

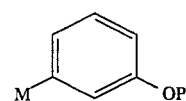

(VII)

Compounds (VII), (VIII), (XII) and (XIII) and their suitably protected derivatives may be prepared from commercially available materials by standard literature procedures.

A compound of formula (I) may be converted into a pharmaceutically acceptable ester by reaction with an appropriate esterifying agent, e.g. an acid halide or anhydride. The compound of formula (I), including esters thereof, may be converted into pharmaceutically acceptable salts thereof in conventional manner, for example, by treatment with an appropriate acid. An ester or salt of a compound of formula (I) may be converted into the parent compound, for example, by hydrolysis. Phenolic ethers of a compound of formula (I) wherein P is $C_1$–$C_6$ alkyl, may be prepared as described hereinbefore.

Based on the foregoing as well as general synthesis considerations, it will be appreciated that various synthesis are useful for preparation of diarylmethyl piperazine compounds of the present invention, as will be readily apparent to those of ordinary skill in the art, illustrative synthetic methods for production of compounds within the broad scope of the present invention are set out below by way of example, it being understood that compounds of the invention are amenable to manufacture by various other synthesis routes and methods within the skill of the art, and that the illustrative synthesis methods set out below are therefore not to be limitingly construed as regards the scope of the invention. It is to be further appreciated that the novel compounds of the present invention comprehend various novel intermediates, precursors, pro-drugs, analogues, and derivatives of compounds specifically identified herein with reference to the invention.

When the synthesis procedures which are employed for producing compounds of the invention yield racemic mixtures as reaction products, such racemic mixtures may be resolved by suitable means and methods well-known and established in the art, as for example by formation of diastereomeric salts with enantiopure carboxylic acids, by chiral chromatographic resolution, by enzymatic resolution, or by other suitable conventional methods.

SYNTHESIS REACTION SCHEMES

Set out below are illustrative synthetic schemes for the formation of racemic (±)-3-((αR*)-α-((2S*,5R*)-4-allyl-2,5-dimethyl-1-piperazinyl)-3-hydroxybenzyl)-N,N-diethylbenzamide, hereafter referred to as Compound (±)-C, which may be obtained as its constituent enantiomers by applying classical resolution or chiral synthesis methods to the final product or to appropriate intermediates. Such methods are further illustrated for the obtention of preferred enantiomer (±)-3-((αR)-α-((2S,5R)-4-allyl-2,5-dimethyl-1-piperazinyl)-3-hydroxybenzyl)-N,N-diethylbenzamide, referred to herein as Compound C, which is more specifically described in Example 1 hereof. The illustrative synthesis schemes and resolution methodology of the ensuing description may likewise be employed in the synthesis and resolution of other compounds of the invention, or alternatively other synthesis and/or resolution methodologies may be usefully employed within the skill of the art.

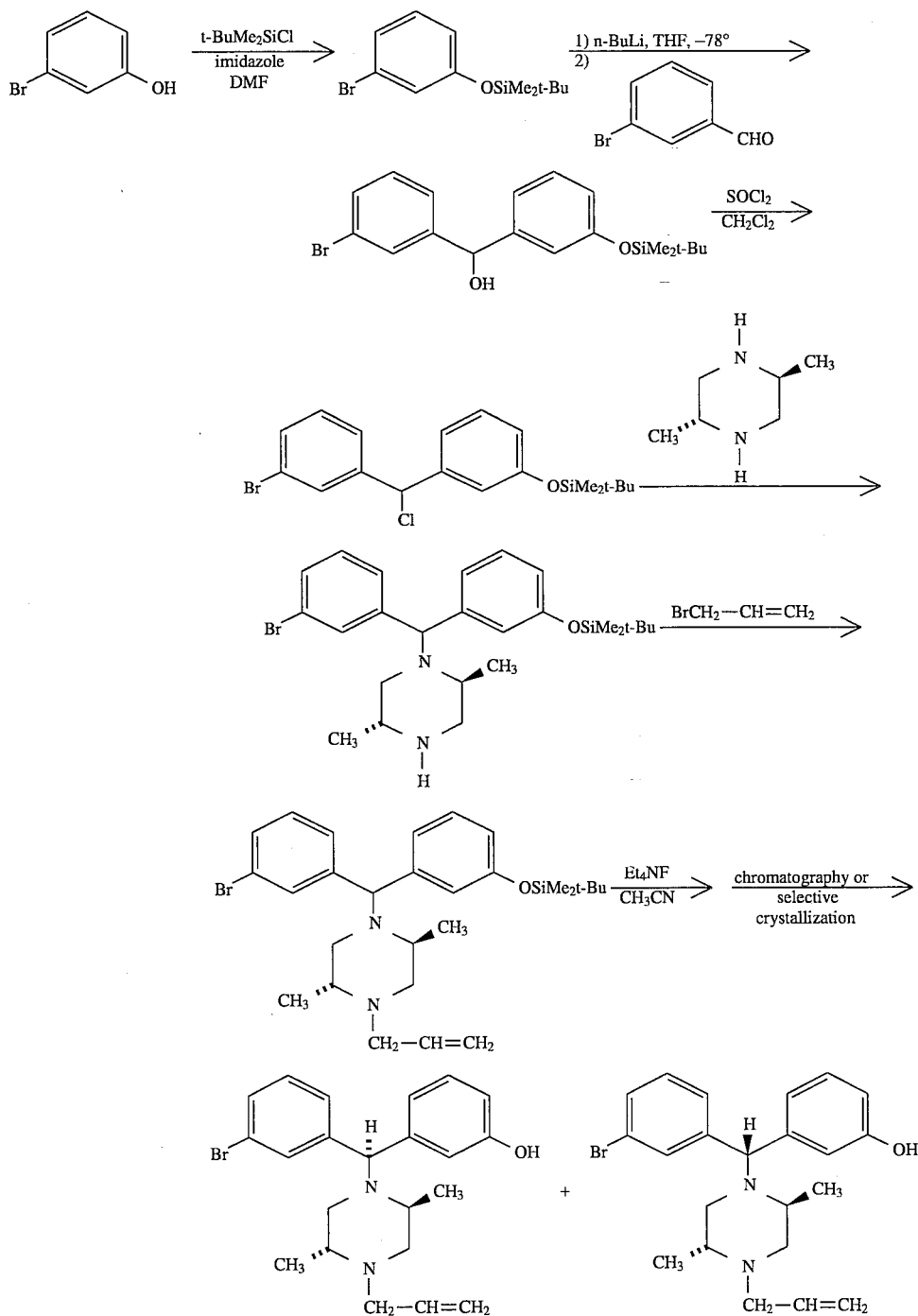

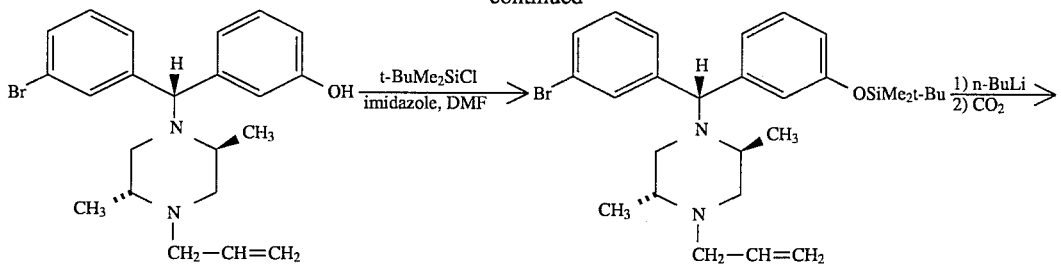

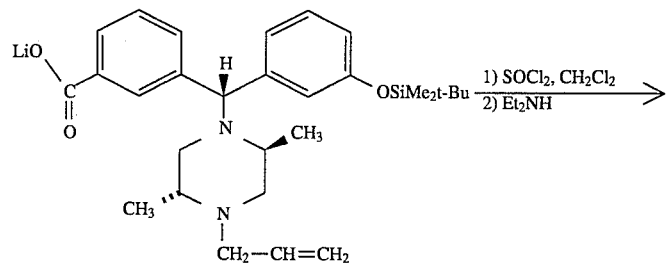

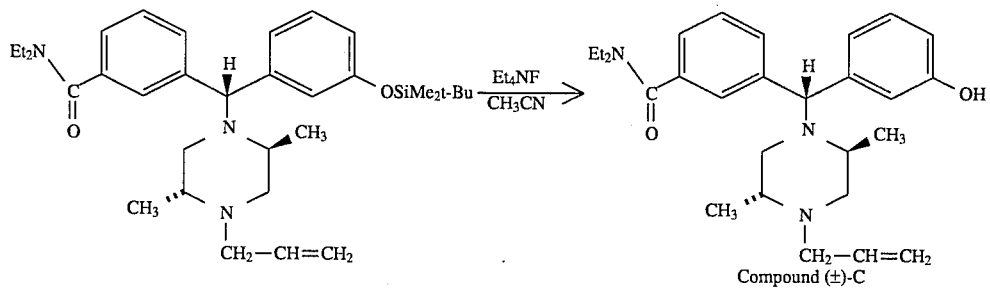

With respect to the foregoing synthesis scheme, the initial benzhydryl alcohol could be prepared from 3-(t-butyldimethylsilyloxy)bromobenzene by the following scheme:

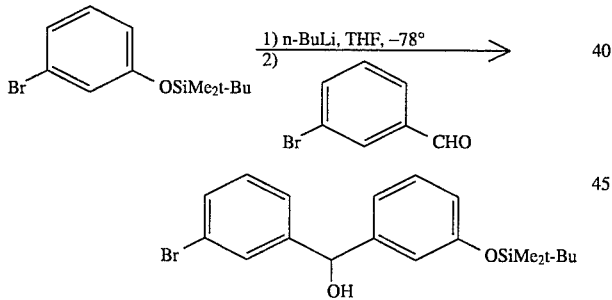

The intermediate could also be prepared via the benzophenone, which in turn could be obtained from an organometallic addition to 4-bromobenzonitrile:

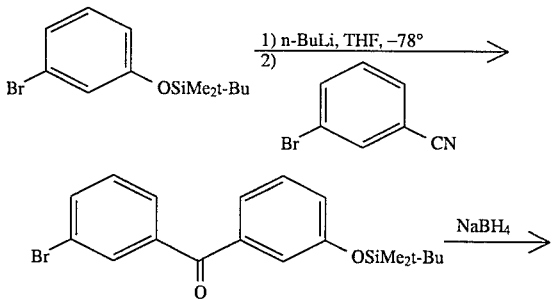

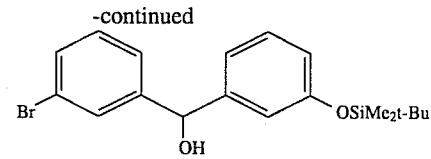

Other alternatives to intermediates involve condensation of an appropriately substituted piperazine with carbonyl compound. Condensation with a benzaldehyde could provide an imminium salt that could add an aryllithium to provide benzhydryl piperazine compounds wherein X=CONEt$_2$, Y=CH$_2$CH=CH$_2$, or wherein X=Br, Y=CH$_2$CH=CH$_2$, as mixtures with their diastereomers, or protected precursors to those compounds.

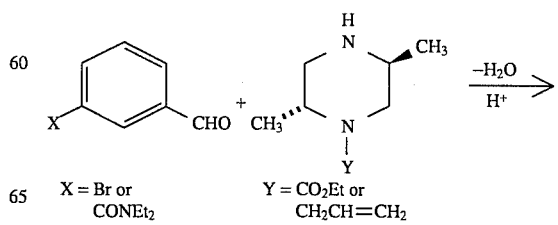

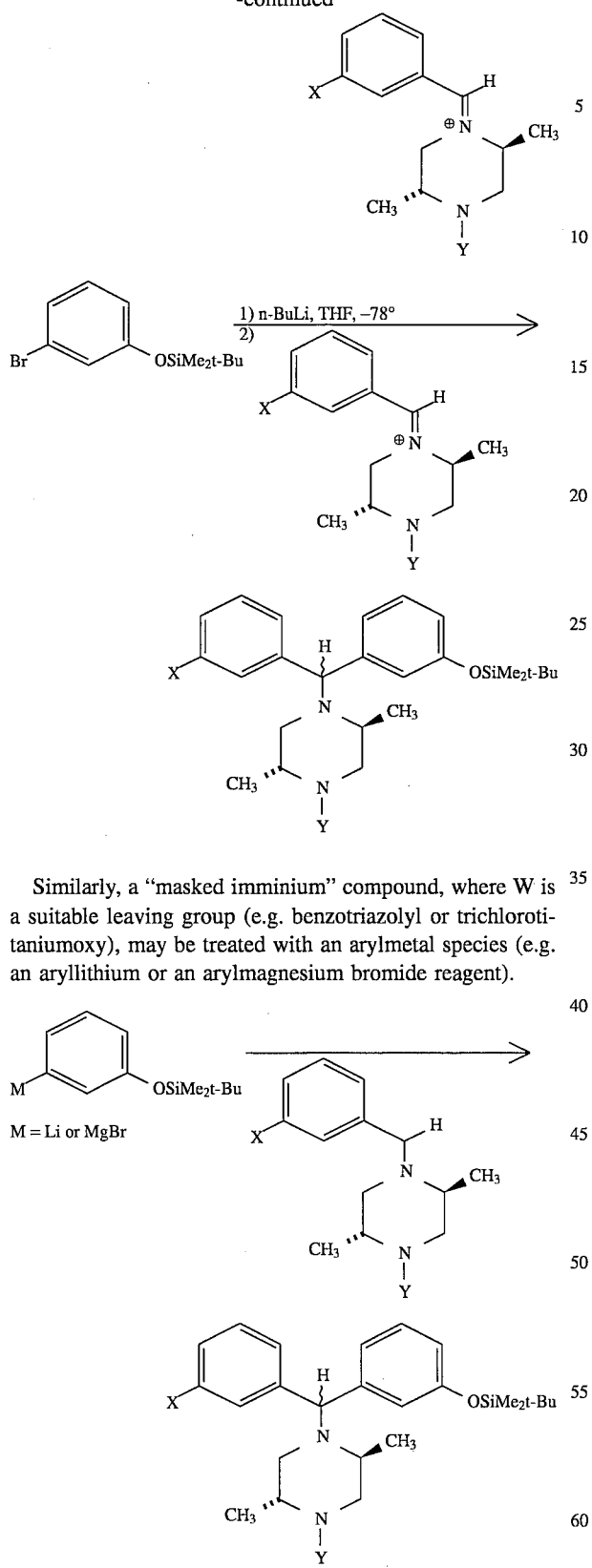

Similarly, a "masked imminium" compound, where W is a suitable leaving group (e.g. benzotriazolyl or trichlorotitaniumoxy), may be treated with an arylmetal species (e.g. an aryllithium or an arylmagnesium bromide reagent).

wherein the benzylpiperazine may dissociate to generate the requisite imminium ion in situ.

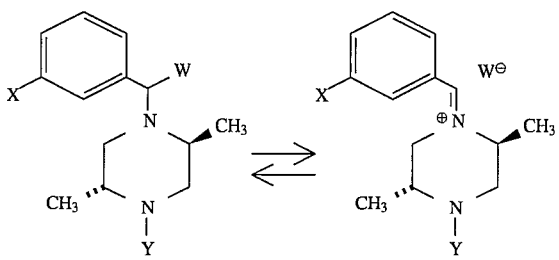

Similarly, reductive amination of the appropriate benzophenone with a suitable piperazine may provide the desired compounds directly.

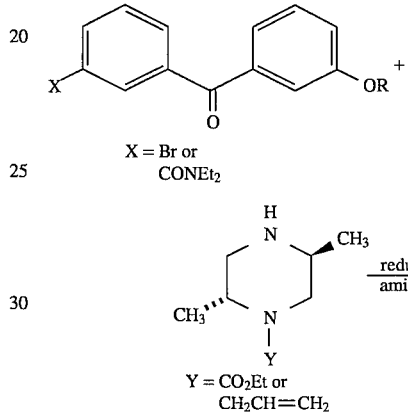

X = Br or CONEt₂

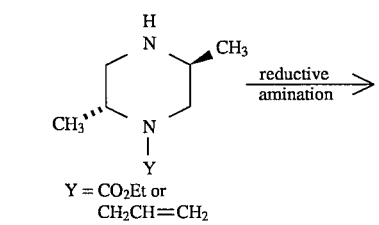

Y = CO₂Et or CH₂CH=CH₂

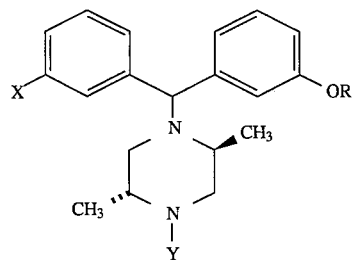

Compound (±)-C can also be synthesized by the alternative synthetic route set out below.

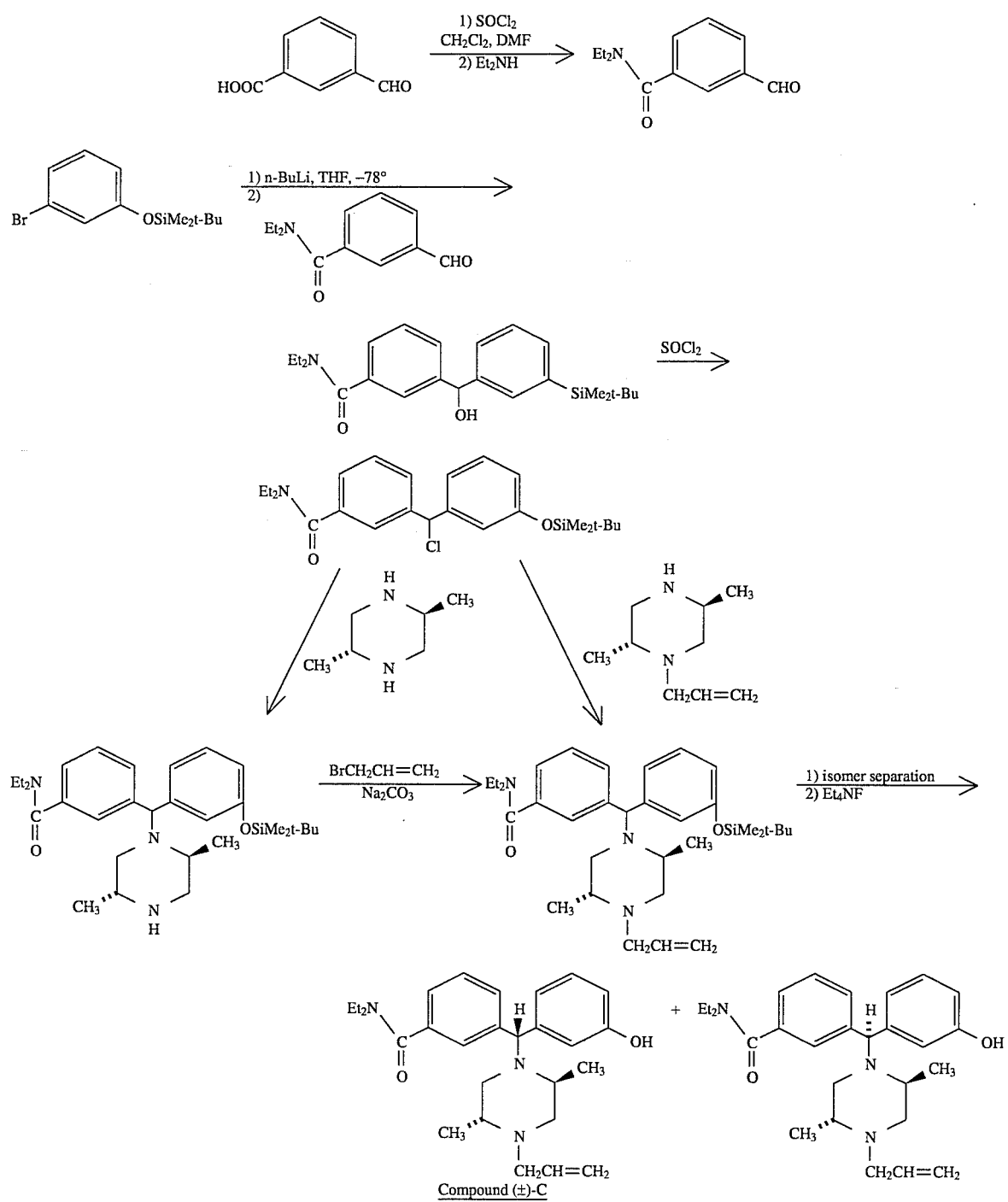
The trans-1-allyl-2,5-dimethylpiperazine reactant utilized in the above synthesis scheme may suitably be formed by the following synthetic process.
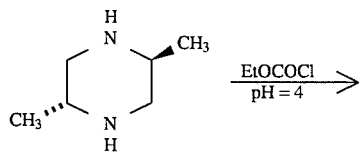
-continued
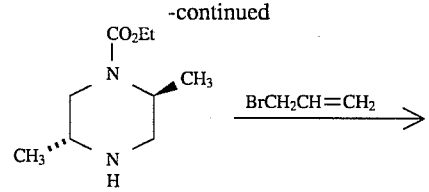

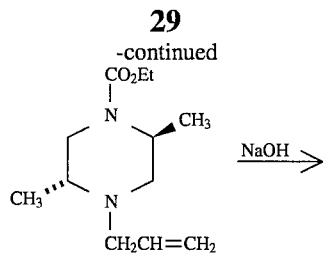

The racemic trans-1-allyl-2,5-dimethylpiperazine may be resolved into its constituent enantiomers by classical resolution with an enantiopure carboxylic acid to provide chiral intermediate (2R,5S)-1-allyl-2,5-dimethylpiperazine for the production of the preferred (+)-antipode Compound C.

The (2R,5S)-1-allyl-2,5-dimethylpiperazine may also be made in enantiopure form, by the illustrative synthetic route outlined below.

When the enantiopure (2R,5S)-1-allyl-2,5-dimethylpiperazine is treated with a racemic benzhydryl chloride, the resultant product is a mixture of two enantiopure diastereomers that can be separated by conventional methods such as chromatography or fractional crystallization.

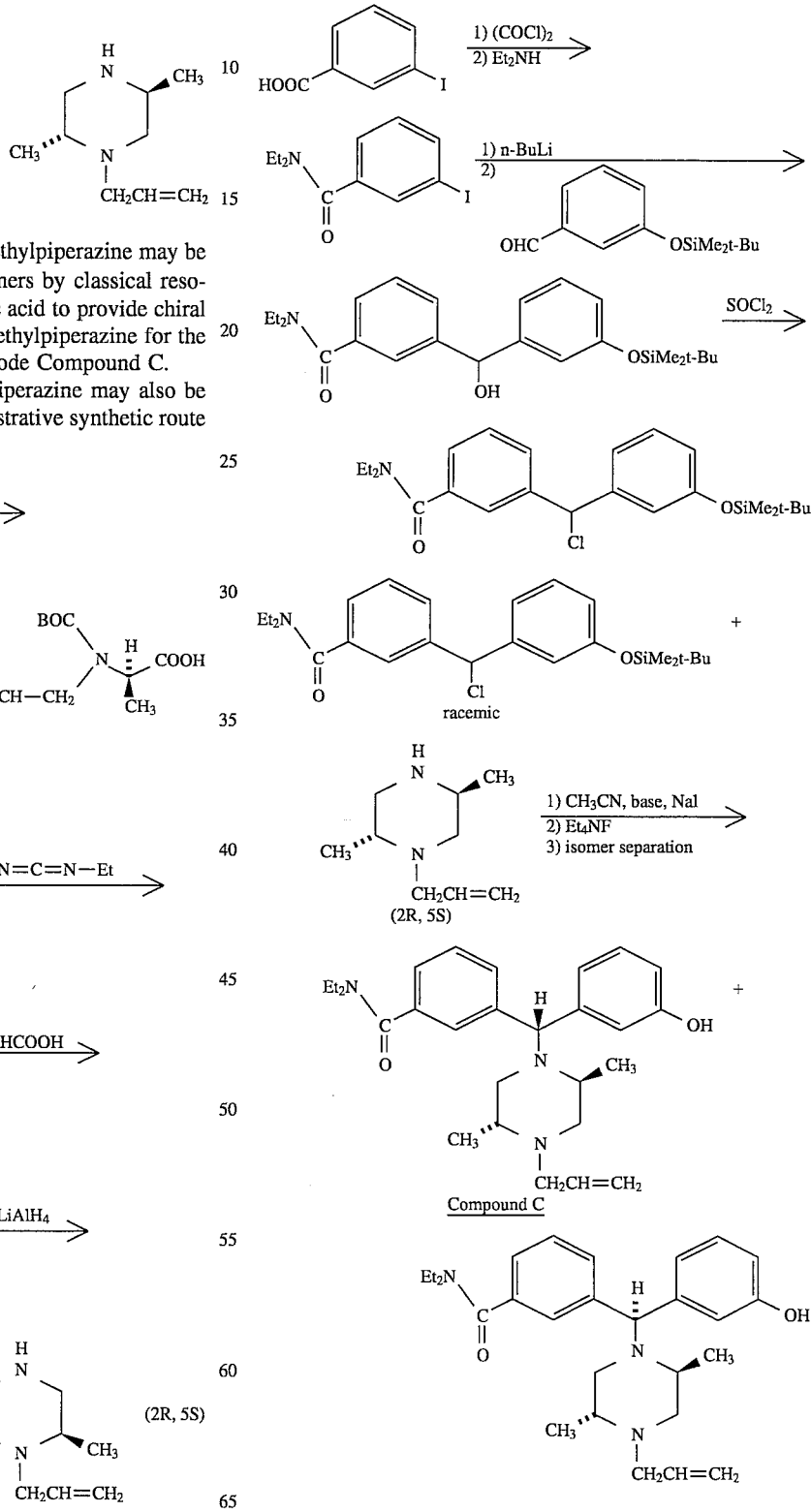

In addition to the foregoing, Compounds C or (±)-C may be synthesized via a nitrile synthesis route, utilizing cuprous cyanide as a nitrilation agent, as shown below.
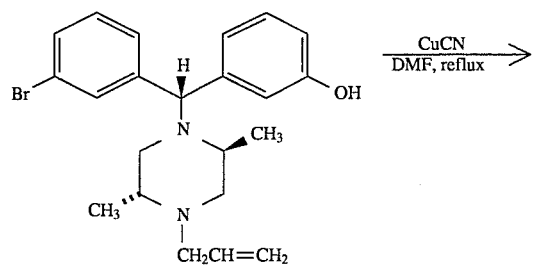
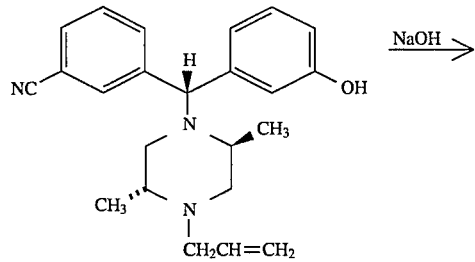
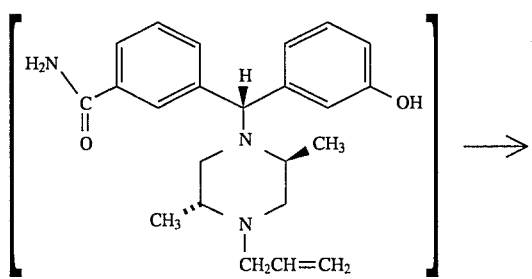
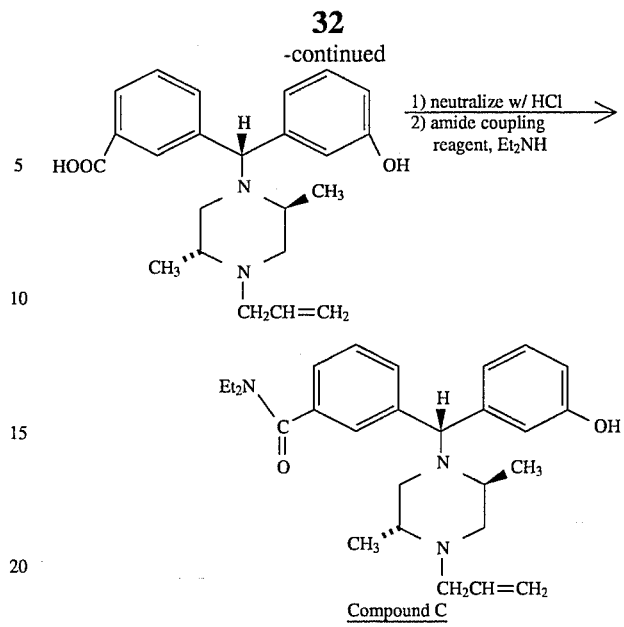
Alternative syntheses of Compound C from a corresponding halogenated compound are set out below.
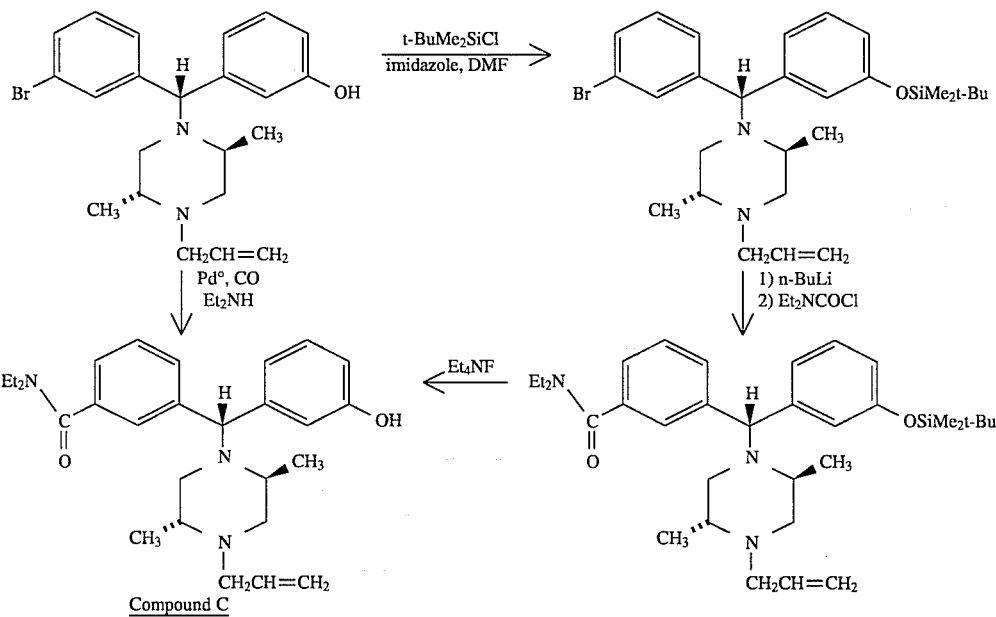

The foregoing have been illustratively set out as examples of synthetic techniques which may be usefully employed to form compounds such as Compounds C or (±)-C, as well as other benzhydrylpiperazine compounds of the present invention, via corresponding or analogous reagents. Of the foregoing synthetic methods described to form Compound C, a synthesis route employing (2R,5S)-1-allyl-2,5-dimethylpiperazine is empirically preferred due to its greater convenience as compared to the other described synthetic routes.

The features and advantages of the invention are more fully shown with respect to the following non-limiting examples.

Certain specifications and methods common to many of the following examples relating to chemical synthesis are described in the next paragraph.

Melting points were determined with a Thomas-Hoover apparatus and are uncorrected. All chemical reagents were purchased from Aldrich Chemical Company, Milwaukee, Wis., unless otherwise specified. Commercial solvents were used without further purification except tetrahydrofuran, which was distilled from potassium metal. Nuclear magnetic resonance (NMR) spectra were variously obtained with Perkin-Elmer R-24, Varian XL-200, or XL-300 spectrometers. HPLC analyses were performed with a Waters liquid chromatography system equipped with a 700 Satellite WISP, 600E System Controller and a 991 Photodiode Array detector, using either a 4.6×250 mm Cyclobond I column (Advanced Separations Technologies, Whippany, N.J.) or a μ-Bondapak C-18 column (125 Å, 3.9×300 nm. Waters Chromatography Division, Millipore Corporation, Milford, Mass., at a flow rate of 1 ml/min. Analytical gas chromatography was performed on a Hewlett-Packard Series II instrument, Model 5890 with flame ionization detector using helium as the carrier gas (injector temperature, 225° C.; detector temperature, 250° C.). Optical rotations were obtained with a Perkin-Elmer 241 polarimeter. Mass spectra were performed by Oneida Research Services, Whitesboro, N.Y. X-Ray crystallography was performed by Molecular Structure Corporation, College Station, Tex. Analytical thin layer chromatography was performed on Analtech glass plates pre-coated with silica gel GF (250 microns), and preparative thin layer chromatography on Analtech Uniplates pre-coated with silica gel GF (1000 and 2000 microns). Elemental analyses were performed by Atlantic Microlab, Norcross, Ga.

(REFERENCE) EXAMPLE 1

(+)-3-((αR)-α-((2S,5R)-4-Allyl-2,5-dimethyl-1-piperazinyl)-3-hydroxybenzyl)-N,N-diethylbenzamide 3-Iodobenzoic acid (55.5 g, 0.224 mol) was dissolved in tetrahydrofuran (220 mL) and oxalyl chloride (22 mL, 0.252 mol). Catalytic dimethylformamide (4 drops) was added, the solution was stirred at room temperature for 1 hour, and the solvent was removed under vacuum. The residue was dissolved in 220 mL petroleum ether (35°–60° C. boiling range) and cooled to 0° C. in an ice bath. Diethylamine (55 mL, 0.532 mol) was then added dropwise over 15 minutes. The reaction mixture was stirred an additional 15 minutes in the ice bath, then diluted with ethyl acetate (100 mL) and washed with saturated sodium chloride solution (50 mL). The organic layer was separated, dried over magnesium sulfate, and concentrated in vacuo to approximately half of the original volume. The solution was then filtered through a small pad of silica gel, using ethyl acetate to wash the pad. All volatiles were removed in vacuo, and the product was dried under high vacuum to give 65.69 g (97%) of N,N-diethyl-3-iodobenzamide as an amber oil. NMR (300 MHz, CDCl$_3$): δ1.11 (br s, 3H); 1.21 (br s, 3H); 3.23 (br s, 2H); 3.51 (br s, 2H); 7.13 (ddd, J$_1$=0.8 Hz, J$_2$=7.6 Hz, J$_3$=7.6 Hz, 1H); 7.32 (ddd, J$_1$=1.3 Hz, J$_2$=1.3 Hz, J$_3$=7.5 Hz, 1H); 7.71 (d, J=1.2 Hz, 1H); 7.72 (ddd, J$_1$=1.3 Hz, J$_2$=1.3 Hz, J$_3$=approx. 8.0 Hz (partially obstructed), 1H). Mass spectrum (CI—CH$_4$) m/e: 304 (M+1, 100%). Calc. for C$_{11}$H$_{14}$NOI: C, 43.58; H, 4.65; N, 4.62; I, 41.86. Found: C, 43.68; H, 4.64; N, 4.64; I, 41.92.

3-Hydroxybenzaldehyde (70 g, 0.57 mol), tert-butyldimethylsilyl chloride (92 g, 0.61 mol), and imidazole (92 g, 1.35 mol) were combined in dimethylformamide (250 mL). The mixture was stirred at room temperature, under nitrogen, for 1 hour. The solution was poured into water (1.5 L) and extracted with 2×500 mL petroleum ether (35°–60° C. boiling range). The organic solution was washed with saturated sodium chloride solution (100 mL), dried over magnesium sulfate, treated with silica gel (20 g), filtered, and concentrated in vacuo. The residue was dried further under high vacuum to yield 126.6 g (94%) of the air and light-sensitive 3-((tert-butyldimethylsilyl)oxy)benzaldehyde as an amber oil. NMR (300 MHz, CDCl$_3$): δ0.22 (s, 6H); 0.99 (s, 9H); 7.10 (ddd, J$_1$=1.2 Hz, J$_2$=2.5 Hz, J$_3$=7.9 Hz, 1H); 7.32 (dd, J$_1$=1.5 Hz, J$_2$=2.4 Hz, 1H); 7.39 (t, J=7.8 Hz, 1H); 7.47 (ddd, J$_1$=1.3 Hz, J$_2$=1.3 Hz, J$_3$=7.6 Hz, 1H); 9.95 (s, 1H). Mass spectrum (CI—CH$_4$) m/e: 237 (M+1, 100%). Calculated for C$_{13}$H$_{20}$O$_2$Si: C, 66.05; H, 8.53. Found: C, 65.95; H, 8.56.

n-Butyllithium in hexanes (280 mL of a 2.5M solution) was added via a dropping funnel to tetrahydrofuran (1.4 L) at −78° C., under nitrogen. When the n-butyllithium solution had cooled back to −78° C., a solution of N,N-diethyl-3-iodobenzamide (106 g, 0.35 mol) in tetrahydrofuran (350 mL) was added slowly over 20 minutes. The internal temperature rose to −65° C. during the addition. After the addition was complete, the solution was stirred for 10 minutes, and a solution of 3-((tert-butyldimethylsilyl)oxy)benzaldehyde (88 g, 0.37 mol) in tetrahydrofuran (90 mL) was added slowly over 7 minutes. The reaction mixture was stirred for an additional 5 minutes at −78° C. and allowed to warm to −10° C. The mixture was poured into 875 mL petroleum ether (35°–60° C. boiling range) and sodium phosphate dibasic solution (350 mL of 2M aqueous solution), shaken, and the organic phase separated. The organic phase was dried over magnesium sulfate and concentrated in vacuo. The residue was dissolved in an ethyl acetate-petroleum ether mixture (1:3, 90 mL), placed on a column of silica gel (1 kg), and washed with ethyl acetate-petroleum ether (1:3) to remove fast eluting impurities. Elution with ethyl acetate yielded, after in vacuo concentration, 115.9 g (80%) of 3-(3-((tert-butyldimethylsilyl)oxy)-α-hydroxybenzyl)-N,N-diethylbenzamide as a viscous amber oil. NMR (300 MHz, DMSO-d$_6$): δ0.13 (s, 6H); 0.92 (s, 9H); 0.98 (br s, 3H); 1.11 (br s, 3H); 3.10 (br s, 2H); 3.39 (br s, 2H); 5.69 (d, J=4.1 Hz, 1H); 5.96 (d, J=4.2 Hz, 1H); 6.68 (dd, J$_1$=1.9 Hz, J$_2$=7.7 Hz, 1H); 6.84 (s, 1H); 6.97 (d, J=7.7 Hz, 1H); 7.16 (d, J=approx. 8 Hz (partially obscured), 1H); 7.17 (t, J=7.7 Hz, 1H); 7.28 (s, 1H); 7.35 (t, J=7.8 Hz, 1H); 7.42 (d, J=7.6 Hz, 1H). Mass spectrum (CI—CH$_4$) m/e: 414 (M+1, 11%), 178 (32%). Calc. for C$_{24}$H$_{35}$NO$_3$Si: C, 69.69; H, 8.53; N, 3.39. Found: C, 69.65; H, 8.56; N, 3.40.

A 12 L, 3-necked round bottom flask was charged with trans-2,5-dimethylpiperazine (767 g, 6.72 mol), which had been recrystallized from toluene to mp=115°–119° C., and 600 mL of water. The flask was cooled in an ice bath and a solution of methanesulfonic acid (1290 g, 13.4 mol) in 600 mL of water was added slowly with stirring and cooling to maintain the temperature below 40° C. The solution was cooled to 20° C. and 800 mL of ethanol was added. A 500 mL addition funnel was filled with 60% aqueous potassium acetate from a 2 L reservoir of the solution, and potassium acetate was added to the reaction flask to adjust the pH to 4.0. A second addition funnel was charged with a solution of ethyl chloroformate (642 mL, 6.71 mol) in 360 mL of tetrahydrofuran. The ethyl chloroformate and potassium acetate solutions were simultaneously added dropwise with adjustment of rate to maintain the reaction solution at pH 4.0±0.1, with cooling as necessary to maintain temperature at 25° C. After addition of the ethyl chloroformate was complete, the reaction was stirred for 1 hour with continued addition of potassium acetate solution to maintain a pH of 4.0. The organic solvents were removed by distillation under vacuum. The remaining aqueous solution was washed with 1500 mL of ethyl acetate to remove any bis-carbamate impurity. The ethyl acetate wash was extracted with two 500 mL portions of 1M hydrochloric acid to recover desired product. The acid extracts were combined with the original aqueous solution and the pH was adjusted to 11 by addition of 10M sodium hydroxide, with cooling to maintain temperature below 40° C. The aqueous solution was extracted with two 1500 mL portions of ethyl acetate, the combined extracts were dried over magnesium sulfate, and the solvent was removed to give 927 g (74%) ethyl trans-2,5-dimethyl-1-piperazinecarboxylate as a yellow oil.

A mixture of ethyl trans-2,5-dimethyl-1-piperazinecarboxylate (643 g, 3.45 mol), allyl bromide (328 mL, 3.80 mol), and sodium carbonate (440 g, 4.15 mol) in 2500 mL of acetonitrile was heated at reflux for 1.5 hours. The reaction was cooled to room temperature, filtered, and the solvent removed under vacuum. The residue was dissolved in 4000 mL of dichloromethane and washed with two 500 mL portions of 1M sodium hydroxide. The dichloromethane solution was dried over magnesium sulfate and the solvent was removed to give 630 g (81%) of ethyl trans-4-allyl-2,5-dimethyl-1-piperazinecarboxylate as an oil.

Ethyl trans-4-allyl-2,5-dimethyl-1-piperazinecarboxylate (630 g, 2.78 mol) was added to a solution of 87% potassium hydroxide pellets (2970 g, 46 mol) in 4300 mL of 95% ethanol and heated at reflux for 1.5 hours. Carbon dioxide evolution was observed for the first 0.5–1 hour of heating. The reaction was cooled below reflux temperature and 2000 mL of toluene was carefully added. Ethanol was removed by azeotropic distillation at 105° C. while adding an additional 4000 mL of toluene to the reaction flask during the course of the distillation. After collection of 9000 mL of distillate, the reaction was cooled to 5° C. and 1000 mL of toluene was carefully added. The solution was slowly cooled to 5° C. and maintained at 5° C. for 30 minutes. The solution was filtered, and the filter cake was washed with an additional 1500 mL of toluene. The filtrate was washed with 1000 mL of water, dried over magnesium sulfate, and the solvent was removed to give 296 g (69%) of trans-1-allyl-2,5-dimethylpiperazine as a dark liquid. NMR (300 MHz, DMSO-$d_6$): δ0.87 (d, J=6.3 Hz, 3H); 0.92 (d, J=6.3 Hz, 3H); 1.63 (t, J=11 Hz, 1H); 2.05 (m, 1H); 2.30 (t, J=11 Hz, 1H); 2.6–2.8 (m, 4H); 3.33 (dd, $J_1$=5 Hz, $J_2$=14Hz, 1H); 5.09 (d, J=8.7 Hz, 1H); 5.13 (d, J=14 Hz, 1H) 5.8 (m, 1H).

Di-p-toluoyl-D-tartaric acid (Schweizerhall, Inc., South Plainfield, N.J.) (1.25 Kg, 3.2 mol) was dissolved in hot (~60° C.) 95% ethanol (16 L) and racemic trans-1-allyl-2,5-dimethylpiperazine (500 g, 3.2 mol) was added in several portions (caution: exothermic). The hot solution was seeded with crystals of the diastereoisomerically pure salt (obtained from a previous small-scale resolution) and cooled to room temperature over 2–3 hours. The solution was slowly stirred for 2 days at room temperature. The resulting salt was collected by filtration, washed twice with 95% ethanol, and dried under vacuum to give 826.5 g of a white solid (47%). The process was repeated with a second batch of the di-p-toluoyl-D-tartaric acid and racemic trans-1-allyl-2,5-dimethylpiperazine to give 869 g (50%).

The total of 1695 g of salt was divided into three batches and each batch was recrystallized twice in the following fashion. The salt was dissolved in refluxing 95% ethanol (~2.7 L/100 g of salt), and approximately half of the ethanol was removed by distillation. (Note: vigorous stirring was necessary during distillation to prevent crystallization on the vessel wall.) The hot solution was seeded with crystals of the pure diastereomeric salt, cooled to room temperature, and stirred slowly for 2 days before collecting the salt by filtration. (Note: a subsequent experiment suggested that crystallization time can be reduced from 2 days to 8 hours.) The total amount recovered was 1151 g. The salt was dissolved in 3 L of 2M aqueous sodium hydroxide, and the aqueous solution was extracted with four 1 L portions of dichloromethane. The organic extracts were combined, dried over sodium sulfate, and solvent removed by rotary evaporation (temperature <20° C.) to give 293 g (29% based on racemic weight) of 2R.5S-1-allyl-2.5-dimethylpiperazine as a clear oil. $[\alpha]_D^{20}$=–55.1° (abs. ethanol, c=1.2). The trifluoroacetamide of the product was prepared with trifluoroacetic anhydride and analyzed by chiral capillary gas chromatography (Chiraldex B-PH column, 20 m×0.32 mm, Advanced Separation Technologies Inc., Whippany, N.J., 120° C.) indicating an enantiopurity of >99% ee (retention time of desired enantiomer, 11.7 min; other enantiomer, 10.7 min).

3-(3-((tert-Butyldimethylsilyl)oxy)-α-hydroxybenzyl)-N,N-diethylbenzamide (115.9 g, 0.280 mol) was dissolved in tetrahydrofuran (560 mL) and thionyl chloride (24.5 mL 0.336 mol) was added. The reaction was noticeably exothermic. The mixture was stirred for 15 minutes and concentrated in vacuo (cautiously at first, due to rapid gas evolution). After all volatiles were removed, the crude 3-(3-((tert-butyldimethylsilyl) oxy)-α-chlorobenzyl)-N,N-diethylbenzamide was dissolved in acetonitrile (560 mL). Sodium iodide (42 g, 0.280 mol), diisopropylethylamine (73 mL. 0.42 mol), and (2R.5S)-1-allyl-2.5-dimethylpiperazine (52.5 g, 0.280 mol) were added. The mixture was stirred at reflux, under nitrogen, for 2.5 hours. The acetonitrile was removed by distillation, under nitrogen, over the next hour. After cooling, the reaction mixture was poured into ethyl acetate (1.1 L) and potassium carbonate solution (350 mL of a 2M aqueous solution), and shaken. The organic phase was separated, dried over solid potassium carbonate, and concentrated in vacuo. The residue was dissolved in ethyl acetatepetroleum ether (1:1. 150 mL), and placed on a column of silica gel (3 kg). Elution with ethyl acetate-petroleum ether (1:1) afforded the desired isomer as the first of the two epimers to elute. The eluate solution was concentrated to a small volume and allowed to stand for 12 hours. A crystalline impurity that precipitated was removed by filtration, and the filtrate was concentrated to dryness.

The residue was dissolved in tetrahydrofuran-petroleum ether (1:1, 125 mL) and extracted with 350 mL of 0.75M hydrochloric acid. The aqueous phase, containing the desired product, was stirred at room temperature for 24 hours to cleave the silyl ether. The solution was then washed with 1:1 ethyl acetate-petroleum ether (2×100 mL). The aqueous solution was stirred with ethyl acetate (100 mL) while solid sodium bicarbonate (38 g) was added portionwise, with caution (vigorous gas evolution). After 15 minutes of additional stirring, the layers were separated and the aqueous layer extracted again with ethyl acetate (100 mL). The two ethyl acetate portions were combined, dried over sodium sulfate, concentrated in vacuo, and dried under high vacuum to yield 37.3 g (30%) of (+)-3-((αR)-α-((2S,5R)-4-allyl-2.5dimethyl-1-piperazinyl)-3-hydroxybenzyl)-N,N-diethylbenzamide as an off-white solid. $[\alpha]_D^{20}=+20°$ (methanol, c=2). NMR (400 MHz. DMSO-d$_6$): δ0.91 (d, J=6.2 Hz, 3H); 0.99 (br s, 3H); 1.05 (d, J=6.2 Hz, 3H); 1.09 (br s, 3H); 1.84 (dd, J$_1$=7.3 Hz, J$_2$=10.9 Hz, 1H); 2.06 (dd, J$_1$=7.3 Hz, J$_2$=10.9 Hz, 1H); 2.48 (m, 1H); 2.51 (dd, J$_1$=2.7 Hz, J$_2$=10.9 Hz, 1H); 2.58 (br s, 1H); 2.70 (dd, J$_1$=2.7 Hz, J$_2$=10.9 Hz, 1H); 2.81 (dd, J$_1$=7.0 Hz, J$_2$=13.9 Hz, 1H); 3.12 (br s, 2H); 3.15 (dd, J$_1$=5.1 Hz, J$_2$=13.9 Hz, 1H); 3.38 (br s, 2H); 4.97 (br s, 1H); 5.07 (d, J=10.2 Hz, 1H), 5.14 (d, J=16.9 Hz, 1H); 5.70–5.82 (m, 1H); 6.64 (dd, J$_1$=2.1 Hz, J$_2$=8.0 Hz, 1H); 6.65 (s, 1H); 6.68 (d, J=7.7 Hz, 1H); 7.11 (t, J=8.0 Hz, 1H); 7.14 (d, J=7.6 Hz, 1H); 7.30 (s, 1H); 7.33 (t, J=7.6 Hz, 1H); 7.39 (d, J=8.0 Hz, 1H); 9.31 (s, 1H). Mass spectrum (CI—$_4$) m/e: 436 (M+1, 53%). Calc. for C$_{27}$H$_{37}$N$_3$O$_2$ 0.5 H$_2$O: C, 72.94: H, 8.61: N, 9.45. Found: C, 73.00; H, 8.57; N, 9.40. The free amine (32.2 g) was dissolved in 200 mL of absolute ethanol and titrated with ethanolic hydrogen chloride (7M and 1M) to a pH of 3.95. The solvent was removed and the residue was redissolved in 50 mL of dichloromethane. Diethyl ether (900 mL) was added with vigorous stirring to precipitate a gummy product which solidified upon stirring overnight under nitrogen. The product was collected by filtration and dried under vacuum at 55° C. to give 33.06 g (91% recovery) of the monohydrochloride salt. Calc. for C$_{27}$H$_{37}$N$_3$O$_2$ HCl H$_2$O: C, 66.17; H,8.23; N, 8.57; Cl, 7.23. Found: C, 66.40; H,8.17; N, 8.48; Cl, 7.28.

EXAMPLE 2

(α)-3-((αR)-α-((2S,5R)-2,5-Dimethyl-1-piperazinyl)-3-hydroxybenzyl)-N,N-diethylbenzamide A mixture of (+)-3-((αR)-α-((2S,5R)-4-allyl-2,5-dimethyl-1-piperazinyl)-3-hydroxybenzyl)-N,N-diethylbenzamide monohydrochloride (8.22 g, 17.1 mmol. Example 1) and 5.45 g (2.5 mmol) of 5% palladium on charcoal in 160 ml of methanol:water/3:1 was heated at reflux for 20 hours. The reaction mixture was filtered through Celite under nitrogen and the filtrate was evaporated. The residue was diluted with water and the pH was adjusted to 8 with aqueous 1M sodium hydroxide. The mixture was extracted with ethyl acetate, dried over sodium sulfate, and evaporated to give 5.05 g (75%) of (+)-3-((αR)-α-((2S,5R)-2,5-dimethyl-1-piperazinyl)-3-hydroxybenzyl)-N,N-diethyl-benzamide as a light yellow solid. NMR (DMSO-d$_6$, 200 MHz): δ1.1 (m, 12H); 2.0 (m, 1H); 2.6–2.9 (m, 3H); 3.0–3.5 (m, 7H); 5.25 (s, 1H); 6.7 (m, 3H); 7.2 (m, 3H); 7.4 (m, 2H); 9.5 (s, 1H). $[\alpha]_D^{20}=+11.9°$ (abs ethanol, c=2.3). Titration of 0.20 g of product with ethanolic hydrogen chloride in ethanol solution to pH 3.5 and precipitation from dichloromethane with diethyl ether gave 0.103 g (47% recovery) of the monohydrochloride salt as an off-white solid. Calc. for C$_{24}$H$_{33}$N$_3$O$_2$ HCl 0.75 H$_2$O: C, 64.70; H, 8.03; N, 9.43; Cl, 7.96. Found: C, 64.97; H, 7.97; N, 9.38; Cl, 8.04. Mass spectrum (CI—CH$_4$) m/e 396 (M+1, 38%); 282 (39%); 115 (100%).

EXAMPLE 3

(+)-3-((αR)-α-((2S,5R)-2,5-Dimethyl-4-ethyl-1-piperazinyl)-3-hydroxy-benzyl)-N,N-diethylbenzamide A solution of (+)-3-((αR)-α-((2S,5R)-2.5-dimethyl-1-piperazinyl)-3-hydroxybenzyl)-N,N-diethylbenzamide (0.30 g, 0.76 mmol, Example 2) in 1.5 mL of 2M ethanolic hydrogen chloride was evaporated to dryness. The residue was dissolved in 7 mL of acetone:water (3:2). Sodium acetate trihydrate (0.28 g, 2.02 mmol), acetaldehyde (40 mL, 0.71 mmol) and sodium cyanoborohydride (0.072 g, 1.1 mmol) were added. After stirring at room temperature under nitrogen for 18 hours, the mixture was acidified with aqueous 6M hydrochloric acid to pH 2 and extracted with diethyl ether. The aqueous layer was adjusted to pH 8 with 10M aqueous sodium hydroxide. The resulting suspension was extracted with ethyl acetate, and the extracts were dried over sodium sulfate and evaporated to dryness to give 0.21 g of a yellow oil. Purification by thin layer chromatography on silica gel plates with dichloromethane:ethanol:ammonium hydroxide/90:10:1 gave 0.12 g (38%) of (+)-3-((αR)-α-((2S,5R)-2,5-dimethyl-4-ethyl-1-piperazinyl)-3-hydroxybenzyl)-N,N-diethylbenzamide as a light beige solid. NMR (DMSO-d$_6$, 300 MHz): δ0.9 (d, J=6 Hz, 3H); 1.1 (d, J=6 Hz, 3H); 1.0 (br m, 6H); 1.8 (m, 1H); 2.05 (dd, J$_1$=11 Hz, J$_2$=8 Hz, 1H); 2.25 (dd, J$_1$13 Hz, J$_2$=6 Hz, 1H); 2.6 (m, 4H); 2.7 (d, J=11 Hz, 1H); 3.1 (br m, 2H); 3.4 (br m, 2H); 5.0 (s, 1H); 6.65 (m, 3H); 7.1(d, J=8 Hz, 1H); 7.15 (d, J=8 Hz, 1H); 7.35 (m, 3H); 9.3 (s, 1H). $[\alpha]_D^{20}=+2.1°$ (abs ethanol, c=0.96). The product was dissolved in absolute ethanol and titrated to pH 3 with ethanolic hydrogen chloride, concentrated and treated with diethyl ether to precipitate 0.111 g (85% recovery) of the monohydrochloride salt as a white powder. Calc. for C$_{26}$H$_{37}$N$_3$O$_2$ HCl H$_2$O: C, 65.32; H, 8.43; N, 8.79; Cl, 7.42. Found: C, 65.23; H, 8.15; N, 8.82: Cl, 7.53.: Mass spectrum (CI—CH$_4$) m/e 424 (M+1, 100%); 423 (M, 20%); 282 (12%); 141 (14%).

EXAMPLE 4

(+)-3-((αR*)-α-((2S*,5R*)-2,5-Dimethyl-4-propyl-1-piperazinyl)-3-hydroxybenzyl)-N,N-diethylbenzamide (±)-3-((αR*)-α-((2S*,5R*)-4-Allyl-2,5-dimethyl-1-piperazinyl)-3-hydroxybenzyl)-N,N-diethylbenzamide, the racemate of Example 1, was prepared according to the procedure of Example 1 using racemic trans-N-allyl-2,5-dimethylpiperazine. The material was de-allylated by the procedure of Example 2 to give (±)-3-((αR*)-α-((2S*,5R*)-2,5-dimethyl-1-piperazinyl)-3-hydrozybenzyl)-N,N-diethylbenzamide (1.8 g, 4.6 mmol), which was treated with tert-butylchlorodimethylsilane (1.38 g, 9.2 mmol) and imidazole (0.78 g, 11.4 mmol) in dimethylformamide at room temperature under nitrogen overnight. The reaction mixture was poured into ice-water and extracted with diethyl ether. The ethereal layers were washed with water and brine, dried over sodium sulfate and the solvent was evaporated to give 1.61 g (69%) of the tert-butyldimethylsilyl ether as a beige solid. The product (0.30 g, 0.59 mmol) was alkylated with 1-iodopropane (63 mL, 0.65 mmol) and anhydrous sodium carbonate (0.31 g, 2.95 mmol) in tetrahydrofuran at reflux for 3 days. The solvent was evaporated and the residue was taken up in dichloromethane and filtered to remove the insoluble salts. The filtrate was evaporated to give 0.30 g of a dark yellow oil. The crude product was deprotected with tetraethylammonium fluoride dihydrate (0.15 g, 0.81 mmol) in acetonitrile at room temperature. The solvent was evaporated and the residue was taken up in aqueous 1M hydrochloric acid and extracted with diethyl ether. The aqueous layer was adjusted to pH 8 with aqueous sodium hydroxide and extracted with ethyl acetate. The ethyl acetate extracts were dried over sodium sulfate and evaporated to give 0.15 g (63%) of (±)-((αR*) -α-((2S*,5R*)-2,5-dimethyl-4-propyl-1-piperazinyl)-3-hydroxybenzyl)-N,N-diethyl-benzamide as a beige solid. NMR (DMSO-$d_6$, 200 MHz): δ0.8 (t, J=8 Hz, 3H); 0.9 (d, J=6 Hz, 3H); 1.05 (d, J=6 Hz, 3H); 1.0 (br m, 6H); 1.3 (m, 2H); 1.9 (m, 1H); 2.1 (m, 2H); 2.4–2.7 (m, 4H); 2.8 (d, J=10 Hz, 1H); 3.1 (br m, 2H); 3.4 (m, 2H); 5.0 (s, 1H); 6.7 (m, 3H); 7.1 (m, 2H); 7.4 (m, 3H); 9.35(s, 1H). The product was dissolved in ethanol and titrated to pH 3 with ethanolic hydrogen chloride to give 0.073 g (45%) of the monohydrochloride as a white powder. Calc. for $C_{27}H_{39}N_3O_2$HCl 0.75 $H_2O$; C, 66.51; H, 8.58; N, 8.62; Cl, 7.27. Found: C, 66.32; H, 8.49; N, 8.58; Cl, 7.32. Mass spectrum (CI—$CH_4$) m/e: 438 (M+1, 76%).

EXAMPLE 5

(–)-3-((αR)-α-((2S,5R)-2,5-Dimethyl-4-(2-propynyl)-1-piperazinyl)-3-hydroxybenzyl)-N,N-diethylbenzamide was prepared by alkylation of the compound of Example 2 with propargyl bromide and deprotected by methods similar to that in Example 4. NMR (DMSO-$d_6$, 200 MHz): δ0.9 (d, J=6 Hz, 3H); 1.05 (d, J=6 Hz, 3H); 1.1 (br m, 6H); 1.75 (m, 1H); 2.3–2.7 (m, 5H); 3.1–3.5 (m, 7H); 5.25 (s, 1H); 6.7 (m, 3H); 7.1–7.5 (m, 5H); 9.4 (s, 1H). $[α]_D^{20}$=–12.9° (absolute ethanol, c=1.0). Calc. for $C_{27}H_{35}N_3O_2$ HCl 0.75 $H_2O$: C 67.06; H, 7.82; N, 8.69; Cl, 7.33. Found: C, 66.87; H, 7.78; N, 8.65; Cl, 7.35. Mass spectrum (CI—$CH_4$) m/e: 434 (M+1, 100%): 433 (M, 13%); 282 (28%); 151 (42%).

EXAMPLE 6

(±)-3-((αR*)-α-((2S*,5R*)-2,5-Dimethyl-4-phenethyl-1-piperazinyl)-3-hydroxybenzyl)-N,N-diethylbenzamide was prepared according to the procedure of Example 4 with phenethyl bromide. NMR (DMSO-$d_6$, 200 MHz): δ0.8–1.2 (m, 12H); 1.9 (m, 1H): 2.0–3.0 (m, 9H); 3.1 (br m, 2H); 3.3 (br m, 2H) 5.0 (s, 1H); 6.7 (m, 3H); 7.1–7.5 (m, 10H); 9.4 (s, 1H). Calc. for $C_{32}H_{41}N_3O_2$ HCl 0.75 $H_2O$: C, 69.92; H, 7.98; N, 7.64: Cl, 6.45. Found: C, 69.65; H, 7.94; N, 7.62; Cl, 6.45. Mass spectrum (CI—$CH_4$) m/e: 500 (M+1. 25%); 282 (14%); 284 (100%); 217 (84%).

EXAMPLE 7

(+)-3-((αR)-α-((2S,5R)-2,4,5-Trimethyl-1-piperazinyl)-3-hydroxybenzyl)-N,N-diethylbenzamide (+)-3-((αR)-α-((2S,5R)-2,5-Dimethyl-1-piperazinyl)-3-hydroxybenzyl)-N,N-diethylbenzamide (Example 2, 1.00 g, 2.53 mmol) was combined with 0.4 mL (10.1 mmol) of 96% formic acid and 0.56 mL (7.6 mmol) of 37% aqueous formaldehyde. The mixture was kept at 80° C. for 18 hours, cooled to room temperature, treated with 6 mL of aqueous 6M hydrochloric acid and extracted with diethyl ether. The aqueous layer was diluted with water and adjusted to pH 8 with aqueous 10M sodium hydroxide. The resulting slurry was extracted with dichloromethane. The combined organic layers were dried over sodium sulfate and evaporated to give 1.12 g of a beige solid. Chromatography on silica gel with dichloromethane:ethanol (1 to 7%) gave 0.62 g (60%) of (+)-3-((αR)-α-((2S,5R)-2,4,5-trimethyl-1-piperazinyl)-3-hydroxybenzyl)-N,N-di-ethylbenzamide as an off-white solid. NMR (DMSO-$d_6$ 200 MHz): δ0.9 (d, J=6 Hz, 3H): 1.05 (d, J=6 Hz, 3H); 1.0 (br m, 6H); 1.75 (t, J=9 Hz, 1H); 2.0 (t, J=10 Hz,1H); 2.1 (s, 3H); 2.1 (m, 1H); 2.5 (m, 2H); 2.7 (d, J=9 Hz, 1H); 3.2 (br m, 2H); 3.4 (br m, 2H) 5.2 (s, 1H); 6.7 (m, 3H); 7.2 (m, 2H); 7.3 (s, 1H); 7.4 (m, 3H); 9.4 (s, 1H). $[α]_D^{20}$=+17.7° (absolute ethanol, c=2.2). The product was titrated to pH 3 with ethanolic hydrogen chloride to give 0.503 g (74% recovery) of the monohydrochloride salt as a white powder. Calc. for $C_{25}H_{35}N_3O_2$ HCl 0.75 $H_2O$: C, 65.34; H, 8.22; N, 9.14; Cl, 7.71. Found: C. 65.07; H. 8.16; N. 9.07; Cl, 7.70. Mass spectrum (CI—$CH_4$) m/e: 410 (M+1, 100%).

EXAMPLE 8

(–)-3-((αR)-α-((2S,5R)-4-(Cyclopropylmethyl)-2.5-dimethyl-1-piperazinyl)-3-hydroxybenzyl)-N N-diethylbenzamide was prepared by alkylation of the compound of Example 2with (bromomethyl)-cyclopropane by the method in Example 4. NMR (DMSO-$d_6$, 200 MHz); δ0.05 (m, 2H); 0.4 (d, J=8 Hz, 2H); 0.8 (m, 1H); 0.9(d, J=6 Hz, 3H); 1.1 (d, J=6 Hz, 3H); 1.1 (br m, 6H); 1.8 (dd, $J_1$=11 Hz, $J_2$=9 Hz, 1H); 2.2 (m, 2H); 2.4 (dd, $J_1$=13 Hz, $J_2$=8 Hz, 1H); 2.6 (m, 3H); 2.9 (d, J=9 Hz, 1H); 3.2 (br m, 2H); 3.4 (br m, 2H); 2H); 5.0 (s, 1H); 6.7 (m, 3H); 7.1 (m, 2H); 7.4 (m, 3H); 9.4 (s, 1H). $[α]_D^{20}$=–0.9° (absolute ethanol, c=2.9). Calc. for $C_{28}H_{39}N_3O_2$ HCl 0.75 $H_2O$: C, 67.31; H, 8.37; N, 8.41; Cl, 7.10 Found: C, 67.34; H, 8.39; N, 8.42; Cl, 7.15. Mass spectrum (CI—$CH_4$) m/e 450 (M+1, 100%), 449 (M, 28%), 282 (20%), 167 (35%).

EXAMPLE 9

(+)-3-((αR)-α-((2S,5R)-4-Allyl-2.5dimethyl-1-piperazinyl)-3-hydroxybenzyl)-N-methyl-N-phenylbenzamide A mixture of 1400 g (8.1 mol) of 3-bromophenol, 1218 g (8.1 mol) of tertbutylchlorodimethylsilane and 1376 g (20.2 mol) of imidazole in 1600 mL of N,N-dimethylformamide was stirred at room temperature under nitrogen for 18 hours. The reaction mixture was poured into pH 8 aqueous buffer solution and extracted with diethyl ether. The ether extracts were washed with water and brine, dried over sodium sulfate, and the solvent was evaporated under vacuum to give 2314 g of crude 3-bromophenyl tert-butyldimethylsilyl ether as an orange oil. NMR ($CDCl_3$, 200 MHz) δ:0.2 (s, 6H); 0.95 (s, 9H); 6.8 (m, 1H); 7.0–7.1 (m, 3H).

The silyl ether (1771 g, 6.17 mol) was dissolved in 4 L of dry tetrahydrofuran, dried further over molecular sieves, then transferred to a 12 L reaction flask under nitrogen and cooled to –78° C. n-Butyllithium (2400 mL of a 1.6M solution in hexane) was added, while stirring under nitrogen, at a rate to keep the temperature below –70° C. Stirring was continued at –78° C. for 2 hours. A solution of 3-bromobenzaldehyde (1119 g, 6.05 mol) in 600 mL of dry tetrahydrofuran was added at a rate to keep the reaction temperature below –70° C. After stirring for 2 hours at –78° C., the reaction was quenched with 1400 mL of saturated aqueous ammonium chloride and allowed to warm to room temperature. The mixture was filtered to remove solids and the layers were separated. The organic phase was washed with brine, dried over sodium sulfate and evaporated to give 2500 g of crude α-(3-bromophenyl)-3-(tert-butyldimethylsilyoxy)-benzyl alcohol as a yellow oil. Chromatography on silica gel of 1 kg of the crude product with hexane:dichloromethane (gradient from 90:10 to 75:25, followed by dichloromethane:ethyl acetate/90:10) gave 692.3 g of α-(3-bromophenyl)-3-(tert-butyldimethylsilyloxy)benzyl alcohol as a yellow oil. NMR ($CDCl_3$, 200 MHz) δ: 0.2 (s, 6H); 0.95 (s, 9H); 2.3 (br s, 1H); 5.7 (s, 1H); 6.75 (d, J=8 Hz, 1H); 6.8 (s, 1H); 6.9 (d, J=8 Hz, 1H); 7.2 (m, 2H); 7.3 (d, J=8 Hz, 1H); 7.4 (d, J=8 Hz, 1H); 7.5 (s, 1H).

Thionyl chloride (38 mL, 0.51 mol) was added dropwise to a solution of the benzhydryl alcohol (160 g, 0.41 mol) in 1 L of dichloromethane and the mixture was stirred overnight at room temperature. The solvent was removed under vacuum, the residue was redissolved in toluene, and the solvent was again removed under vacuum to eliminate excess thionyl chloride to give crude α-(3-bromophenyl)-3-(tert-butyldimethylsilyloxy)benzyl chloride as a brown oil. NMR (CDCl$_3$, 200 MHz) δ: 0.2 (s, 6H); 0.95 (s, 9H); 6.0 (s, 1H); 6.8–7.0 (m, 3H); 7.2–7.6 (m, 5H).

A mixture of the benzhydryl chloride and (−)-(2R,5S)-1-allyl-2,5-dimethylpiperazine (137.6 g, 0.89 mol, from Example 1, infra) in 1500 mL of acetonitrile was heated at reflux for 48 hours, concentrated in vacuo, and the residue dissolved in ethyl acetate. The mixture was washed with 0.25M aqueous sodium hydroxide, dried over sodium sulfate and concentrated in vacuo to give 202.6 g of dark oil, which was dissolved in acetonitrile (1 L) and treated with tetraethylammonium fluoride dihydrate (88.9 g, 0.48 mol). After stirring at room temperature overnight, the solvent was removed under vacuum. The residue was dissolved in dichloromethane (2 L), washed with pH 8 aqueous buffer solution, dried over sodium sulfate and concentrated down to a dark oil which was stirred in acetonitrile (700 mL) at 25° C. for 72 hours to produce a tan precipitate. Recrystallization from acetonitrile (2 L) gave 35.3 g of a single diastereomer: (+)-3-((αR)-α-((2S,5R) -4-allyl-2,5-dimethyl-1-piperazinyl)-3-bromobenzyl)phenol as a white solid. NMR (DMSO-d$_6$, 200 MHz) δ: 0.95 (d, J=6 Hz, 3H); 1.03 (d, J=6 Hz, 3H); 1.8 (dd, J$_1$=6 Hz, J$_2$=10 Hz, 1H); 2.1 (dd, J$_1$=6 Hz, J$_2$=10 Hz, 1H); 2.4–2.6 (m, 3H); 2.7 (d, J=11 Hz, 1H); 2.8 (dd, J$_1$=7 Hz, J$_2$=14 Hz, 1H); 3.2 (dd, J$_1$=6 Hz, J$_2$=13 Hz, 1H); 4.9 (s, 1H); 5.1 (d, J=10 Hz, 1H); 5.2 (d, J=18 Hz, 1H); 5.7–5.9 (m, 1H); 6.6–6.8 (m, 3H); 7.0–7.4 (m, 4H); 7.55 (s, 1H); 9.35 (s, 1H). The mother liquor was evaporated to give 127 g of a brown solid. A portion (11 g) of this solid was purified by chromatography on silica gel with dichloromethane:ethanol (0–2.5%). The first isomer to elute from the column was collected to give 2.32 g of 3-((αS)-α-((2S, 5R)-4-allyl-2,5-dimethyl-1-piperazinyl)-3-bromo-benzyl)phenol as a light yellow solid. NMR (DMSO-d$_6$, 200 MHz) δ: 0.95 (d, J=6 Hz, 3H); 1.05 (d, J=6 Hz, 3H); 1.85 (dd, J$_1$=7 Hz, J$_1$=9 Hz, 1H); 2.1(dd, J$_1$=6 Hz, J$_2$=9 Hz, 1H); 2.5 (m, 3H); 2.7 (dd, J$_1$=2 Hz, J$_2$=8 Hz, 1H); 2.9 (dd, J$_1$=7 Hz, J$_2$=7 Hz, 1H); 3.1 (dd, J$_1$=5 Hz, J$_2$=9 Hz, 1H); 4.95 (s, 1H); 5.1 (d, J=10 Hz, 1H); 5.2 (d, J=17 Hz, 1H); 5.8 (m, 1H); 6.6 (d, J=8 Hz, 1H); 6.8 (m, 2H); 7.1 (t, J=8 Hz, 1H); 7.3 (m, 2H); 7.5 (m, 2H); 9.3 (s, 1H).

(+)-3-((αR)-α-((2S,5R)-4-Allyl-2,5-dimethyl-1-piperazinyl)-3-bromobenzyl)phenol (147.3 g, 0.355 mol) was dissolved in 1 L of N-methyl-2-pyrrolidinone with cuprous cyanide (63.6 g, 0.71 mol), and the reaction was heated at 170° C. for 30 hours. The reaction was cooled to room temperature and poured into 7 L of aqueous 14% sodium cyanide. The mixture was stirred overnight and extracted with ethyl acetate. The ethyl acetate extracts were combined, washed with water, dried over sodium sulfate and concentrated in vacuo to give 133.3 g of a brown solid. Chromatography on silica gel with ethanol (2–7%) in dichloromethane gave 97.8 g of crude (+)-3-((αR)-α-((2S,5R)-4-allyl-2,5-dimethyl-1-piperazinyl)-3-hydroxybenzyl)benzonitrile. Recrystallization from acetonitrile gave 74.2 g (58%) pure (+)-3-((αR)-α-((2S,5R)-4-allyl-2,5-dimethyl-1-piperazinyl)-3-hydroxybenzyl)benzonitrile as a white solid.

The benzonitrile (78.8 g, 0.22 mol) was combined with 60 g of sodium hydroxide pellets in 1 L of 95% ethanol and heated at reflux for 72 hours. The mixture was concentrated in vacuo to remove ethanol. The residue was dissolved in water and the resulting solution was adjusted to pH 5 with concentrated hydrochloric acid. The solvent was removed in vacuo to give 138.8 g of the 3-((αR)-α-((2S,5R)-4-allyl-2,5-dimethyl-1-piperazinyl)-3-hydroxybenzyl)benzoic acid as a mixture with sodium chloride. A portion (5.0 g) of the crude acid was stirred with 50 mL of water. The resulting slurry was filtered, the solid in the filter was washed three times with water then dried under vacuum for three hours to give 2.02 g of (+)-3-((αR)-α-((2S,5R)-4-allyl-2,5-dimethyl-1-piperazinyl)-3-hydroxybenzyl)benzoic acid as a light beige solid. NMR (DMSO-d$_6$, 200 MHz) δ: 0.95 (d, J=6 Hz, 3H); 1.1 (d, J=6 Hz, 3H); 1.9 (ddd, J$_1$=3 Hz, J$_2$=7 Hz, J$_3$=10 Hz, 1H); 2.1 (dd, J$_1$=8 Hz, J$_2$=10 Hz, 1H); 2.5 (m, 2H); 2.7–2.9 (m, 2H); 3.2 (m, 2H); 5.05 (d, J=12 Hz, 1H); 5.2 (d, J=18 Hz, 1H); 5.8 (m, 1H); 6.7 (m, 3H); 7.1 (t, J=8 Hz, 1H); 7.4 (t, J=8 Hz, 1H); 7.65 (d, J=8 Hz, 1H); 7.8 (d, J=8 Hz, 1H); 8.0 (s, 1H); 9.4 (s, 1H). [α]$_D^{20}$=+4.1° (0.1M aqueous sodium hydroxide, c=1.09). Calc. for C$_{23}$H$_{28}$N$_2$O$_3$ 0.75 H$_2$O: C, 70.12; H, 7.55; N, 7.11. Found: C, 70.23; H, 7.35; N, 7.10. Mass spectrum (CI—CH$_4$) m/e: 381 M+1. 35%); 380(M, 2%); 227(28%);155 (100%); 153 (83%).

3-((αR)-α-((2S,5R)-4-Allyl-2,5-dimethyl-1-piperazinyl)-3-hydroxybenzyl)benzoic acid (25.9 g of a 50% by weight mixture with sodium chloride, 34.0 mmol) was dissolved in 40 mL of dimethylformamide with 12.8 g (84.9 mmol) of tert-butylchlorodimethylsilane and 11.5 g (169.1 mmol) of imidazole and stirred overnight at room temperature. The reaction solution was poured into 500 mL of ice water and extracted with 500 mL of diethyl ether. The ether extract was washed twice with 250 mL of water, and then with 125 mL of saturated sodium chloride solution. The ether solution was dried over sodium sulfate and the solvent was removed to give 20.8 g of crude tert-butyldimethylsilyl 3-((αR)-α-((2S,5R)-4-allyl-2,5-dimethyl-1-piperazinyl)-3-(tert-butyldimethylsilyloxy)benzyl)-benzoate.

The crude silyl ether-silyl ester (20.7 g, ≦33.9 mmol based on the previous reaction) was dissolved in 60 mL of dichloromethane and cooled to 0° C. under nitrogen. Oxalyl chloride (3.7 mL. 42.4 mmol) was added dropwise. While maintaining the bath temperature at 0° C., catalytic dimethylformamide (10 drops) was added slowly. Evolution of gas was evident during the addition of dimethylformamide. The bath temperature was maintained at 0° C. for 30 minutes, then allowed to warm to room temperature. The solution was stirred at room temperature, under nitrogen for 24 hours. All of the volatiles were removed by evaporation under reduced pressure to give 29.76 g of crude 3-((αR)-α-((2S,5R)-4-allyl-2,5-dimethyl-1-piperazinyl)-3-(tert-butyldimethylsilyloxy)benzyl)benzoyl chloride as a yellow-brown solid. The crude acid chloride was used without purification.

Benzamide-Formation Method 3-((αR)-α-((2S,5R)-4-Allyl-2,5-dimethyl-1-piperazinyl)-3-(tert-butyldimethylsilyloxy)benzyl)benzoyl chloride (2.33 g crude, approx-imately 1.44 g. actual compound, 2.81 mmol based on 3-((αR)-α-((2S,5R)-4-allyl-2,5-dimethyl-1-piperazinyl)-3 -hydroxybenzyl)benzoic acid) was dissolved in 12 mL of dichloromethane at room temperature under nitrogen. Triethylamine (0.5 mL) was added to the solution. N-methylaniline (0.46 mL, 4.3 mmol) was added dropwise to the solution (exothermic), and the reaction was stirred overnight at room temperature. All volatiles were removed by evaporation under reduced pressure to provide a gummy brown solid.

This crude solid was dissolved in acetonitrile (8 mL) under nitrogen at room temperature. Tetraethylammonium fluoride hydrate (1.19 g, 6.42 mmol) was added and the solution was stirred for 1 hour at room temperature. After removal of solvent, the residue was purified by chromatography on silica gel (4 cm×12 cm) with 0.5–2% ethanol in dichloromethane to give 0.368 g (28% over 4 steps from 3-((αR)-α-((2S,5R)-4-allyl-2,5-dimethyl-1-piperazinyl)-3- hydroxybenzyl)benzoic acid) of (+)-3-((αR)-α-((2S,5R)-4-allyl-2,5-dimethyl-1-piperazinyl)-3-(hydroxybenzyl)-N-methyl-N-phenylbenzamide as a light yellow solid. NMR (300 MHz, DMSO-$d_6$): δ0.89 (d, J=6.0 Hz, 3H); 0.96 (d, J=6.0 Hz, 3H); 1.66 (dd, $J_1$=7.3 Hz, $J_2$=11.4 Hz, 1H); 2.01 (dd, $J_1$=7.8 Hz, $J_2$=10.6 Hz, 1H); 2.26 (br d, J=10.6 Hz, 1H); 2.37–2.54 (m, 2H); 2.66 (br d, J=11.0 Hz, 1H); 2.82 (dd, $J_1$=7.0 Hz, $J_2$=13.9 Hz, 1H); 3.17 (dd, $J_1$=4.8 Hz, $J_2$=13.9 Hz, 1H); 3.34 (s, 3H); 4.77 (s, 1H); 5.10 (d, J=10.1 Hz, 1H); 5.16 (d, J=17.3 Hz, 1H); 5.70–5.82 (m, 1H); 6.41 (d, J=7.4 Hz, 1H); 6.54 (s, 1H); 6.64 (d, J=8.0 Hz, 1H); 7.05–7.26 (m, 10H); 9.31 (s, 1H). Mass spectrum (CI—$CH_4$) m/e: 470 (M+1, 100%), 376 (81%), 316 (45%), 153 (97%). $[α]_D^{20}$=+12.3° (ethanol, c=1.2). The free amine (0.339 g) was dissolved in ethanol and titrated with ethanolic hydrogen chloride to pH 3.0 followed by precipitation with diethyl ether from dichloromethane to give 0.321 g (88% recovery) of the monohydrochloride salt as a hygroscopic light yellow powder. Calc. for $C_{30}H_{35}N_3O_2$ HCl $H_2O$: C, 68.75; H, 7.31; N, 8.02; Cl, 6.76. Found: C, 68.86; H, 7.42; N, 8.00; Cl, 6.84.

EXAMPLE 10

(+)-3-((αR)-α-((2S,5R)-4-Allyl-2,5-dimethyl-1-piperazinyl)-3-hydroxybenzyl)-N-(4-fluorophenyl)-N-methylbenzamide Following a general literature procedure for reductive alkylation (Krishnamurthy, S. *Tetrahedron Lett.* 1982, 23, 3315) acetic-formic anhydride was prepared by slowly adding formic acid (7.5 mL) to acetic anhydride at 0° C. After stirring for 5 minutes at 0° C., the mixture was heated at 55° C. for 1.75 hours under nitrogen. The mixture was cooled to 0° C. and used without purification. 4-Fluoroaniline (3.1 mL, 32.8 mmol) in tetrahydrofuran (10 mL) was added to acetic-formic anhydride (12.5 mL, 88 mmol) at 0° C. The reaction was stirred for 25 minutes and the volatiles were removed under vacuum to provide the formamide as a brown solid. A portion of the crude solid (2.39 g, 17.2 mmol) was dissolved in tetrahydrofuran (8 mL) and cooled to 0° C. Borane in tetrahydrofuran (40 mL of a 1.0M solution) was added dropwise. Gas evolution was evident during the first half of the addition. After the addition, the solution was heated to reflux for 3 hours. The solution was cooled to 0° C. and methanol (10 mL) was added carefully. After stirring for 10 minutes, ethanolic hydrogen chloride (7 mL of a 7.1M solution) was added and the reaction was stirred overnight. After removal of all volatiles in vacuo, crude N-methyl-4-fluoroaniline was obtained as a light purple solid. NMR (200 MHz, DMSO-$d_6$): δ2.65 (s, 3H); 5.54 (s, 1H); 6.51 (dd, $J_1$=4.7 Hz, $J_2$=8.8 Hz, 2H); 6.93 (dd, $J_1$=8.9 Hz, $J_2$=8.8 Hz, 2H).

3-((αR)-α-((2S,5R)-4-Allyl-2,5-dimethyl-1-piperazinyl)-3-tert-butyldimethylsilyloxy)benzyl)benzoyl chloride (Example 9, infra, 2.08 g. crude, approximately 1.29 g actual compound. 2.51 mmol based on 3-((αR)-α-((2S,5R)-4-allyl-2,5-dimethyl-1-piperazinyl)-3-hydroxybenzyl)-benzoic acid) was dissolved on 8 mL of dichloromethane at room temperature under nitrogen. Triethylamine (0.5 mL) was added to the solution. Then 4-fluoro-N-methylaniline (0.478 mg, 3.82 mmol) in dichloromethane (5 mL) was added dropwise to the solution (exothermic), and the reaction was stirred overnight at room temperature. All volatiles were removed by evaporation under reduced pressure to provide a gummy yellow-brown solid.

The crude solid was dissolved in acetonitrile (8 mL) under nitrogen at room temperature. Tetraethylammonium fluoride hydrate (1.06 g, 5.7 mmol) was added and the solution was stirred overnight at room temperature. After removal of solvent, the residue was purified by chromatography on silica gel (4 cm×14 cm) with 0.25–3.5% ethanol in dichloromethane to give 0.419 g (34% over 4 steps from 3-((αR)-α-((2S,5R)-4-allyl-2,5-dimethyl-1-piperazinyl)-3-hydroxybenzyl)benzoic acid) of (+)-3-((αR)-α-((2S,5R)-4-allyl-2,5-dimethyl-1-piperazinyl)-3-hydroxybenzyl)-N-(4-fluorophenyl)-N-methyl-benzamide as a yellow powder. NMR (300 MHz, DMSO-$d_6$): δ0.88 (d, J=6.0 Hz,3H); 0.96 (d, J=6.0 Hz, 3H); 1.68 (dd, $J_1$=7.7 Hz, $J_2$=10.8 Hz, 1H); 2.02 (dd, $J_1$=7.1 Hz, $J_2$=10.7 Hz, 1H); 2.28 (br d, J=10.7 Hz, 1H); 2.35–2.52 (m, 2H); 2.66 (br d, J=10.6 Hz, 1H); 2.82 (dd, $J_1$=7.4 Hz, $J_2$=13.9 Hz, 1H); 3.16 (dd, $J_1$=4.6 Hz, $J_2$=14.0 Hz, 1H); 3.32 (s, 3H); 4.77 (s, 1H); 5.10 (d, J=10.3 Hz, 1H); 5.16 (d, J=17.3 Hz, 1H); 5.70–5.84 (m, 1H); 6.43 (d, J=7.4 Hz, 1H); 6.56 (s, 1H); 6.64 (d, J=8.0 Hz, 1H); 7.02–7.22 (m, 9H); 9.31 (s, 1H). Mass spectrum (CI—$CH_4$) m/e: 4.88 (M+1,100%). 334 (11%), 153 (68%). $[α]_D^{20}$=+6.9° (ethanol, c=1.6). The free amine (0.390 g) was dissolved in ethanol and titrated with ethanolic hydrogen chloride to pH 3.3 followed by precipitation with diethyl ether from dichloromethane to give 0.327 g (78% recovery) of the monohydrochloride salt as a hygroscopic light yellow powder. Calc. for $C_{30}H_{34}N_3F$ HCl $H_2O$: 66.47; H, 6.88; N, 7.75; F, 3.50; Cl, 6.54. Found: C, 66.36; H, 6.74; N. 7.82; F, 3.27; Cl, 6.62.

EXAMPLE 11

(+)-3-((αR)-α-((2S,5R)-4-Allyl-2,5-dimethyl-1-piperazinyl)-3-hydroxybenzyl)-N-(4-chlorophenyl)-N-methylbenzamide 4-Chloro-N-methylaniline was prepared from 4-chloroaniline, coupled with 3-((αR)-α-((2S,5R)-4-allyl-2,5-dimethyl-1-piperazinyl)-3-(tert-butyldimethylsilyloxy)benzyl)-benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-(4-chlorophenyl)-N-methylbenzamide as a light yellow powder. NMR (300 MHz, DMSO-$d_6$): δ0.89 (d, J=6.2 Hz, 3H); 0.96 (d, J=6.1 Hz, 3H); 1.65 (dd, $J_1$=7.6 Hz, $J_2$=10.8 Hz, 1H); 2.01 (dd, $J_1$=7.6 Hz, $J_2$=10.4 Hz, 1H); 2.27 (dd, $J_1$=1.5 Hz, $J_2$=11.4 Hz, 1H); 2.35–2.52 (m, 2H); 2.65 (br d, J=10.8 Hz, 1H); 2.82 (dd, $J_1$=7.6 Hz, $J_2$=13.5 Hz, 1H); 3.16 (dd, $J_1$=4.5 Hz, $J_2$=14.6 Hz, 1H); 3.33 (s, 3H); 4.77 (s,1H); 5.10 (d, J=10.2 Hz, 1H); 5.16 (d, J=17.2 Hz, 1H); 5.70–5.86 (m, 1H); 6.42 (d, J=8.1 Hz, 1H); 6.56 (s, 1H); 6.64 (d, J=7.5 Hz, 1H); 7.04–7.25 (m, 5H); 7.13 (d, J=8.5 Hz, 2H); 7.29 (d, J=8.5 Hz, 2H); 9.31 (s, 1H). Mass spectrum (CI—$CH_4$) m/e: 504 ($^{35}$Cl, M+1, 86%), 350 (28%), 153 (100%). $[α]_D^{20}$=+10.2° (ethanol, c=1.6). The monohydrochloride salt was prepared as in Example 10 to give a hygroscopic light-yellow powder. Calc. for $C_{30}H_{34}N_3O_2Cl$ HCl 0.75$H_2O$: C, 65.04; H, 6.64; N, 7.58; Cl, 12.80. Found: C, 65.04; H, 6.71; N, 7.49; Cl, 12.83.

EXAMPLE 12

(+)-3-((αR)-α-((2S,5R)-4-Allyl-2,5-dimethyl-1-piperazinyl)-3-hydroxybenzyl)-N-ethyl-N-phenylbenzamide 3-((αR)-α-((2S,5R)-4-Allyl-2,5-dimethyl-1-piperazinyl)-3-(tert-butyldimethylsilyloxy)benzyl)benzoyl chloride (Example 9, infra, 2.81 g crude, approximately 1.74 g. actual compound, 3.39 mmol based on 3-((αR)-α-((2S,5R)-4-allyl-2,5-dimethyl-1-piperazinyl)-3-hydroxybenzyl)benzoic acid) was dissolved in 10 mL of dichloromethane at room temperature under nitrogen. Triethylamine (0.5 mL) was added to the solution. Then N-ethylaniline (0.780 mL, 6.2 mmol) was added dropwise to the solution (exothermic), and the reaction was stirred overnight at room temperature. All volatiles were removed by evaporation under reduced pressure to provide a thick brown oil.

The crude oil was dissolved in acetonitrile (10 mL) under nitrogen at room temperature. Tetraethylammonium fluoride hydrate (1.5 g, 8.1 mmol) was added and the solution was stirred for 1 hour at room temperature. After removal of solvent, the residue was purified by chromatography on silica gel (4 cm×15 cm) with 0.5–3% ethanol in dichloromethane to give 0.508 g (31% over 4 steps from 3-((αR)-α-((2S,5R)-4-allyl-2,5-dimethyl-1-piperazinyl)-3-hydroxybenzyl)benzoic acid) of (+)-3-((αR)-α-((2S,5R)-4-allyl-2,5-dimethyl-1-piperazinyl)-3-hydroxybenzyl)-N-ethyl-N-phenylbenzamide as a white solid. NMR (300 MHz, DMSO-$d_6$): δ0.89 (d, J=6.1 Hz, 3H); 0.96 (d, J=6.1 Hz, 3H); 1.07 (t, J=7.0 Hz, 3H); 1.67 (dd, $J_1$=7.4 Hz, $J_2$=10.4 Hz, 1H); 2.02 (dd, $J_1$=7.4 Hz, $J_2$=10.6 Hz, 1H); 2.27 (dd, $J_1$=1.4 Hz, $J_2$=10.6 Hz, 1H); 2.36–2.52 (m, 2H); 2.66 (br d, J=10.4 Hz, 1H); 2.82 (dd, $J_1$=7.8 Hz, $J_2$=13.5 Hz, 1H); 3.16 (dd, $J_1$=4.0 Hz, $J_2$=13.9 Hz, 1H); 3.83 (q, J=7.0 Hz, 2H); 4.75 (s, 1H); 5.09 (d, J=9.9 Hz, 1H); 5.16 (d, J=17.2 Hz, 1H); 5.70–5.84 (m, 1H); 6.41 (d, J=7.6 Hz, 1H); 6.54 (s, 1H); 6.63 (d, J=8.2 Hz, 1H); 7.03–7.29 (m, 10H); 9.30 (s, 1H). Mass spectrum (CI—$CH_4$) m/e: 484 (M+1,100%), 330 (57%), 153 (66%). $[\alpha]_D^{20}$=+10.4° (ethanol, c=1.2). The monohydrochloride salt was prepared from 0.473 g of the free amine as in Example 10 to give 0.389 g (76% recovery) of a hygroscopic white powder. Calc. for $C_{27}H_{37}N_3O_2$ HCl $H_2O$: C, 69.19; H, 7.49; N, 7.81; Cl, 6.59. Found: C, 69.41; H, 7.52; N, 7.73; Cl, 6.48.

EXAMPLE 13

(−)-3-((αR)-α-((2S,5R)-4-Allyl-2,5-dimethyl-1-piperazinyl)-3-hydroxybenzyl)-N-phenylbenzamide This compound was obtained as a light yellow powder from aniline and 3-((αR)-α-((2S,5R)-4-allyl-2,5-dimethyl-1-piperazinyl)-3-(t-butyl-dimethylsilyloxy)benzyl)benzoyl chloride (Example 9, infra) using the Benzamide-Formation Method described in Example 9. NMR (200 MHz, DMSO-$d_6$): δ0.99 (d,J=5.7 Hz, 3H); 1.10 (d, =5.7 Hz, 3H); 1.91 (dd, $J_1$=7.0 Hz, $J_2$=10.5 Hz, 1H); 2.14 (dd, $J_1$=6.0 Hz, $J_2$=10.4 Hz, 1H); 2.51–2.81 (m, 4H); 2.88 (dd, $J_1$=6.8 Hz, $J_2$=13.9 Hz, 1H); 3.18 (dd, $J_1$=5.4 Hz, $J_2$=13.8 Hz, 1H); 5.06 (d, J=15.6 Hz, 1H); 5.14 (s, 1H); 5.19 (d, J=18.1 Hz, 1H); 5.75 (m, 1H); 6.73 (m, 3H); 7.10 (d, J=7.8 Hz, 1H); 7.17 (d, J=8.0 Hz, 1H); 7.30–7.59 (m, 3H); 7.65 (d, J=7.6 Hz, 1H); 7.71–7.83 (m, 3H); 7.93 (s, 1H); 9.37(s, 1H); 10.21 (s, 1H). Mass spectrum (CI—$CH_4$) m/e: 456 (M+1,100%), 302 (41%), 153 (77%). $[\alpha]_D^{20}$=−4.44° (ethanol, c=1.4). The monohydrochloride salt was prepared as in Example 9 to give a hygroscopic light yellow powder. Calc. for $C_{29}H_{33}N_3O_2$ HCl 0.75 $H_2O$: C, 68.90 H, 7.08; N, 8.31; Cl, 7.01. Found: C, 69.00; H, 7.06; N, 8.32; Cl, 6.95.

EXAMPLE 14

(+)-3-((αR)-α-((2S,5R)-4-Allyl-2,5-dimethyl-1-piperazinyl)-3-hydroxybenzyl)-N-methyl-N-(2-pyridyl)benzamide 2-(Methylamino)pyridine was prepared from 2-aminopyridine, coupled with 3-((αR)-α-((2S,5R)-4-allyl-2,5-dimethyl-1-piperazinyl)-3-(tert-butyldimethylsilyloxy)benzyl)-benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-methyl-N-(2-pyridyl)benzamide as a light yellow powder. NMR (200 MHz, DMSO-$d_6$): δ0.90 (d,J=6.1 Hz, 3H); 0.98 (d,J=5.9 Hz, 3H); 1.70 (dd, $J_1$=6.8 Hz, $J_2$=10.7 Hz, 1H); 2.02 (dd, $J_1$=7.5 Hz, $J_2$=11.6 Hz, 1H); 2.30 (br, d, J=10.7 Hz, 1H); 2.38–2.57 (m, 2H); 2.66 (dd, $J_1$=2.6 Hz, $J_2$=11.8 Hz, 1H); 2.81 (dd, $J_1$=6.5 Hz, $J_2$=14.5 Hz, 1H); 3.18 (br. d, J=14.4 Hz, 1H); 3.41 (s, 3H); 4.81 (1H); 5.10(d, J=10.2 Hz, 1H); 5.7 (d, J=17.1 Hz, 1H); 5.69–5.88 (m, 1H); 6.43 (d, J=7.6 Hz, 1H); 6.54 (s, 1H); 6.65 (dd, $J_1$=1.7, $J_2$=8.2 Hz, 1H); 6.95–7.32 (m, 7H); 7.64 (td, $J_1$=1.8 Hz, $J_2$=7.7 Hz, 1H); 8.35 (dd, $J_1$=1.3 Hz, $J_2$=4.9 Hz, 1H); 9.33 (s, 1H). Mass spectrum (CI—$CH_4$) m/e: 471 (M+1,100%), 317 (59%), 153 (88%). $[\alpha]_D^{20}$=+12.0° (ethanol. c=1.3). The free amine was dissolved in ethanol and titrated with ethanolic hydrogen chloride to pH 3.2, followed by precipitation with diethyl ether from dichloromethane to give the monohydrochloride salt as a hygroscopic light yellow powder. Calc. for $C_{29}H_{34}N_4O_2$ HCl $H_2O$: C, 66.33; H, 7.10; N, 10.67; Cl, 6.75. Found: C, 66.58; H, 7.32; N, 10.41; Cl, 6.80.

EXAMPLE 15

(+)-3-((αR)-α-((2R,5S)-4-Allyl-2,5-dimethyl-1-piperazinyl)-3-(((benzyloxy)carbonyl)amino)benzyl)phenol 3-((αR)-α-((2S,5R)-4-Allyl-2,5-dimethyl-1-piperazinyl)-3-(tert-butyldimethylsilyloxy)benzyl)benzoyl chloride (Example 9, infra, 1.8 g. crude, approximately 1.12 g. actual compound, 2.18 mmol) was dissolved in 75 mL of acetone and chilled to 0° C. under nitrogen. A solution of sodium azide (1.14 g, 17.5 mmol) in 12 mL of water was added slowly to the mixture. The reaction was stirred at 0° C. for 0.75 hour (with appropriate safety shield) and then warmed to room temperature and stirred for 1.5 hours. The reaction mixture was diluted with 30 mL of water and the acetone was removed in vacuo. The aqueous solution was basified to pH 8 with 1M sodium hydroxide and the acyl azide was extracted with 200 mL diethyl ether. The ether extract was diluted with 75 mL toluene, and the solution volume was concentrated to 50 mL. Benzyl alcohol (0.726 mL, 7.0 mmol) was added, and the reaction was heated at reflux overnight. The solvent was removed in vacuo to give a thick brown oil.

The crude oil and tetraethylammonium fluoride hydrate (0.97 g, 5.25 mmol) were stirred in 30 mL of acetonitrile for 0.5 hour. The solvent was removed, and the residue was purified by chromatography on a silica gel column (4 cm×17 cm) with ethanol (0–3.5%) in dichloromethane to provide 0.321 g (31% from 3-((αR)-α-((2S,5R)-4-allyl-2,5-dimethyl-1-piperazinyl)-3-hydroxybenzyl)benzoic acid) of (+)-3-((αR)-α((2R,5S)-4-allyl-2,5-dimethyl-1-piperazinyl)-3-(((benzyloxy)-carbonyl)amino)benzyl) phenol as a light yellow solid. NMR (200 MHz, DMSO-$d_6$): δ0.97 (d, J=5.9 Hz, 3H); 1.07 (d, J=6.1 Hz, 3H), 1.72–1.93 (m, 2H); 2.10 (dd, $J_1$=6.7 Hz, $J_2$=10.5 Hz, 1H); 2.56–2.92 (m, 3H); 3.18 (dd, $J_1$=5.1 Hz, $J_2$=14.2 Hz, 1H); 3.63 (m, 1H); 4.86 (s, 1H); 5.06–5.26 (m, 4H); 5.70–5.91 (m, 1H); 6.61–6.78 (m, 3H); 7.03 (d, J=7.0 Hz, 1H); 7.15 (m, 1H); 7.21 (d, J=7.8 Hz, 1H); 7.31–7.53 (m, 6H); 7.57 (s, 1H); 9.32 (s, 1H). Mass spectrum (CI—$CH_4$) m/e: 486 (M+1,69%), 332 (64%), 153 (100%). $[\alpha]_D^{20}$=+16.9° (ethanol, c=1.1). The free amine (0.301 g) was dissolved in ethanol and titrated with ethanolic hydrogen chloride to pH 3.1, followed by precipitation with diethyl ether from dichloromethane to give 0.262 g (81% recovery) of the monohydrochloride salt as a hygroscopic light yellow powder. Calc. for $C_{30}H_{35}N_3O_3$ HCl 0.5 $H_2O$: C, 67.85, H, 7.02; N, 7.91; Cl, 6.68. Found: C, 67.65; H, 7.07; N, 7.77; Cl, 6.45.

EXAMPLE 16

(+)-3-((αR)-α-((2S,5R)-4-Allyl-2,5-dimethyl-1-piperazinyl)-3-hydroxybenzyl)-N-(3-fluorophenyl)-N-methylbenzamide Method A 3-Fluoro-N-methylaniline [NMR (200 MHz, DMSO-$d_6$): δ2.76 (s, 3H); 3.42 (s, 1H); 6.51–6.92 (m, 3H); 7.28 (dt,$J_1$=7.3 Hz, $J_2$=8.0 Hz, 1H)].was prepared from 3-fluoroaniline, coupled with 3-((αR)-α-((2S,5R)-4-allyl-2,5-dimethyl-1-piperazinyl)-3-(tert-butyldimethylsiloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-(3-fluorophenyl)-N-methylbenzamide as a light yellow powder. NMR (200 MHz, DMSO-$d_6$): δ0.84 (d, J=6.0 Hz, 3H) 0.97 (d, J=5.9 Hz, 3H); 1.69 (dd, $J_1$=7.7 Hz, $J_2$=10.7 Hz, 1H); 2.01 (dd, $J_1$=7.4 Hz, $J_2$=10.7 Hz, 1H); 2.28 (br d, J=8.3 Hz, 1H); 2.40–2.52 (m, 2H); 2.67 (br d, J=10.5 Hz, 1H 2.82 (dd, $J_1$=7.6 Hz, $J_2$=13.2 Hz, 1H); 3.17 (br d, J=14.0 Hz, 1H); 3.34 (s, 3H); 4.80 (s, 1H); 5.10 (d, J=10.1 Hz, 1H); 5.17 (d,J=17.3 Hz, 1H); 5.70–5.84 (m, 1H); 6.42 (d, J=7.1 Hz, 1H); 6.56 (s, 1H); 6.65 (d, J=8.3 Hz, 1H); 6.90–7.32 (m, 9H); 9.31 (s, 1H). Mass spectrum (CI—$CH_4$) m/e: 488 (M+1, 100%), 334 (39%), 153 (87%). $[\alpha]_D^{20}$=+4.9° (ethanol, c=1.2). The free amine (0.091 g) was dissolved in ethanol and titrated with ethanolic hydrogen chloride to pH 3.7 followed by precipitation with diethyl ether from dichloromethane to give 0.072 g (74% recovery) of the monohydrochloride salt as a hygroscopic light yellow powder. Calc. for $C_{30}H_{34}N_3O_2F$ HCl 1.25 $H_2O$: C, 65.92 H, 6.92; N, 7.69; Cl, 6.49. Found: C, 66.07; H, 6.95; N, 7.53; Cl 6.54.

Method B

3-Fluoro-N-methylaniline was prepared from 3-fluoroaniline using a modified reductive amination. First, 1-hydroxymethylbenzotriazole was prepared by adding 37% aqueous formaldehyde to benzotriazole at 40° C. in a 1:1 ratio and cooling to room temperature to precipitate the product. After filtration the hydroxymethylbenzotriazole 125 g) was heated to reflux in toluene with 3-fluoroaniline (92.2 g). Water was removed azeotropically using a Dean-Stark trap. After three hours, the mixture was cooled to room temperature, then refrigerated for several hours to complete precipitation. The white crystalline solid was collected by filtration. Yielding 174.2 g (86.6%) of 1-((3-fluoroanilino)methyl)-1H-benzotriazole.

1-((3-Fluoroanilino)methyl)-1H-benzotriazole (173 g) was slurried in dry tetrahydrofuran. Sodium borohydride (32.5 g) was added portionwise to the mixture at room temperature. After addition was complete, the mixture was heated at reflux for 4 hours. The solution was cooled and poured slowly into 400 mL of 5M hydrochloric acid with ice and stirred for 1 hour at room temperature. The solution pH was adjusted to 9–10 using 10M sodium hydroxide solution. The product was extracted using diethyl ether. The ether extracts were washed successively with 1M sodium hydroxide solution, saturated sodium chloride solution, and water. The organic phase was dried over sodium sulfate and evaporated under reduced pressure to yield 87.5 g (97%) of 3-fluoro-N-methylaniline as a colorless oil. [NMR (200 MHz, DMSO-$d_6$): δ2.76 (s, 3H); 3.41 (br s, 1H); 6.59–6.92 (m, 3H); 7.27 (q, J=8.0 Hz, 1H)].

3-Carboxybenzaldehyde (Alfrebro Inc., Monroe, Ohio: 2.0 g.) was slurried in thionyl chloride (6 mL). A reflux condenser fitted with a calcium chloride drying tube was placed on the flask. The reaction was placed in an oil bath and heated at a bath temperature maintained below 100° C. The mixture was allowed to reflux until a clear solution was obtained and for 5–10 additional minutes before cooling to room temperature. The solution was diluted with anhydrous toluene, and all volatiles were removed under vacuum.

The crude acid chloride was dissolved in dichloromethane and cooled in an ice/water bath. Triethylamine (6 mL) was added dropwise via an addition funnel, followed by N-methyl-3-fluoroaniline (1.83 g) in dichloromethane. The cloudy solution was allowed to warm to room temperature over 1 hour. Water was added and the product was extracted with dichloromethane. The organic layer was washed with water and saturated sodium chloride solution and dried over sodium sulfate, and the solvent was removed under vacuum. N-(3-Fluorophenyl)-3-formyl-N-methylbenzamide (3.20 g) was obtained as a light golden oil (93% unchromatographed yield). [NMR (300 MHz, DMSO-$d_6$): δ3.38 (s, 3H); 6.94–7.02 (m, 2H); 7.18–7.29(m, 2H); 7.46 (t, J=7.7 Hz, 1H) 7.55 (d, J=7.6 Hz, 1H); 7.81 (m, 2H); 9.90(s, 1H)].

A 12 L, 3-necked round bottom flask was charged with trans-2,5-dimethylpiperazine (767 g, 6.72 mol), which had been recrystallized from toluene to mp=115°–119° C., and 600 mL of water. The flask was cooled in an ice bath and a solution of methanesulfonic acid (1290 g, 13.4 mol) in 600 mL of water was added slowly with stirring and cooling to maintain the temperature below 40° C. The solution was cooled to 20° C. and 800 mL of ethanol was added. A 500 mL addition funnel was filled with 60% aqueous potassium acetate from a 2 L reservoir of the solution, and potassium acetate was added to the reaction flask to adjust the pH to 4.0. A second addition funnel was charged with a solution of ethyl chloroformate (642 mL, 6.71 mol) in 360 mL of tetrahydrofuran. The ethyl chloroformate and potassium acetate solutions were simultaneously added dropwise with adjustment of rate to maintain the reaction solution at pH 4.0±0.1, with cooling as necessary to maintain temperature at 25° C. After addition of the ethyl chloroformate was complete, the reaction was stirred for 1 hour with continued addition of potassium acetate solution to maintain a pH of 4.0. The organic solvents were removed by distillation under vacuum. The remaining aqueous solution was washed with 1500 mL of ethyl acetate to remove any bis-carbamate impurity. The ethyl acetate wash was extracted with two 500 mL portions of 1M hydrochloric acid to recover desired product. The acid extracts were combined with the original aqueous solution and the pH was adjusted to 11 by addition of 10M sodium hydroxide, with cooling to maintain temperature below 40° C. The aqueous solution was extracted with two 1500 mL portions of ethyl acetate, the combined extracts were dried over magnesium sulfate, and the solvent was removed to give 927 g (74%) ethyl trans-2,5-dimethyl-1-piperazinecarboxylate as a yellow oil.

A mixture of ethyl trans-2,5-dimethyl-1-piperazinecarboxylate (643 g, 3.45 mol), allyl bromide (328 mL, 3.80 mol), and sodium carbonate (440 g, 4.15 mol) in 2500 mL of acetonitrile was heated at reflux for 1.5 hours. The reaction was cooled to room temperature, filtered, and the solvent removed under vacuum. The residue was dissolved in 4000 mL of dichloromethane and washed with two 500 mL portions of 1M sodium hydroxide. The dichloromethane solution was dried over magnesium sulfate and the solvent was removed to give 630 g (81%) of ethyl trans-4-allyl-2, 5-dimethyl-1-piperazinecarboxylate as an oil.

Ethyl trans-4-allyl-2,5-dimethyl-1-piperazinecarboxylate (630 g, 2.78 mol) was added to a solution of 87% potassium hydroxide pellets (2970 g, 46 mol) in 4300 mL of 95% ethanol and heated at reflux for 1.5 hours. Carbon dioxide evolution was observed for the first 0.5–1 hour of heating. The reaction was cooled below reflux temperature and 2000 mL of toluene was carefully added. Ethanol was removed by azeotropic distillation at 105° C. while adding an additional 4000 mL of toluene to the reaction flask during the course of the distillation. After collection of 9000 mL of distillate, the reaction was cooled to 100° C. and 1000 mL of toluene was carefully added. The solution was slowly cooled to 5° C. and maintained at 5° C. for 30 minutes. The solution was filtered, and the filter cake was washed with an additional 1500 mL of toluene. The filtrate was washed with 1000 mL of water, dried over magnesium sulfate, and the solvent was removed to give 296 g (69%) of trans-1-allyl-2,5-dimethylpiperazine as a dark liquid. NMR (300 MHz, DMSO-$d_6$): $\delta$0.87 (d, J=6.3 Hz, 3H); 0.92 (d, J=6.3 Hz, 3H); 1.63 (t, J=11 Hz, 1H); 2.05 (m, 1H); 2.30 (t, J=11 Hz, 1H); 2.6–2.8 (m, 4H); 3.33 (dd, $J_1$=5 Hz, $J_2$=14 Hz, 1H); 5.09 (d, J=8.7 Hz, 1H); 5.13 (d, J=14 Hz, 1H) 5.8 (m, 1H).

Di-p-toluoyl-D-tartaric acid (Schweizerhall, Inc., South Plainfield, N.J.) (1.25 Kg, 3.2 mol) was dissolved in hot (~60° C.) 95% ethanol (16 L) and racemic trans-1-allyl-2, 5-dimethylpiperazine (500 g, 3.2 mol) was added in several portions (caution: exothermic). The hot solution was seeded with crystals of the diastereoisomerically pure salt (obtained from a previous small-scale resolution) and cooled to room temperature over 2–3 hours. The solution was slowly stirred for 2 \ days at room temperature. The resulting salt was collected by filtration, washed twice with 95% ethanol, and dried under vacuum to give 826.5 g of a white solid (47%). The process was repeated with a second batch of the di-p-toluoyl-D-tartaric acid and racemic trans-1-allyl-2,5-dimethylpiperazine to give 869 g (50%).

The total of 1695 g of salt was divided into three batches and each batch was recrystallized twice in the following fashion. The salt was dissolved in refluxing 95% ethanol (~2.7 L/100 g of salt), and approximately half of the ethanol was removed by distillation. (Note: vigorous stirring was necessary during distillation to prevent crystallization on the vessel wall.) The hot solution was seeded with crystals of the pure diastereomeric salt, cooled to room temperature, and stirred slowly for 2 days before collecting the salt by filtration. (Note: a subsequent experiment suggested that crystallization time can be reduced from 2 days to 8 hours.) The total amount recovered was 1151 g. The salt was dissolved in 3 L of 2M aqueous sodium hydroxide, and the aqueous solution was extracted with four 1 L portions of dichloromethane. The organic extracts were combined, dried over sodium sulfate, and solvent removed by rotary evaporation (temperature<20° C.) to give 293 g (29% based on racemic weight) of (2R,5S)-1-allyl-2,5-dimethylpiperazine as a clear oil. $[\alpha]_D^{20}$=-55.1° (abs. ethanol, c=1.2). The trifluoroacetamide of the product was prepared with trifluoroacetic anhydride and analyzed by chiral capillary gas chromatography (Chiraldex B-PH column, 20 m×0.32 mm, Advanced Separation Technologies Inc., Whippany, N.J., 120° C.) indicating an enantiopurity of >99% ee (retention time of desired enantiomer, 11.7 min; other enantiomer, 10.7 min).

(2R,5S)-1-allyl-2,5-dimethylpiperazine (6.13 g), benzotriazole (4.79 g), and N-(3-fluorophenyl)-3-formyl-N-methylbenzamide (10.23 g) were mixed in dry toluene with one drop of triethylamine. The mixture was placed in an oil bath maintained at 140° C. (bath temperature). The flask was attached to a Dean-Stark trap to allow the azeotropic removal of water, under a stream of nitrogen. The mixture was heated at reflux for 2–3 hours and most of the toluene was removed under reduced pressure. The crude adduct may be isolated by crystallization at this stage to give 3-(((2R, 5S)-4-allyl-2,5-dimethyl-1-piperazinyl)-3-(1H-benzotriazol-1-yl)methyl)-N-(3-fluorophenyl)-N-methylbenzamide as a mixture of epimers, but due to the water-sensitive nature of the adduct, it is generally easier to use the crude material for subsequent reactions. (The reaction mixture in toluene is usually satisfactory for the next step.)

A solution of 3-bromophenol (500 g, 2.89 mol), tert-butylchlorodimethylsilane (436 g, 2.89 mol), and imidazole (500 g, 7.22 mol) in 500 mL of dimethylformamide was stirred overnight at room temperature. The reaction solution was poured into 3000 mL of water and extracted with two 2000 mL portions of diethyl ether. The combined ether extracts were dried over sodium sulfate and the solvent removed to give 846 g of 3-(bromophenoxy)-tert-butyldimethylsilane as a pale yellow liquid. NMR (300 MHz, CDCl$_3$): $\delta$0.2 (s, 6H); 1.0 (s, 9H); 6.75 (m, 1H); 7.0 (br s, 1H); 7.1 (m, 2H).

3-(Bromophenoxy)-tert-butyldimethylsilane (17.12 g) was dissolved in dry tetrahydrofuran (150 mL), and cooled to −78° C. under nitrogen. n-Butyllithium in hexanes (23.88 mL of a 2.5M solution) was added slowly via syringe to the solution. While stirring for 40 minutes at −78° C., the solution became white and somewhat thick. The solution was transferred via a double-ended needle to a flask containing magnesium bromide etherate (16.5 g) in tetrahydrofuran (150 mL) and stirred for 1 hour at room temperature. The crude benzotriazole adduct from above containing primarily 3-(((2R,5S)-4-allyl-2,5-dimethyl-1-piperazinyl)-3-(1H-benzotriazol-1-yl)methyl)-N-(3fluorophenyl)-N-methylbenzamide was dissolved in tetrahydrofuran and added to the arylmagnesium bromide reagent just prepared. The solution warmed slightly during the addition and became a cloudy yellow-brown color. After stirring at room temperature for 2 hours. 0.5M aqueous hydrochloric acid was added cautiously until the solution reached pH=6. The product was extracted with 250 mL of ethyl acetate and the solvent was removed under vacuum.

The tert-butyldimethylsilyl protecting group was removed by dissolving the residue in 175 mL of tetrahydrofuran and adding 85 mL of 3N aqueous HCl at room temperature. The solution warmed upon acid addition. The mixture was stirred for 40 minutes at room temperature. Diethyl ether was added, and the acidic aqueous layer was separated. The aqueous layer was washed a second time with diethyl ether and adjusted to pH=8–9 using aqueous sodium hydroxide solution. The product was extracted using ethyl acetate. The ethyl acetate portions were combined, and washed with dilute sodium hydroxide solution to remove any remaining benzotriazole. The organic layer was then washed with saturated sodium chloride solution, dried over sodium sulfate, and evaporated under reduced pressure. The product (10.85 g, 56%) was recovered as a mixture of two diastereomers in a 91:9 ratio favoring the desired diastereomer, as determined by HPLC analysis. HPLC was performed on a μ-Bondapak C-18 column (125 Å, 3.9×300 nm. Waters Chromatography Division, Millipore Corporation, Milford, Mass. using 60% methanol and 40% 0.1M aqueous ammonium acetate at a flow rate of 1 mL/min. The diastereomeric mixture was recrystallized from ethyl acetate/hexane to give (+)-3-((αR)-α-((2S,5R)-4-allyl-2,5-dimethyl-1-piperazinyl)-3-hydroxybenzyl-N-(3-fluorophenyl)-N-methylbenzamide as a white crystalline solid (mp 144°–145° C.) in 99% isomeric purity (as determined by HPLC). NMR (200 MHz, DMSO-d6): $\delta$0.84 (d, J=6.0 Hz, 3H); 0.97 (d, J=5.9 Hz, 3H); 1.69 (dd, $J_1$=7.7 Hz, $J_2$=10.7 Hz, 1H); 2.01 (dd, $J_1$=7.4 Hz, $J_2$=10.7 Hz, 1H); 2.28 (br d, J=8.3 Hz, 1H); 2.40–2.52 (m, 2H);2.67 (br d, J =10.5 Hz, 1H); 2.82 (dd, $J_1$=7.6 $J_2$=13.2 Hz, 1H); 3.17 (br d, J=14.0 Hz, 1H); 3.34 (s, 3H); 4.80 (s, 1H); 5.10 (d, J=10.1 Hz, 1H); 5.17 (d, J=17.3 Hz, 1H); 5.70–5.84 (m, 1H); 6.42 (d, J=7.1 Hz, 1H); 6.56 (s, 1H); 6.65 (d, J=8.3 Hz, 1H); 6.90–7.32 (m, 9H); 9.31 (s, 1H). Mass spectrum (CI—CH$_4$) m/e: 488 (M+1, 100%), 334 (39%), 153 (87%). [α]$_D^{20}$=+5.4° (abs. ethanol. c=1.4). Calc. for C$_{30}$H$_{34}$FN$_3$O$_2$: C, 73.90; H, 7.03; N, 8.62. Found: C. 73.86; H, 7.02; N, 8.53. The monohydrochloride salt may be formed as in Method A.

EXAMPLE 17

3-((αR)-α-((2S, 5R)-4-Allyl-2,5-dimethyl-1-piperazinyl)-3-hydroxybenzyl)-N-Methyl-N-(2,4,6-trichlorophenyl)benzamide N-Methyl-2,4,6-trichloroaniline [NMR (200 MHz, CDCl$_3$); δ2.82 (s, 3H); 5.11 (s, 1H); 7.46 (s, 2H)] was prepared from 2,4,6-trichloroaniline, coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-methyl-N-(2,4,6-trichlorophenyl)-benzamide as an off-white powder. NMR (200 MHz, DMSO-d$_6$): δ0.90 (d, J=6.1 Hz, 3H); 0.98 (d, J=6.0 Hz, 3H); 1.65 (dd, J$_1$=7.4 Hz, J$_2$=10.6 Hz, 1H); 2.03 (dd, J$_1$=7.5 Hz, J$_2$=10.2 Hz, 1H); 2.35 (d, J=11.7 Hz, 1H); 2.38–2.51 (m, 2H); 2.65 (br d, J=10.6 Hz, 1H); 2.80 (dd, J$_1$=7.0 Hz, J$_2$=13.3 Hz, 1H); 3.12 (m, 1H); 3.18 (s, 3H); 4.80 (s, 1H); 5.11 (d, J=11.0 Hz, 1H); 5.18 (d, J=16.8 Hz, 1H); 5.66–5.87 (m, 1H); 6.48 (d, J=8.4 Hz, 1H); 6.56 (s, 1H); 6.64 (d, J=8.6 Hz, 1H); 7.16 (t, J=8.0, 1H); 7.22–7.28 (m, 3H); 7.38 (s, 1H); 7.69 (d, J=2.2 Hz, 1H); 7.72 (d, J=2.2 Hz, 1H); 9.31 (s, 1H). Mass spectrum (CI—CH$_4$) m/e: 572 (M+1.14%), 153 (100%).

EXAMPLE 18

3-((αR)-α-((2S,5R)-4-Allyl-2,5-dimethyl-1-piperazinyl)-3-hydroxybenzyl)-N-methyl-N-(2-(trifluoromethyl)phenyl)-benzamide N-methyl-2-(trifluoromethyl)aniline [NMR (200 MHz, DMSO-d$_6$): δ2.75 (s, 3H); 3.40 (s, 1H); 6.70 (t, J=8.0 Hz, 1H); 6.94–7.16 (br. m, 2H); 7.38 (d, J=7.3 Hz, 1H)] was prepared from 2- (trifluoromethyl)aniline, coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-methyl-N-(2-(trifluoromethyl)phenyl)benzamide as a yellow powder. NMR (200 MHz, DMSO-d$_6$): δ0.90 (d, J=6.0 Hz, 3H); 0.97 (d, J=6.0 Hz, 3H); 1.64 (m, 1H); 2.05 (m, 1H); 2.27 (br d, J=10.5 Hz,1H); 2.40–2.84 (m, 4H); 3.18 (br d, J=13.5 Hz, 1H); 3.29 (s, 3H); 4.79 (s, 1H); 5.11 (d, J=10.2 Hz, 1H); 5.18 (d, J=17.0 Hz, 1H); 5.70–5.82 (m, 1H); 6.42 (d, J=7.6 Hz, 1H); 6.65 (d, J=7.7 Hz, 1H); 6.67 (s, 1H); 7.04–7.83 (m, 9H); 9.32 (s, 1H). Mass spectrum (CI—CH$_4$) m/e: 538 (M+1, 82%), 384 (13%), 153 (100%).

EXAMPLE 19

(+)-3-((αR)-α-((2S,5R)-4-Allyl-2,5-dimethyl-1-piperazinyl)-3-(hydroxybenzyl)-N-methyl-N-(3-pyridyl)benzamide 3-(Methylamino)pyridine [NMR (200 MHz, CDCl$_3$): δ2.80 (s, 3H); 3.90 (s, 1H); 6.83 (d, J=8.2 Hz, 1H); 7.06 (dd, J$_1$=4.7 Hz, J$_2$=8.2 Hz, 1H); 7.91 (d, J=4.7 Hz, 1H); 7.99 (s, 1H)] was prepared from 3-aminopyridine, coupled with 3-((αR)-α-((2S,5R)-4-allyl-2,5-dimethyl-1-piperazinyl)-3-(tert-butyldimethylsilyloxy)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-methyl-N-(3-pyridyl)benzamide as a light yellow powder. NMR (200 MHz, DMSO-d$_6$): δ0.90 (d, J=6.1 Hz, 3H); 0.99 (d, J=6.3 Hz, 3H); 1.71 (m, 1H); 2.03 (m, 1H); 2.30 (br d, J=10.4 Hz, 1H); 2.42–2.94 (m, 4H); 3.20 (br d, J=13.3 Hz, 1H); 3.39 (s, 3H); 4.82 (s, 1H): 5.12 (d, J=9.9 Hz, 1H); 5.18 (d, J=17.0 Hz, 1H); 5.70–5.86 (m, 1H); 6.44 (d, J=7.7 Hz, 1H); 6.56 (s, 1H); 6.66 (d, J=8.8 Hz, 1H); 7.13 (t, J=8.1 Hz, 1H); 7.18–7.41 (m, 5H); 7.64 (dd, J$_1$=1.4 Hz, J$_2$=8.1 Hz, 1H); 8.29 (s, 1H); 8.34 (d, J=4.5 Hz, 1H); 9.34 (s, 1H). [α]$_D^{20}$=+11.8° (abs. ethanol. c=1.0).

EXAMPLE 20

(+)-3-((αR)-α-((2S,5R)-4-Allyl-2,5-dimethyl-1-piperazinyl)-3-hydroxybenzyl)-N-benzyl-N-methylbenzamide This compound was prepared from 3-((αR)-α-((2S,5R)-4-allyl-2,5-dimethyl-1-piperazinyl)-3-(tert-butyldimethylsilyloxy)benzyl)benzoyl chloride and N-benzyl-N-methylamine by the Benzamide Formation Method described in Example 9. NMR (300 MHz, DMSO-d$_6$, 121° C.): δ0.93 (d, J=6.2 Hz, 3H) 1.06 (d, J=6.2 Hz, 3H); 1.96 (dd, J$_1$=6.7 Hz, J$_2$=11.0 Hz, 1H); 2.12 (dd, J$_1$=7.0 Hz, J$_2$=11.0 Hz, 1H); 2.58 (dd, J$_1$=2.9 Hz, J$_2$=11.4 Hz, 1H); 2.67–2.84 (m, 3H); 2.86 (s, 3H); 2.89 (dd, J$_1$=6.6 Hz, J$_2$=13.5 Hz, 1H); 3.18 (dd, J$_1$=4.0 Hz, J$_2$=14.1 Hz, 1H); 4.58 (s, 2H); 4.98 (s, 1H); 5.08 (d, J=10.2 Hz, 1H); 5.16 (d, J=17.3 Hz, 1H); 5.74–5.89 (m, 1H); 6.62–6.74 (m, 3H); 7.10 (t, J=7.8 Hz, 1H); 7.21–7.50 (m, 9H); 8.76 (s, 1H). Mass spectrum (CI—CH$_4$) m/e: 484 (M+1,88%), 330 (33%), 153 (100%). [α]$_D^{20}$=+14.3° (ethanol. c=1.25). The free amine was dissolved in ethanol and titrated with ethanolic hydrogen chloride to pH 3.4 followed by precipitation with diethyl ether from dichloromethane to give (+)-3-((αR)-α-(2S,5R)-4-allyl-2,5-dimethyl-1-piperazinyl)-3-hydroxybenzyl)-N-benzyl-N-methylbenzamide monohydrochloride as a hygroscopic light yellow powder. Calc. for C$_{31}$H$_{37}$N$_3$O$_2$ HCl 0.75 H$_2$O: C, 69.78; H, 7.46; N, 7.87; Cl, 6.64 Found: C, 69.76; H, 7.48; N, 7.69; Cl 6.74.

EXAMPLE 21

(±)-cis-3-(α-(4-Allyl-3,5-dimethyl-1-piperazinyl)-3-hydroxybenzyl)-N,N-diethylbenzamide (±)-3-(α-(3,5-Dimethyl-1-piperazinyl)-3-hydroxybenzyl)-N,N-diethylbenzamide was prepared from 3-(3-((tert-butyldimethyl-silyl)oxy)-α-chlorobenzyl)-N,N-diethylbenzamide (Example 1, infra) and cis-2,6-dimethylpiperazine according to the methods of Example 1. This material was then alkylated with allyl bromide and deprotected by methods similar to that in Example 4 to give (±)-cis-3-(α-(4-allyl-3,5-dimethyl-1-piperazinyl)-3-hydroxybenzyl)-N,N-diethylbenzamide. NMR (DMSO-d$_6$, 200 MHz): δ0.87 (d, J=3.9 Hz, 3H); 0.90 (d, J=3.9 Hz, 3H); 0.940–1.22 (m, 6H); 1.65 (t, J=10.7 Hz, 2H); 2.55–2.75 (m, 4H); 3.00–3.22 (m, 2H); 3.22–3.54 (m, 4H); 4.16 (s, 1H); 5.15 (dd, J$_1$=2.2 Hz, J$_2$=10.0 Hz, 1H); 5.22 (d, J=14.8 Hz, 1H); 5.96 (m, 1H); 6.58 (d, J=8.0 Hz, 1H); 6.82 (d, J=7.3 Hz, 1H); 6.84 (s, 1H); 7.02–7.20 (m, 2H); 7.30–7.46 (m, 3H); 9.33 (s, 1H). Mass spectrum (CI—CH$_4$) m/e: 436 (M+1. 100%). The monohydrochloride salt was prepared as in Example 4. Calc. for C$_{27}$H$_{37}$N$_3$O$_2$ HCl 0.75 H$_2$O: C, 66.78: H, 8.20; N, 8.65; Cl, 7.30. Found: C, 66.84; H, 8.28; N, 8.53; Cl, 7.25.

EXAMPLE 22

3-((αR or αS)-α-((2S,5S)-4-Allyl-2,5-dimethyl-1-piperazinyl)-3-hydroxybenzyl)-N,N-diethylbenzamide 3-(α-((2S,5S)-2,5-Dimethyl-1-piperazinyl)-3-hydroxybenzyl)-N,N-diethylbenzamide was prepared as a mixture of epimers from 3-(3-((tert-butyldimethylsilyl)oxy)-α-chlorobenzyl)-N,N-diethylbenzamide (Example 1, infra) and (+)-(2S,5S)-2,5-dimethylpiperazine [prepared from L-Ala-L-Ala-diketopiperazine (Bachem Chemicals, Philadelphia, Pa.) as described by Jung and Rohloff (J. Org. Chem. 50, 4909–13 (1985))] according to the methods of Example 1. This material was then alkylated with allyl bromide by methods similar to that in Example 4 to give a mixture of diastereomers that was separated by chromatography on silica gel (Waters Prep 500A, 0.1% triethylamine in dichloromethane). The first isomer to elute was deprotected by the method in Example 4 to give 3-((αR or αS)-α-((2S,5S)-4-Allyl-2,5-dimethyl-1-piperazinyl)-3-hydroxybenzyl)-N,N-diethylbenzamide. NMR (DMSO-$d_6$, 200 MHz): δ0.890 (d, J=5.6 Hz, 3H); 0.981 (d, J=6.4 Hz, 3H); 1.00–1.25 (m, 6H); 2.10–2.48 (m, 4H); 2.59 (d, J=11.1 Hz, 1H); 2.73 (dd, $J_1$=7.8 Hz, $J_2$=14.1 Hz, 1H); 2.90–3.60 (m, 6H); 4.54 (s, 1H); 5.13 (d, J=9.0 Hz, 1H); 5.19 (d, J=16.2 Hz, 1H); 5.84 (m, 1H); 6.58 (d, J=8.0 Hz, 1H); 6.86 (s, 1H); 6.88 (d, J=7.1 Hz, 1H); 7.08 (t, J=7.6 Hz, 1H); 7.14 (d, J=7.8 Hz, 1H); 7.34 (t, J=7.6 Hz, 1H); 7.43 (s, 1H); 7.48 (d, J=7.7 Hz, 1H); 9.32 (s, 1H).

EXAMPLE 23

3-((αS or αR)-α-((2S,5S)-4-Allyl-2,5-dimethyl-1-piperazinyl)-3-hydroxybenzyl)-N,N-diethylbenzamide The second isomer to elute from the column of Example 22 was deprotected in similar fashion to give the benzhydryl epimer of Example 22. NMR (DMSO-$d_6$, 200 MHz): δ0.903 (d, J=5.5 Hz, 3H); 0.965 (d, J=6.5 Hz, 3H); 1.00–1.20 (m, 6H); 2.16 (t, J=9.9 Hz, 1H); 2.25–2.45 (m, 3H); 2.48–2.62 (m, 1H); 2.70–2.90 (m, 2H); 3.00–3.25 (m, 2H); 3.25–3.50 (m, 3H); 4.52 (s, 1H); 5.12 (d, J=8.6 Hz, 1H); 5.18 (d, J=16.0 Hz, 1H); 5.82 (m, 1H); 6.56 (d, J=7.0 Hz, 1H); 6.89 (d, J=7.4 Hz, 1H); 6.91 (s, 1H); 7.06 (t, J=8.0 Hz, 1H); 7.14 (d, J=7.2 Hz, 1H); 7.35 (t, J=7.4 Hz, 1H); 7.38 (s, 1H); 7.49 (d, J=7.6 Hz, 1H); 9.31 (s, 1H).

EXAMPLE 24

3-((αR or αS)-α-(2R,5R)-4-Allyl-2,5-dimethyl-1-piperazinyl)-3-hydroxybenzyl)-N,N-diethylbenzamide, the enantiomer of Example 22, was prepared in identical fashion to Example 22 using (−)-(2R,5R)-2,5-dimethylpiperazine [prepared from D-Ala-D-Ala-diketopiperazine (Bachem Chemicals, Philadelphia, Pa.) as described by Jung and Rohloff (J. Org. Chem. 50, 4909–13 (1985))]. Chromatography of the silyl-protected product provided the first isomer to elute as a yellow oil. Deprotection with tetraethylammonium flouride gave the desired product. NMR (DMSO-$d_6$, 300 MHz): δ0.85 (d, J=6 Hz, 3H); 0.95 (d, J=6 Hz, 3H); 2.15 (t, J=9 Hz, 1H); 2.25 (m, 2H); 2.35 (dd, $J_1$=3 Hz, $J_2$=11 Hz, 1H); 2.55 (dd, $J_1$=2 Hz, $J_2$=11 Hz, 1H); 2.7 (q, J=7 Hz, 1H); 2.95 (m, 1H); 3.1 (br m, 2H); 3.4 (br m, 3H); 4.5 (s, 1H); 5.1 (d, J=11 Hz, 1H); 5.2 (d, J=17 Hz, 1H); 5.80 (m, 1H); 6.5 (d, J=8 Hz, 1H); 6.8 (s, 1H); 6.8 (d, J=8 Hz, 1H); 7.05 (t, J=8 Hz, 1H); 7.1 (d, J=8 Hz, 1H); 7.4 (s, 1H); 7.45 (d, J=8 Hz, 1H); 9.3 (s, 1H).

EXAMPLE 25

3-((αS or αR)-α-(2R,5R)-4-Allyl-2,5-dimethyl-1-piperazinyl)-3-hydroxybenzyl)-N,N-diethylbenzamide, the enantiomer of Example 23, was obtained after deprotection of the second isomer to elute from the column of Example 24. NMR (DMSO-$d_6$, 300 MHz): δ0.8 (d, J=5.5 Hz, 3H); 0.93 (d, J=6.3 Hz, 3H); 0.95–1.20 (m, 6H); 2.12 (t, J=10.5 Hz, 1H); 2.20–2.40 (m, 3H); 2.54 (d, J=10.2 Hz, 1H); 2.66–2.87 (m, 2H); 2.95–3.50 (m, 5H); 4.48 (s, 1H); 5.09 (d, J=11.5 Hz, 1H); 5.14 (d, J=19.9 Hz, 1H); 5.80 (m, 1H); 6.52 (dd, $J_1$=1.8 Hz, $J_2$=7.6 Hz, 1H); 6.85 (d, J=8.1 Hz, 1H); 6.86 (s, 1H); 7.02 (t, J=7.6 Hz, 1H); 7.10 (d, J=7.6 Hz, 1H); 7.31 (t, J=7.6 Hz, 1H); 7.34 (s, 1H); 7.45 (d, J=7.9 Hz, 1H); 9.28 (s, 1H).

EXAMPLE 26

(+)-3-((αS)-α-((2S,5R)-4-Allyl-2,5-dimethyl-1-piperazinyl)-3-hydroxybenzyl)-N-methyl-N-phenylbenzamide 3-((αS)-α-((2S,5R)-4-Allyl-2,5-dimethyl-1-piperazinyl)-3-bromo-benzyl)phenol (2.30 g, 5.5 mmol. Example 9. infra) was treated with tert-butylchlorodimethylsilane (1.67 g, 11 mmol) and imidazole (0.94 g, 13.8 mmol) in 30 mL of dimethylformamide at room temperature under nitrogen overnight. The reaction mixture was poured into ice-water and extracted with diethyl ether. The ethereal layers were washed with water and brine, dried over sodium sulfate, and concentrated to dryness. The residue was purified by chromatography on silica gel with hexane:ethyl acetate (0–50%) to give 2.36 g of the silyl ether as a yellow oil.

The silyl ether (2.25 g, 4.2 mmol) was dissolved in 80 mL of dry tetrahydrofuran, dried further over molecular sieves, then transferred to a reaction flask under nitrogen and cooled to −78° C. n-Butyllithium (2.6 mL of a 1.6M solution in hexane) was added, while stirring under nitrogen, at a rate to keep the temperature below −70° C. Stirring was continued at −78° C. for 1 hour. Carbon dioxide was bubbled through the reaction mixture for 2–3 minutes. The mixture was warmed to room temperature with continual stirring to maintain steady degassing of dissolved carbon dioxide. The solvent was evaporated, the residue was redissolved in toluene, and the solvent was again removed under vacuum to eliminate all n-bromobutane. The residue was dissolved in dichloromethane (50 mL), thionyl chloride (0.46 mL, 6.3 mmol) was added, and the mixture was stirred at room temperature for 40 minutes. Triethylamine (2.3 mL, 16.8 mmol) and N-methylaniline (0.5 mL, 4.6 mmol) were added, and stirring was continued at room temperature overnight. The reaction mixture was washed with water, dried over sodium sulfate, and the solvent was removed under vacuum to give 2.68 g of a brown oil. The crude product was dissolved in acetonitrile and treated with 1.2 g (6.3 mmol) of tetraethylammonium fluoride dihydrate at room temperature for 10 minutes. The solvent was evaporated and the residue was purified by chromatography on silica gel with dichloromethane:ethanol (0–3.5%) to give 0.92 g of (+)-3-((αS)-α-((2S,5R)-4-allyl-2,5-dimethyl-1-piperazinyl)-3-hydroxybenzyl)-N-methyl-N-phenylbenzamide as a light beige solid. NMR (DMSO-$d_6$, 200 MHz) δ: 0.9 (d, J=6 Hz, 3H); 0.95 (d, J=6 Hz, 3H); 1.7 (dd, $J_1$=6 Hz, $J_2$=8 Hz, 1H); 2.0 (dd, $J_1$=7 Hz, $J_2$=10 Hz, 1H); 2.1 (m, 1H); 2.4–2.7 (m, 3H); 2.85 (dd, $J_1$=7 Hz, $J_2$=14 Hz, 1H); 3.15 (dd, $J_1$=7 Hz, $J_2$=15 Hz, 1H); 3.4 (s, 3H); 4.7 (s, 1H); 5.1 (d, J=10 Hz, 1H); 5.2 (d, J=17 Hz, 1H); 5.8 (m, 1H); 6.6 (m, 2H); 6.8 (s, 1H); 7.0 (t, J=8 Hz, 1H); 7.1–7.3 (m, 9H); 9.4 (s, 1H). $[α]_D^{20}$=+4° (abs ethanol, c=2.7). The product was dissolved in absolute ethanol and titrated to pH 3 with ethanolic hydrogen chloride. The solution was concentrated and diethyl ether was added to precipitate the monohydrochloride salt which was dried under vacuum to give 0.617 g of a light beige powder. Calc. for $C_{30}H_{35}N_3O_2$ HCl 0.70 $H_2O$: C, 69.47; H, 7.27; N, 8.10; Cl, 6.84. Found: C, 69.76; H, 7.27; N, 7.74; Cl, 6.60.

EXAMPLE 27

(+)-3-((αR)-α-((2S,5R)-4-Allyl-2.5-dimethyl-1-piperazinyl)-3-hydroxybenzyl)-N-phenyl-N-propylbenzamide N-Propylaniline was prepared from aniline and propionic anhydride, coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-phenyl-N-propylbenzamide as a light yellow solid. NMR (200 MHz, DMSO-$d_6$): δ0.87 (t, J=7.4 Hz, 3H); 0.91 (d, J=5.9 Hz, 3H); 0.98 (d, J=6.0 Hz, 3H); 1.51 (m, 2H); 1.69 (dd, $J_1$=7.2 Hz, $J_2$=10.9 Hz, 1H); 2.06 (dd, $J_1$=7.0 Hz, $J_2$=10.5 Hz, 1H); 2.30 (d, J=10.3 Hz, 1H); 2.39–2.54 (m, 2H); 2.65 (br d, J=10.3 Hz, 1H); 2.85 (dd, $J_1$=7.4 Hz, $J_2$=14.5 Hz, 1H); 3.16 (dd, $J_1$=5.1 Hz, $J_2$=14.2 Hz, 1H); 3.79 (t, J=7.6 Hz, 2H); 4.77 (s, 1H); 5.12 (d, J=10.2 Hz, 1H); 5.18 (d, J=16.0 Hz, 1H); 5.71–5.84 (m, 1H); 6.43 (d, J=7.6 Hz, 1H); 6.57 (s, 1H); 6.64 (d, J=8.0 Hz, 1H); 7.02–7.33 (m, 10H); 9.32 (s, 1H). Mass spectrum (CI—$CH_4$) m/e: 498 (M+1,100%), 344 (23%), 153 (80%), $[α]_D^{20}$=+8.9° (ethanol, c=1.1). The free amine (0.585 g) was dissolved in ethanol and titrated with ethanolic hydrogen chloride to pH 4.0 followed by precipitation with diethyl ether from dichloromethane to give 0.479 g of the monohydrochloride salt as a hygroscopic off-white powder. Calc. for $C_{32}H_{39}N_3O_2$ HCl 0.75 $H_2O$: C, 70.18; H, 7.64; N, 7.67; Cl, 6.47. Found: C, 70.16; H, 7.73; N, 7.59; Cl, 6.51.

EXAMPLE 28

(+)-3-((αR)-α-((2S,5R)-4-Allyl-2,5- dimethyl-1-piperazinyl)-3-hydroxybenzyl)-N-ethyl-N-(4-fluorophenyl)benzamide Method A 4-Fluoro-N-ethylaniline [NMR (200 MHz, DMSO-$d_6$): δ1.25 (t, J=7.1 Hz, 3H); 3.12 (q, J=7.1 Hz, 2H); 3.24 (br s, 1H); 6.57 (dd, $J_1$=4.5 Hz, $J_2$=9.0 Hz, 2H); 6.90 (t, J=8.9 Hz, 2H)] was prepared from 4-fluoroaniline and acetic anhydride, coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-ethyl-N-(4-fluorophenyl)benzamide as an off-white powder. NMR (200 MHz, DMSO-$d_6$): δ0.91 (d, J=6.1 Hz, 3H); 0.98 (d, J=6.0 Hz, 3H); 1.08 (t, J=7.0 Hz, 3H); 1.71 (dd, $J_1$=7.0 Hz, $J_2$=11.3 Hz, 1H); 2.05 (dd, $J_1$=7.2 Hz, $J_2$=10.8 Hz, 1H); 2.31 (d, J=11.4 Hz, 1H) 2.36–2.57 (m, 2H); 2.69 (dd, $J_1$=2.2 Hz, $J_2$=10.7 Hz, 1H); 2.85 (dd, $J_1$=7.0 Hz, $J_2$=13.9 Hz, 1H); 3.18 (dd, $J_1$=5.3 Hz, $J_2$=13.9 Hz, 1H); 3.84 (q, J=7.0 Hz, 2H); 4.78 (s, 1H); 5.11 (d, J=10.0 Hz, 1H); 5.18 (d, J=16.4 Hz, 1H); 5.65–5.88 (m, 1H); 6.46 (d, J=7.4 Hz, 1H); 6.58 (s, 1H); 6.65 (d, J=8.1 Hz, 1H); 7.01–7.27 (m, 9H); 9.33 (s, 1H). Mass spectrum (CI—$CH_4$) m/e: 502 (M+1.90%), 348 (15%), 153 (100%). $[α]_D^{20}$=6.30° (abs. ethanol, c=1.1) The free amine (0.313 g) was dissolved in ethanol and titrated with ethanolic hydrogen chloride to pH 3.95 followed by precipitation with diethyl ether from dichloromethane to give 0.263 g of the monohydrochloride salt as a hygroscopic white powder. Calc. for $C_{31}H_{36}N_3O_2F$ HCl $H_2O$: C, 66.95; H, 7.07; N, 7.56; Cl, 6.38. Found: C, 66.97; H, 7.10; N, 7.47; Cl, 6.41.

Method B

4-Fluoro-N-ethylaniline [NMR (200 MHz, DMSO-$d_6$): δ1.25 (t, J=7.1 Hz, 3H); 3.12 (q, J=7.1 Hz, 2H); 3.24 (br s, 1H); 6.57 (dd, $J_1$=4.5 Hz, $J_2$=9.0 Hz, 2H); 6.90 (t, J=8.9 Hz, 2H)] was prepared from 4-fluoroaniline and acetic anhydride by the methods described in Example 10. The aniline was used to form N-(4-fluorophenyl)-3-formyl-N-ethylbenzamide [NMR (200 MHz, DMOS-$d_6$): δ1.11 (t, J=7.0 Hz, 3H); 3.88 (q, J=7.0 Hz, 2H); 7.10 (t, J=8.6 Hz, 2H); 7.21–7.35 (m, 2H); 7.46 (q, J=7.4 Hz, 1H); 7.56 (d, J=7.2 Hz, 1H; 7.83 (m, 2H); 9.93 (s, 1H)] by the methods described in Example 16, Method B. (+)-3-((αR)-α-((2S,5R)-4-Allyl-2,5-dimethyl-1-piperazinyl)-3-hydroxybenzyl)-N-ethyl-N-(4-fluorophenyl)-benzamide was obtained as a white crystalline solid from N-(4-fluorophenyl)-3-formyl-N-ethylbenzamide via crude 3-(((2R,5S)-4-allyl-2,5-dimethyl-1-piperazinyl)-3-(1H-benzotriazol-1-yl)methyl)-N-ethyl-N-(4-fluorophenyl)benzamide using the procedures described in Example 16, Method B. The final recrystallization was performed in acetonitrile to give colorless crystals, mp. 111°–112° C. NMR (200 MHz, DMSO-$d_6$): δ0.91 (d, J=6.1 Hz, 3H): 0.98 (d, J=6.0 Hz, 3H); 1.08 (t, J=7.0 Hz, 3H); 1.71 (dd, $J_1$=7.0 Hz, $J_2$32 11.3 Hz, 1H); 2.05 (dd, $J_1$=7.2 Hz, $J_2$=10.8 Hz, 1H); 2.31 (d, J=11.4 Hz, 1H) 2.36–2.57 (m, 2H); 2.69 (dd, $J_1$=2.2 Hz, $J_2$=10.7 Hz, 1H); 2.85 (dd, $J_1$=7.0 Hz, $J_2$=13.9 Hz, 1H); 3.18 (dd, $J_1$=5.3 Hz, $J_2$=13.9 Hz, 1H); 3.84 (q, J=7.0 Hz, 2H); 4.78 (s, 1H); 5.11 (d, J=10.0 Hz, 1H); 5.18 (d, J=16.4 Hz, 1H); 5.65–5.88 (m, 1H); 6.46 (d, J=7.4 Hz, 1H); 6.58 (s,1H); 6.65 (d, J=8.1 Hz, 1H); 7.01–7.27 (m, 9H); 9.33 (s, 1H). Mass spectrum (CI—$CH_4$) m/e: 502 (M+1. 90%), 348 (15%), 153 (100%). $[α]_D^{20}$=+6.15° (abs. ethanol, c=1.0). The monohydrochloride salt may be prepared as in Method A.

EXAMPLE 29

(+)-3-((αR)-α-((2S,5R)-4-Allyl-2.5-dimethyl-1-piperazinyl)-3-hydroxybenzyl)-N-methyl-N-phenethylbenzamide N-Methylphenethylamine was coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-methyl-N-phenethylbenzamide as a light yellow powder. NMR (300 MHz, DMSO-$d_6$, 80° C.): δ0.91 (d, J=5.5 Hz, 3H); 1.08 (d, J=6.3 Hz, 3H); 1.87 (dd, $J_1$=7.1 Hz, $J_2$=11.2 Hz, 1H); 2.09 (dd, $J_1$=7.1 Hz, $J_2$=11.0 Hz, 1H); 2.58 (d, J=11.3 Hz, 1H); 2.67 (m, 1H); 2.76 (dd, $J_1$=6.2 Hz, $J_2$=13.2 Hz, 1H); 2.77–2.87 (m, 4H); 2.89 (s, 3H); 3.18 (dd, $J_1$=5.5 Hz, $J_2$=14.2 Hz, 1H); 3.55 (br s, 2H); 4.97 (s, 1H); 5.10 (d, J=10.2 Hz, 1H); 5.16 (d, J=17.3Hz, 1H); 5.74–5.89 (m, 1H); 6.65–6.13 (m, 3H); 7.07–7.41 (m, 9H); 7.43 (d, J=7.9 Hz, 1H); 9.07 (s,1H). Mass spectrum (CI—$CH_4$) m/e: 498 (M+1, 88%), 344 (22%), 153 (100%. $[α]_D^{20}$=+3.8° )ethanol, c=1.25). The free amine (0.232 g) was dissolved in ethanol and titrated with ethanolic hydrogen chloride to pH 3.9 followed by precipitation with diethyl ether from dichloromethane to give 0.205 g of the monohydrochloride salt as a hygroscopic light yellow powder. Calc. for $C_{32}H_{39}N_3O_2$ HCl $H_2O$: C, 69.61; H, 7.67; N, 7.61: Cl, 6.42. Found: C, 69.51: H, 7.73; N, 7.47: Cl, 6.52.

EXAMPLE 30

(+)-3-((αR)-α-((2S,5R)-4-Allyl-2.5-dimethyl-1-piperazinyl)-3-hydroxybenzyl)-N-(4-methoxyphenyl)-N-methylbenzamide 4-Methoxy-N-methylaniline was coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give 3-((αR)-α-((2S,5R)-4-allyl-2,5-dimethyl-1-piperazinyl)-3- hydroxybenzyl)-N-(4-methoxyphenyl)-N-methylbenzamide as a light purple powder. NMR (200 MHz. DMSO-$d_6$): δ0.89 (d, J=6.0 Hz, 3H); 0.96 (d, J=6.1 Hz, 3H); 1.66 (dd, $J_1$=6.5 Hz $J_2$=11.0 Hz, 1H); 200 (dd, $J_1$=7.1 Hz, $J_2$=10.4 Hz, 1H); 2.27 (br d, J=11.4 Hz, 1H); 2.36–2.54 (m, 2H); 2.64 (d, J=11.6 Hz, 1H); 2.82 (dd, $J_1$=6.9 Hz, $J_2$=13.6 Hz, 1H); 3.18 (dd, $J_1$=5.4 Hz, $J_2$=12.8 Hz, 1H); 3.30 (s, 3H); 3.68 (s, 3H); 4.76 (s, 1H); 5.11 (d, J=10.6 Hz, 1H); 5.18 (d, J=17.1 Hz, 1H); 5.66–5.88 (m, 1H); 6.42 (d, J=7.1 Hz, 1H); 6.58 (s, 1H); 6.63 (d, J=7.4 Hz, 1H); 6.78 (d, J=8.8 Hz, 2H); 6.97–7.24 (m, 7H); 9.34 (s, 1H). Mass spectrum (CI—$CH_4$)m/e: 500 (M+1. 79%), 346 (49%), 153 (100%). $[α]_D^{20}$=+9.6° (abs. ethanol, c=1.0). The free amine was dissolved in ethanol and titrated with ethanolic hydrogen chloride to pH 4.0 followed by precipitation with diethyl ether from dichloromethane to give the monohydrochloride salt as a hygroscopic light purple powder. Calc. for $C_{31}H_{37}N_3O_3$ HCl $H_2O$: C, 67.19; H, 7.28; N, 7.58; Cl, 6.40. Found: C, 67.01; H, 7.30; N, 7.53; Cl, 6.42.

EXAMPLE 31

(+)-3-((αR)-α-((2S,5R)-4-Allyl-2,5-dimethyl-1-piperazinyl)-3-hydroxybenzyl)-N-(2-fluorophenyl)-N-methylbenzamide 2-Fluoro-N-methylaniline [NMR (200 MHz, DMSO-$d_6$): δ2.89 (s, 3H); 3.87 (br s, 1H); 6.59–6.78 (m, 2H); 6.91–7.10 (m, 2H)] was prepared from 2-fluoroaniline, coupled with 3-((αR)-α-((2S, 5R)-4-allyl-2,5-dimethyl-1-piperazinyl)-3-(tert-butyldimethylsilyloxy)benzyl)benzoyl chloride, deprotected and purified by the methods described in Example 10 to give 3-((αR)-α-((2S,5R)-4-allyl-2,5-dimethyl-1-piperazinyl)-3-hydroxybenzyl)-N-(2-fluorophenyl)-N-methylbenzamide as an off-white powder. NMR (200 MHz, DMSO-$d_6$): δ0.92 (d, J=6.1 Hz, 3H); 0.99 (d, J=6.1 Hz, 3H); 1.69 (dd, $J_1$=6.7 Hz, $J_2$=10.8 Hz, 1H); 2.05 (dd, $J_1$=7.6 Hz, $J_2$=11.1 Hz, 1H); 2.30 (br d, J=11.5 Hz, 1H); 2.41– 2.52 (m, 2H); 2.68 (br d, J=10.4 Hz, 1H); 2.83 (dd, $J_1$=7.2 Hz, $J_2$=13.8 Hz, 1H); 3.20 (dd, $J_1$=6.1 Hz, $J_2$=14.2 Hz, 1H); 3.30 (s, 3H); 4.82 (s, 1H); 5.12 (d, J=9.7 Hz, 1H); 5.18 (d, J=15.8 Hz, 1H); 5.72–5.86 (m, 1H); 6.45 (d, J=7.4 Hz, 1H); 6.56 (s, 1H); 6.66 (d, J=8.0 Hz, 1H); 7.05–7.38 (m, 9H); 9.33 (s, 1H). Mass spectrum (CI—$CH_4$) m/e: 488 (M+1, 100%), 334 (45%), 153 (86%). $[α]_D^{20}$=+2.02° (abs. ethanol, c=1.1). The free amine was dissolved in ethanol and titrated with ethanolic hydrogen chloride to pH 4.0 followed by precipitation with diethyl ether from dichloromethane to give the monohydrochloride salt as a hygroscopic beige powder. Calc. for $C_{30}H_{34}N_3O_2F$ HCl 0.75 $H_2O$: C, 67.03; H, 6.84; N, 7.82; Cl, 6.59. Found: C, 67.05; H, 6.86; N, 7.77; Cl, 6.67.

EXAMPLE 32

(+)-3-((αR)-α-((2S,5R)-4-Allyl-2,5-dimethyl-1-piperazinyl)-3-hydroxybenzyl)-N-allyl-N-phenylbenzamide N-Allylaniline [NMR (200 MHz, DMSO-$d_6$): δ3.68 (t, J=5.2 Hz, 2H); 5.10 (d, J=10.2 Hz, 1H); 5.23 (d, J=17.2 Hz, 1H); 5.78 (br s, 1H); 5.75–5.97 (m, 1H); 6.52 (t, J=7.3 Hz, 2H); 6.56 (d, J=7.8 Hz, 2H); 7.06 (t, J=7.3 Hz, 2H)] was prepared from aniline and allyl bromide via trifluoroacetanilide using the general method described by Hodge (Harland, P.A.; Hodge, P; Maughan, W.; Wildsmith, E. *Synthesis*, 1984, 941).

N-Allylaniline was coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give 3-((αR)-α-((2S,5R)-4-allyl-2,5-dimethyl-1-piperazinyl)-3-hydroxybenzyl)-N-allyl-N-phenylbenzamide as an off-white powder. NMR (200 MHz, DMSO-$d_6$): δ0.91 (d, J=6.3 Hz, 3H); 0.97 (d, J=5.8 Hz, 3H); 1.67 (dd, $J_1$=6.7 Hz, $J_2$=10.6 Hz, 1H); 2.03 (dd, $J_1$=7.0 Hz, $J_2$=10.3 Hz, 1H); 2.29 (d, J=11.9 Hz, 1H); 2.39–2.53 (m, 2H); 2.67 (br d, J=11.2 Hz, 1H); 2.83 (dd, $J_1$=6.8 Hz, $J_2$=14.4 Hz, 1H); 3.17 (dd, $J_1$=5.2 Hz, $J_2$=14.0 Hz, 1H); 4.45 (d, J=5.5 Hz, 2H); 4.78 (s, 1H); 5.11 (d, J=7.4 Hz, 1H); 5.12 (d, J=8.5 Hz, 1H); 5.17 (d, J=11.9 Hz, 1H); 5.18 (d, J=15.3 Hz, 1H); 5.71–5.98 (m, 2H); 6.42 (d, J=7.6 Hz, 1H); 6.56 (s, 1H); 6.65 (d, J=7.8 Hz, 1H); 7.02–7.33 (m, 10H); 9.33 (s, 1H). Mass spectrum (CI—$H_4$) m/e: 496 (M+1, 45%), 342 (22%), 153 (100%). $[α]_D^{20}$=+6.0° (abs. ethanol. c=1.1). The free amine was dissolved in ethanol and titrated with ethanolic hydrogen chloride to pH 3.8 followed by precipitation with diethyl ether from dichloromethane to give the monohydrochloride salt as a hygroscopic off-white powder. Calc. for $C_{32}H_{37}N_3O_2$ HCl $H_2O$: C, 69.86; H, 7.33; N, 7.64; Cl, 6.44. Found: C, 69.94; H, 7.24; N, 7.62; Cl, 6.52.

EXAMPLE 33

(+)-3-((αR)-α-((2S,5R)-4-Allyl-2,5-dimethyl-1-piperazinyl)-3-hydroxybenzyl)-N-(cyclopropyl)methyl-N-phenylbenzamide N-(Cyclopropylmethyl)aniline [NMR (200 MHz, DMSO-$d_6$): δ0.21 (m, 2H); 0.51 (m, 2H); 1.01 (m, 1H); 3.63 (d, J=7.3 Hz, 1H); 3.80 (br s, 1H); 5.78 (br s, 1H); 7.18 (t, J=7.2 Hz, 1H); 7.25 (d, J=7.8 Hz, 2H); 7.42 (t, J=7.3 Hz, 2H)] was prepared from aniline and (bromomethyl)cyclopropane via trifluoroacetanilide using the general method described by Hodge (Harland, P. A.; Hodge, P; Maughan, W.; Wildsmith, E. *Synthesis*, 1984, 941.).

N-(Cyclopropyl)methylaniline was coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give 3-((αR)-α-((2S,5R)-4-allyl-2,5-dimethyl-1-piperazinyl)-3-hydroxybenzyl)-N-(cyclopropyl)methyl-N-phenylbenzamide as an off-white powder. NMR (200 MHz, DMSO-$d_6$): δ0.09 (m, 2H); 0.39 (m, 2H); 0.92 (d, J=6.3 Hz,3H); 0.96 (d, J=6.2 Hz, 3H); 1.28 (m, 1H); 1.69 (dd, $J_1$=7.4 Hz, $J_2$=11.5 Hz, 1H); 2.04 (dd, $J_1$=6.6 Hz, $J_2$=11.0 Hz, 1H); 2.30 (br d, J=12.1 Hz, 1H); 2.40–2.54 (m, 2H); 2.67 (br d, J=9.8 Hz, 1H); 2.85 (dd, $J_1$=7.4 Hz, $J_2$=13.7 Hz, 1H); 3.16 (dd, $J_1$=4.5 Hz, $J_2$=14.7 Hz, 1H); 3.72 (d, J=7.0 Hz, 2H); 4.77 (s, 1H); 5.12 (d, J=10.0 Hz, 1H); 5.18 (d, J=15.6 Hz, 1H); 5.70–5.85 (m, 1H); 6.44 (d, J=7.3 Hz, 1H); 6.57 (s, 1H); 6.65 (d, J=8.0 Hz, 1H); 7.02–7.33 (m, 10H); 9.33 (s, 1H). Mass spectrum (CI—$CH_4$) m/e: 510 (M+1, 61%), 356 (42%), 153 (100%). $[α]_D^{20}$=+8.9° (abs. ethanol, c=1.1). The free amine was dissolved in ethanol and titrated with ethanolic hydrogen chloride to pH 3.75 followed by precipitation with diethyl ether from dichloromethane to give the monohydrochloride salt as a hygroscopic off-white powder. Calc. for $C_{33}H_{39}N_3O_2$ HCl 1.25 $H_2O$: C, 69.70; H, 7.53; N, 7.39; Cl, 6.23. Found: C, 69.82; H, 7.52; N, 7.36; Cl, 6.28.

EXAMPLE 34

3-((αR)-α-((2S,5R)-4-Allyl-2,5-dimethyl-1-piperazinyl)-3-hydroxybenzyl)-N-isopropyl-N-phenylbenzamide N-Isopropylaniline [NMR (200 MHz, DMSO-$d_6$): δ1.13 (d, J=6.3 Hz, 6H); 3.58 (m, 1H); 5.30 (d, J=8.0 Hz, 1H); 6.49 (t, J=7.2 Hz, 1H); 6.55 (d, J=7.8 Hz, 2H); 7.06 (t, J=7.6 Hz, 2H)] was prepared from aniline and acetone via reductive amination using the general method described by Schellenberg (Schellenberg, K. A. *J.Org.Chem.* 1963, 28, 3259).

N-Isopropylaniline was then coupled with 3-((αR)-α-((2S,5R)-4-allyl-2,5-dimethyl-1-piperazinyl)-3-(tert-butyldimethylsilyloxy)-benzyl)benzoyl chloride, deprotected and purified by the methods described in Example 10 to give 3-((αR)-α-((2S,5R)-4-allyl-2,5-dimethyl-1-piperazinyl)-3-hydroxybenzyl)-N-isopropyl-N-phenylbenzamide as an off-white solid. NMR (200 MHz, DMSO-$d_6$): δ0.92 (d, J=6.1 Hz, 3H); 0.99 (d, J=5.9 Hz, 3H); 1.11 (d, J=6.9 Hz, 6H); 1.70 (dd, $J_1$=7.2 Hz, $J_2$=11.1 Hz, 1H); 2.07 (dd, $J_1$=7.6 Hz, $J_2$=10.6 Hz, 1H); 2.33 (br d, J=9.9 Hz, 1H); 2.42–2.54 (m, 2H); 2.68 (br d, J=10.4 Hz, 1H); 2.85 (dd, $J_1$=6.5 Hz, $J_2$=13.9 Hz, 1H); 3.16 (dd, $J_1$=4.9 Hz, $J_2$=14.1 Hz, 1H); 4.75 (s, 1H); 4.85 (m, 1H); 5.10 (d, J=10.2 Hz, 1H); 5.18 (d, J=16.8 Hz, 1H); 5.70–5.84 (m, 1H); 6.50 (d, J=7.1 Hz, 1H); 6.59 (s, 1H); 6.65 (d, J=8.2 Hz, 1H); 7.03–7.32 (m, 10H); 9.33 (s, 1H). Mass spectrum (CI—$CH_4$) m/e: 498 (M+1, 100%), 344 (43%), 153 (76%). $[\alpha]_D^{20}$=+6.4° (abs. ethanol, c=1.4). The free amine was dissolved in ethanol and titrated with ethanolic hydrogen chloride to pH 4.0 followed by precipitation with diethyl ether from dichloromethane to give the monohydrochloride salt as a hygroscopic off-white powder. Calc. for $C_{32}H_{39}N_3O_2$ HCl 0.5 $H_2O$: C, 70.76; H, 7.61; N, 7.74; Cl, 6.53. Found: C, 71.01; H, 7.83; N, 7.49; Cl, 6.41.

EXAMPLE 35

3-((αR)-α-((2S,5R)-4-Allyl-2,5-dimethyl-1-piperazinyl)-3-hydroxybenzyl)-N-cyclopropyl-N-phenylbenzamide N-Cyclopropylaniline was prepared via the Barton approach for arylation of amines (Barton, D. H.; Finet, J-P.; Khamsi. J. *Tetrahedron Lett.* 1987, 28 887). Cyclopropylamine (1.0 g, 17.5 mmol.) was added to triphenylbismuth (9.25 g, 21.0 mmol.) and cupric acetate (1.6 g, 8.75 mmol) in dichloromethane (30 mL) at room temperature under nitrogen. The mixture was stirred for 18 hours, filtered over a short plug of celite to remove any insoluble material, and purified by chromatography on a silica gel column (4 cm×10 cm) using hexane/ethyl acetate (95/5) for elution. The fraction containing the desired product was stripped of all volatiles under vacuum to yield N-cyclopropylaniline (0.8 g). NMR (200 MHz, DMSO-$d_6$): δ0.37 (m, 2H); 0.68 (m, 2H); 2.30 (m, 1H); 6.03 (br s, 1H); 6.56 (t, J=7.4 Hz, 1H); 6.70 (d, J=8.2 Hz, 2H); 7.09 (t, J=7.8 Hz, 2H)

N-Cyclopropylaniline was then be coupled with 3-((αR)-α-((2S,5R)-4-allyl-2,5-dimethyl-1-piperazinyl)-3-(tert-butyldimethylsilyloxy)-benzyl)benzoyl chloride, deprotected and purified by the methods described in Example 10 to give 3-((αR)-α-((2S,5R)-4-allyl-2,5-dimethyl-1-piperazinyl)-3-hydroxybenzyl)-N-cyclopropyl-N-phenylbenzamide as a yellow powder. NMR (200 MHz, DMSO-$d_6$): δ0.44 (m, 2H); 0.70 (m, 2H); 0.93 (d, J=6.1 Hz, 3H); 1.01 (d, J=5.7 Hz, 3H); 1.74 (dd, $J_1$=7.7 Hz, $J_2$=11.8 Hz, 1H); 2.05 (dd, $J_1$=6.8 Hz, $J_2$=11.1 Hz, 1H); 2.39 (br d, J=10.5 Hz, 1H); 2.41–2.54 (m, 2H); 2.69 (br d, J=11.8 Hz, 1H); 2.83 (dd, $J_1$=6.6 Hz, $J_2$=13.6 Hz, 1H); 3.05–3.36 (m, 2H); 4.83 (s, 1H); 5.10 (d, J=9.8 Hz, 1H); 5.17 (d, J=17.4 Hz, 1H); 5.70–5.86 (m, 1H); 6.57 (d, J=7.1 Hz, 1H); 6.63 (s, 1H); 6.65 (d, J=8.2 Hz, 1H); 7.03–7.38 (m, 10H); 9.34 (s, 1H). Mass spectrum (CI—$CH_4$) m/e: 496 (M+1, 100%), 342 (45%), 153 (90%). $[\alpha]_D^{20}$=+7.1° (abs. ethanol, c=1.1). The free amine was dissolved in ethanol and titrated with ethanolic hydrogen chloride to pH 3.95 followed by precipitation with diethyl ether from dichloromethane to give the monohydrochloride salt as a hygroscopic orange powder. Calc. for $C_{32}H_{37}N_3O_2$ HCl 1.50$H_2O$: C, 68.74; H, 7.39; N, 7.51; Cl, 6.34. Found: C, 68.56; H, 7.49; N, 7.26; Cl, 6.37.

EXAMPLE 36

(+)-3-((αR)-α-((2S,5R)-4-Allyl-2,5-dimethyl-1-piperazinyl)-3-hydroxybenzyl)-N-ethyl-N-(3-fluorophenyl)benzamide 3-Fluoro-N-ethylaniline [NMR (DMSO-$d_6$, 200 MHz): δ1.18 (t, J=7.2 Hz, 3H); 3.02 (dq, $J_1$=7.2 Hz, $J_2$=7.2 Hz, 2H); 5.86 (br m, 1H); 6.24–6.42 (m, 3H); 7.07 (q, J=7.8 Hz, 1H)] was prepared from 3-fluoroaniline and acetic anhydride, coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-ethyl-N-(3-fluorophenyl)benzamide as a white solid. NMR (DMSO-$d_6$, 200 MHz): δ0.92 (d, J=6 Hz, 3H); 0.96 (d, J=6 Hz, 3H); 1.05 (t, J=7 Hz, 3H); 1.7 (m, 1H); 2.05 (m, 1H); 2.3 (m, 1H); 2.5 (m, 2H); 2.7 (m, 1H); 2.9 (m, 1H); 3.2 (m, 1H); 3.9 (q, J=7 Hz, 2H); 4.8 (s, 1H); 5.1 (d, J=10 Hz, 1H); 5.2 (d, J=16 Hz, 1H); 5.8 (m, 1H); 6.45 (d, J=8 Hz, 1H); 6.6 (s, 1H); 6.65 (d, J=8 Hz, 1H); 6.9 (d, J=8 Hz, 1H); 7.0–7.2 (m, 3H); 7.2–7.4 (m, 5H); 9.35 (s, 1H). $[\alpha]_D^{20}$=+4.3° (abs EtOH, c=3.9). Calc. for $C_{31}H_{36}FN_3O_2$ HCl 0.5 $H_2O$: C, 68.06; H, 7.00: N, 7.68; Cl, 6.48. Found C, 68.10;H, 7.04; N, 7.63; Cl, 6.42. Mass spectrum (CI—$CH_4$) m/e: 502 (M+1, 39%), 501 (M, 9%), 348 (29%), 153 (100%).

EXAMPLE 37

(+)-3-((αR)-α-((2S,5R)-4-Allyl-2,5-dimethyl-1-piperazinyl)-3-hydroxybenzyl)-N-(2-fluorophenyl)-N-propylbenzamide 2-Fluoro-N-propylaniline [NMR (DMSO-$d_6$, 200 MHz): δ0.93 (t, J=7.4 Hz, 3H); 1.59 (m, 2H); 3.04 (q, 6.5 Hz, 2H); 5.33 (br m, 1H); 6.47–6.58 (m, 1H); 6.70 (t, J=8.1 Hz, 1H); 6.93–7.05 (m, 2H)] was prepared from 2-fluoroaniline and propionic anhydride, coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-(2-fluorophenyl)-N-propylbenzamide as a white solid. NMR (DMSO-$d_6$, 200 MHz): δ0.9–1.05 (m, 9H); 1.5 (m, 2H); 1.7 (m, 1H); 2.05 (m, 1H) 2.3(m, 1H); 2.5 (m, 2H); 2.7 (m, 1H); 2.85 (m, 1H); 3.2 (m, 1H); 3.7 (m, 2H); 4.8 (br s, 1H); 5.1 (d, J=10 Hz, 1H); 5.2 (d, J=16 Hz, 1H); 5.8 (m, 1H); 6.5 (d, J=8 Hz, 1H); 6.6 (s, 1H); 6.65 (d, J=8 Hz, 1H); 7.0–7.4 (m, 9H); 9.3 (s, 1H). $[\alpha]_D^{20}$=+1.8° (abs ethanol, c=2.8). Calc. for $C_{32}H_{38}FN_3O_2$ HCl 0.25 $H_2O$: C, 69.05; H, 7.15; N, 7.55; Cl, 6.37. Found: C, 68.94; H, 7.19; N, 7.57; Cl, 6.41. Mass spectrum (CI—$CH_4$) m/e: 516 (M+1, 93%), 515 (M, 29%), 362 (26%), 153 (100%).

EXAMPLE 38

(+)-3-((αR)-α-((2S,5R)-4-Allyl-2,5-dimethyl-1-piperazinyl)-3-hydroxybenzyl)-N-ethyl-N-(2-fluorophenyl)benzamide 2-Fluoro-N-ethylaniline [NMR (DMSO-$d_6$, 200 MHz): δ1.16 (t, J=7.1 Hz, 3H); 3.11 (dq, $J_1$=7.2 Hz, $J_2$=6.5 Hz, 2H); 6.48–6.59 (m, 1H); 6.70 (t, J=8.5 Hz, 1H); 6.92–7.06 (m, 2H)] was prepared from 2-fluoroaniline and acetic anhydride, coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-allyl-2,5-dimethyl-1-piperazinyl)-3-hydroxybenzyl)-N-ethyl-N-(2-fluorophenyl)benzamide as a light yellow wax. NMR (DMSO-d$_6$, 200 MHz): δ0.9 (d, J=6 Hz, 3H); 0.95 (d, J=6 Hz, 3H); 1.1 (t, J=7 Hz, 3H); 1.7 (m, 1H); 2.1 (m, 1H); 2.3 (m, 1H); 2.5 (m, 2H); 2.7 (m, 1H); 2.85 (m, 1H); 3.8 (br m, 2H); 4.8 (br s, 1H); 5.1 (d, J=10 Hz, 1H); 5.2 (d, J=17 Hz, 1H); 5.8 (m, 1H); 6.45 (m, 1H); 6.5 (s, 1H); 6.65 (m, 1H); 7.0–7.4 (m, 9H); 9.35 (s, 1H). $[\alpha]_D^{20}$=+3.4° (abs ethanol, c,=2:04). Calc. for C$_{31}$H$_{36}$FN$_3$O$_2$ HCl H$_2$O: C, 66.95; H, 7.07; N, 7.56; Cl, 6.38. Found: C, 66.61; H, 7.14; N, 7.53; Cl, 6.40. Mass spectrum (CI—CH$_4$) m/e: 502 (M+1, 89%), 501 (M, 17%), 348 (36%), 153 (100%).

EXAMPLE 39

(+)-3-((αR)-α-((2S,5R)-4-Allyl-2,5-dimethyl-1-piperazinyl)-3-hydroxybenzyl)-N-(3-fluorophenyl)-N-propylbenzamide 3-Fluoro-N-propylaniline [NMR (DMSO-d$_6$, 200 MHz): δ0.96 (t, J=7.3 Hz, 3H); 1.56 (m, 2H); 2.97 (q, 6.9 Hz, 2H); 5.93 (br m, 1H); 6.22–6.43 (m, 3H); 7.06 (q, J=7.8 Hz, 1H)] was prepared from 3-fluoroaniline and propionic anhydride, coupled with 3-((αR)-α-((2S,5R)-4-allyl-2,5-dimethyl-1-piperazinyl)-3-(tert-butyldimethylsilyloxy)benzyl)benzoyl chloride, deprotected and purified by the methods described in Example 10 to give (+)-3-((αR)-α-((2S,5R)-4-Allyl-2,5-dimethyl-1-piperazinyl)-3-hydroxybenzyl)-N-(3-fluorophenyl)-N-propylbenzamide as a light beige solid. NMR (DMSO-d$_6$, 200 MHz): δ0.9–1.05 (m, 9H); 1.5 (m, 2H); 1.7 (m, 1H); 2.05 (m, 1H); 2.3 (m, 1H); 2.5 (m, 2H); 2.7 (m, 1H); 2.85 (m, 1H); 3.8 (m, 2H); 4.8 (s, 1H); 5.1 (d, J=10 Hz, 1H); 5.2 (d, J=16 Hz, 1H); 5.8 (m, 1H); 6.45 (d, J=8 Hz, 1H); 6.6 (s, 1H); 6.7 (d, J=8 Hz, 1H); 6.9 (d, J=8 Hz, 1H); 7.0–7.4 (m, 9H); 9.3 (s, 1H). $[\alpha]_D^{20}$=+4.3° (abs ethanol. c=1.5). Calc. for C$_{32}$H$_{38}$FN$_3$O$_2$ HCl 0.75 H$_2$O: C, 67.95; H, 7.22; N, 7.43; Cl, 6.27. Found: C, 67.72; H, 7.19; N, 7.49; Cl, 6.30. Mass spectrum (CI—CH$_4$) m/e: 516 (M+1, 100%), 515 (M, 22%), 362 (30%), 153 (73%).

EXAMPLES 40–41

The following compounds may be made by forming the appropriately substituted aniline (which is available from the parent aniline and appropriate carboxylic acid anhydride as described in Example 10), coupling with 3-((αR)-α-((2S,5R)-4-allyl-2,5-dimethyl-1-piperazinyl)-3-(tert-butyldimethylsilyloxy)benzyl)benzoyl chloride, deprotecting and purifying by the methods described in Example 10. The monohydrochloride salts may be formed using ethanolic hydrogen chloride as described in Example 10.

3-((αR)-α-((2S,5R)-4-Allyl-2,5-dimethyl-1-piperazinyl)-3-hydroxybenzyl)-N-(4-methoxyphenyl)-N-propylbenzamide 3-((αR)-α-((2S,5R)-4-Allyl-2,5-dimethyl-1-piperazinyl)-3-hydroxybenzyl)-N-ethyl-N-(4-methoxyphenyl)benzamide

EXAMPLE 42

3-((αR)-α-((2S,5R)-4-Allyl-2,5-dimethyl-1-piperazinyl)-3-(N-(3-fluorophenyl)-N-methylcarbamoyl)benzyl)phenyl monophosphate (+)-3-((αR)-α-((2S,5R)-4-allyl-2,5-dimethyl-1-piperazinyl)-3-hydroxybenzyl)-N-(3-fluorophenyl)-N-methylbenzamide (Example 16, 0.75 g 1.54 mmol) was dissolved in dry pyridine (10 mL) under a nitrogen atmosphere. The solution was cooled to −10° C. in an ice and methanol bath. Phosphoryl chloride (0.49 g) was added slowly to the cold solution. The reaction was allowed to stir for 45 minutes, warming gradually, under a nitrogen atmosphere. Water (20 mL) was added to the solution. The solution was stirred for 30 minutes at room temperature. Ammonium hydroxide (15M, 0.85 mL) was added and all volatiles were removed under reduced pressure. The residue was slurried in acetone and filtered. The filtrate was evaporated under reduced pressure to give a quantitative yield of crude product as a light yellow powder. The crude product (0.56 g) was dissolved in 15 mL of water and purified by ion exchange chromatography (12 g, AG 1-x8 Resin, 100–200 mesh, formate form converted to bicarbonate form. Bio-Rad Laboratories, Hercules, Calif.), eluting with water. The desired material eluted in the first fractions. The solvent was concentrated to a small volume under reduced pressure and lyophilized to give 0.39 g of 3-((αR)-α-((2S,5R)-4-allyl-2,5-dimethyl-1-piperazinyl)-3-(N-(3-fluorophenyl)-N-methylcarbamoyl)benzyl)phenyl monophosphate a fluffy white powder (dec. 154°–155° C.). NMR (200 MHz, DMSO-d$_6$): δ1.08 (d, J=5.0 Hz, 3H); 1.17 (d, J=5.2 Hz, 3H); 2.04–2.61 (m, 5H); 2.79–3.16 (m,2H); 3.38 (s, 3H); 3.71 (m,1H); 5.19 (s, 1H); 5.38–5.57 (m, 2H); 5.82–6.03 (m, 1H); 6.39 (d,J= 7.0 Hz, 1H); 6.82–7.39 (m,11H). Mass spectrum (Ion spray)m/e: 1135 (2M+1, 11%), 5.68 (M+1, 100%), 414 (21%). $[\alpha]_D^{20}$=−9.1° (ethanol. c=1.0). Calc. for C$_{30}$H$_{35}$FN$_3$O$_5$P 1.25 H$_2$O 0.25 NH$_3$: C. 60.62 H, 6.49: N. 7.66. Found: C,60.60; H,6.42; N,7.44.

EXAMPLE 43

(+)-3-((αR)-α-((2S,5R)-4-Allyl-2,5-dimethyl-1-piperazinyl)-3-methoxybenzyl)-N-(3-fluorophenyl)-N-methylbenzamide Crude 3-(((2R,5S)-4-allyl-2,5-dimethyl-1-piperazinyl)-3-(1H-benzotriazol-1-yl)methyl-N-(3-fluorophenyl)-N-methylbenzamide was prepared from 2R,5S)-1-allyl-2,5-dimethylpiperazine (1.89 g), benzotriazole (1.39 g), and N-(3-fluorophenyl)-3-formyl-N-methylbenzamide (3.0 g) in toluene as described in Example 16, Method B.

3-Bromoanisole (4.36 g) was dissolved in dry tetrahydrofuran (40 mL), and cooled to −78° C. under nitrogen. n-Butyllithium in hexanes (9.2 mL of a 2.5M solution) was added slowly via syringe to the solution. While stirring for 25 minutes at −78° C., the solution became white and somewhat thick. The solution was transferred via a double-ended needle to a flask containing magnesium bromide etherate (6.02 g) in tetrahydrofuran (60 mL) and stirred for 1 hour at room temperature. The crude 3-(((2R,5S)-4-allyl-2,5-dimethyl-1-piperazinyl)-3-(1H-benzotriazol-1-yl)methyl)-N-(3-fluorophenyl)-N-methylbenzamide in toluene was added to the arylmagnesium bromide reagent just prepared. The solution warmed slightly during the addition and became a cloudy yellow-brown color. After stirring at room temperature for 2.5 hours, 0.5M aqueous hydrochloric acid was added cautiously until the solution reached pH=5. The product was extracted with 100 mL of ethyl acetate and the solvent was removed under vacuum. The residue was taken up in 25 mL of 3N aqueous hydrochloric acid at room temperature. Diethyl ether was added, and the acidic aqueous layer was separated. The aqueous layer was washed a second time with diethyl ether and adjusted to pH=10 using aqueous sodium hydroxide solution. The product was extracted with ethyl acetate. The ethyl acetate portions were combined, washed with dilute sodium hydroxide solution to remove any remaining benzotriazole, washed with saturated sodium chloride solution, dried over sodium sulfate, and evaporated under reduced pressure. The crude product was purified by chromatography on a column of silica gel using 1% ethanol in dichloromethane as the eluant to give 1.71 g of (+)-3-((αR)-α-((2S,5R)-4-allyl-2,5-dimethyl-1-piperazinyl)-3-methoxybenzyl)-N-(3-fluorophenyl)-N-methylbenzamide as a white crystalline solid in greater than 98% isomeric purity (as determined by HPLC, performed on a m-Bondapak C-18 column (125 Å, 3.9×300 mm. Waters Chromatography Division, Millipore Corporation, Milford, Mass.) using 70% methanol and 30% 0.1M aqueous ammonium acetate at a flow rate of 1 mL/min.). NMR (200 MHz, DMSO-d6): δ0.91 (d, J=6.0 Hz, 3H); 1.00 (d,J=6.2 Hz, 3H); 1.69 (dd, $J_1$=7.1 Hz, $J_2$=11.0 Hz, 1H); 2.05 (dd, $J_1$=7.5 Hz, $J_2$=11.0 Hz, 1H); 2.31 (br d, J=9.3 Hz, 1H); 2.42–2.53 (m, 2H); 2.69 (br d, J=11.2 Hz, 1H); 2.85 (dd, $J_1$=7.0 Hz, $J_2$=14.1 Hz, 1H); 3.18 (dd, $J_1$=5.5 Hz, $J_2$=13.5 Hz, 1H); 3.37 (s, 3H); 3.74 (s, 3H); 4.88 (s, 1H); 5.12 (d, J=10.0 Hz, 1H); 5.18 (d, J=15.7 Hz, 1H); 5.70–5.83 (m, 1H); 6.58 (d, J=7.6 Hz, 1H); 6.70 (s, 1H); 6.84 (d, J=8.2 Hz, 1H); 6.94 (t, J=7.8 Hz, 1H); 7.02–7.14 (m, 2H); 7.18–7.34 (m, 6H); 9.31 (s, 1H). Mass spectrum (CI—$CH_4$) m/e: 502 (m+1, 100%), 348 (81%), 153 (12%). $[\alpha]_D^{20}$=+7.73° (abs. ethanol, c=1.1). The free amine was dissolved in ethanol and titrated with ethanolic hydrogen chloride to pH 4.0 followed by precipitation with diethyl ether from dichloromethane to give the monohydrochloride salt as a hygroscopic light yellow powder. Calc. for $C_{31}H_{36}N_3O_2F$ HCl 0.5 $H_2O$: C, 68.06; H, 7.00; N, 7.68; Cl, 6.48. Found: C, 68.13; H, 7.12; N, 7.55; Cl, 6.35.

EXAMPLE 44

(+)-3-((αR)-α-((2S,5R)-4-Allyl-2,5-dimethyl-1-piperazinyl)-3-methoxybenzyl)-N-ethyl-N-(4-flurophenyl)benzamide The compound was prepared from crude 3-(((2R,5S)-allyl-2,5-dimethyl-1-piperazinyl)-3-(1H-benzotriazol-1-yl)-methyl)-N-ethyl-N-(4-fluorophenyl) benzamide (Example 28, Method B, infra) and 3-bromoanisole by methods described in Example 16, Method B. NMR (200 MHz, DMSO-d6): δ0.91 (d, J=6.2 Hz, 3H); 0.99 (d, J=6.3 Hz, 3H); 1.08 (t, J=7.0 Hz, 3H); 1.71 (dd, $J_1$=7.0 Hz, $J_2$=11.1 Hz, 1H); 2.03 (dd, $J_1$=7.1 Hz, $J_2$=10.9 Hz, 1H); 2.31 (d, J=11.2 Hz, 1H); 2.40–2.57 (m, 2H); 2.67 (d, J=11.5 Hz, 1H); 2.84 (dd, $J_1$=6.6 Hz, $J_2$=13.9 Hz, 1H); 3.17 (dd, $J_1$=5.5 Hz, $J_2$=13.9 Hz, 1H); 3.74 (s, 3H); 3.83 (q, J =7.0 Hz, 2H); 4.83 (s, 1H); 5.11 (d, J=10.2 Hz, 1H); 5.18 (d, J=16.4Hz, 1H); 5.63–5.85 (m, 1H); 6.60 (d, J=7.4 Hz, 1H): 6.71 (s, 1 H); 6.84 (d, J=8.2 Hz, 1H); 7.02–7.28 (m, 9 H). Mass spectrum (CI—$CH_4$) m/e: 516 (M+1, 38%), 362 (100%), 153 (16%).

EXAMPLE 45

Selected compounds of the present invention, identified below with reference to the appertaining synthesis Examples hereof, were evaluated for in vitro opioid receptor activity in various receptor systems, including delta receptor agonism in the mouse vas deferens (Mouse Vas Deferens $ED_{50}$), and mu receptor agonism in the guinea pig ileum (Guinea Pig Ileum $ED_{50}$).

The assay procedures used for such determinations of receptor activity are set out below.

In vitro bioassays: Vasa deferentia were removed from mice and suspended between platinum electrodes with 0.5 g of tension in organ bath chambers containing a modified Krebs' buffer of the following composition (millimolar): NaCl, 118; KCl, 4.75; $CaCl_2$, 2.6; $KH_2PO_4$, 1.20; $NaHCO_3$, 24.5; and glucose, 11. The buffer was saturated with 95% $O_2$/5% $CO_2$ and kept at 37° C. Tissues were stimulated at supramaximal voltage with 10 Hz pulse trains for 400 msec.; train interval 10 seconds; and 0.5 msec pulse duration. Intact ileums (about 3 cm length) were removed from guinea pig and suspended with 1 g of tension in a bath chamber as described for the vasa deferentia. The modified Krebs' buffer also contained $MgSO_4$ (1.20 mM). The ileums were stimulated with electrical square-wave pulses of 0.1 Hz, 0.5 msec pulse duration at supramaximal voltage. The percentage inhibition of the electrically induced muscle contractions was determined for the compounds at varying cumulative concentrations. The $ED_{50}$ values were extrapolated from curves showing the dose concentration plotted against the response (J. A. H. Lord, A. A. Waterfield, J. Hughes, H. W. Kosterlitz, Nature 267, 495, (1977)).

Results are shown in Table A below:

TABLE A

| | In Vitro Opioid Receptor Activity[a] | |
|---|---|---|
| Example | Delta-Receptor Mouse Vas Deferens $ED_{50}$(nM) | Mu-Receptor Guinea Pig Ileum $ED_{50}$(nM) |
| 1 | 7.3 (16) | 18 (16) |
| 9 | 0.48 (8) | 1.23 (12) |
| 10 | 0.35 (12) | 0.67 (8) |
| 12 | 0.93 (12) | 1.08 (12) |
| 16 | 0.47 (8) | 3.3 (8) |
| 28 | 0.39 (11) | 4.0 (4) |
| 31 | 0.39 (4) | 4.4 (4) |

[a]Values are the mean of (n) number of experiments.

EXAMPLE 46

Analgesic activity was assessed by the tail pinch assay in rats (male Sprague-Dawley CD strain, weight approximately 300 g) after intravenous (i.v.) tail vein injection. A group of 6 to 8 animals was injected i.v. with compound in sterile 5% dextrose solution at a concentration of 1–5 mg/mL. Five minutes after injection, an artery clamp (Fisher Scientific Co., self-closing artery forcep, catalog #08-905) was placed on the tail about one inch from the tip of the tail to induce pressure nociception for a short duration (maximum of 20 seconds). The nociceptive response was judged by any sign of discomfort, such as running, squeaking, or turning around to bite the clamp. The dose-response curve was plotted for each compound. The analgesic potency (half-maximum effective dose, $ED_{50}$) was determined by the dose at which half of the animals do not show any nociceptive response to the artery clamp pressure within 20 seconds. Antinociceptive $ED_{50}$ doses were 0.35, 0.03, 0.04, and 0.03 mg/kg for the compounds of Examples 1, 16, 27, and 28, respectively.

Pharmaceutical Formulations

In the following formulation Examples, the "Active Ingredient" may be any compound of the invention, such as a compound of formulae (I) and (II).

EXAMPLE 47

Tablet Formulations

The following formulations A, B and C are prepared by wet granulation of the ingredients with a solution of povidone, followed by addition of the magnesium stearate and compression.

|  | meltablet | mg/tablet |
| --- | --- | --- |
| Formulation A | | |
| (a) Active Ingredient | 100 | 100 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 350 | 150 |
| Formulation B | | |
| (a) Active Ingredient | 100 | 100 |
| (b) Lactose | 150 | — |
| (c) Avicel PH 101 | 60 | 26 |
| (d) Povidone B.P. | 15 | 9 |
| (e) Sodium Starch Glycollate | 0 | 12 |
| (f) Magnesium Stearate | 5 | 3 |
| | 350 | 150 |
| Formulation C | | |
| Active Ingredient | 100 | |
| Lactose | 200 | |
| Starch | 50 | |
| Povidone | 5 | |
| Magnesium stearate | 4 | |
| | 359 | |

The following formulations, D and E, are prepared by direct compression of the admixed ingredients.

|  | mg/tablet |
| --- | --- |
| Formulation D | |
| Active ingredient | 100 |
| Pregelatinised Starch NF15 | 50 |
| | 150 |
| Formulation E | |
| Active ingrrdient | 100 |
| Lactose | 150 |
| Avicel | 100 |
| | 350 |
| Formulation F (Controlled Release Formulation) | |
| The formulation is prepared by wet granulation of the following ingredients with a solution of povidone followed by addition of the magnesium stearate and compression. | |
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 500 |

Drug release takes place over a period of about 6–8 hours and is complete after 12 hours.

EXAMPLE 48

Capsule Formulations

Formulation A

A capsule formulation is prepared by admixing the ingredients of Formulations D in Example 62 above and filling into two-part hard gelatin capsules.

| Formulation B | mg/capsule |
| --- | --- |
| (a) Active Ingredient | 100 |
| (b) Lactose B.P. | 143 |
| (c) Sodium Starch Glycollate | 25 |
| (d) Magnesium Stearate | 2 |
| | 270 |

Capsules are prepared by admixing the above ingredients and filling into two-part hard gelatin capsules.

| Formulation C | mg/capsule |
| --- | --- |
| (a) Active Ingredient | 100 |
| (b) Macrogel 4000 BP | 350 |
| | 450 |

Capsules are prepared by melting the Macrogel 4000 BP, dispersing the active ingredient in the melt and filling the melt into two-part hard gelatin capsules.

| Formulation D | mg/capsule |
| --- | --- |
| Active Ingredient | 100 |
| Lecithin | 100 |
| Arachis Oil | 100 |
| | 300 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extrudate and drying. The dried pellets are then coated with the release-controlling membrane (d) and filled into two-piece, hard gelatin capsules.

|  | mg/capsule |
| --- | --- |
| (a) Active Ingredient | 250 |
| (b) Microcrystalline Cellulose | 125 |
| (c) Lactose BP | 125 |
| (d) Ethyl Cellulose | 13 |
| | 513 |

EXAMPLE 49

Injectable Formulation

| Formulation A | |
| --- | --- |
| Active Ingredient | 5.0 mg |
| Hydrochloric acid solution. 0.1M | q.s. to pH 4.0 to 7.0 |
| Sodium hydroxide solution. 0.1M | q.s. to pH 4.0 to 7.0 |
| Sterile Water | q.s. to 10 ml |

The active ingredient is dissolved in most of the water (35°–40° C.) and the pH adjusted to between 4.0 and 7.0 using the hydrochloric acid or the sodium hydroxide as appropriate. The batch is then made up to volume with the water and filtered through a sterile micropore filter into a sterile amber glass vial 10 ml and sealed with sterile closures and overseals.

| Formulation B | |
|---|---|
| Active Ingredient | 12.5 mg |
| Sterile, pyrogen-free. pH 7 phosphate buffer | q.s. to 25 ml |

EXAMPLE 50

| Intramuscular injection | |
|---|---|
| Active Ingredient | 4.0 mg |
| Benzyl Alcohol | 0.10 g |
| Glycofural 75 | 1.45 g |
| Water for Injection | q.s. to 4.00 ml |

The active ingredient is dissolved in the glycofural. The benzyl alcohol is then added and dissolved, and water added to 4 ml. The resulting mixture is filtered through a sterile micropore filter and sealed in sterile amber glass vials.

EXAMPLE 51

| Syrup | |
|---|---|
| Active Ingredient | 0.025 g |
| Sorbitol Solution | 0.10 g |
| Glycerol | 2.00 g |
| Sodium Benzoate | 0.005 2 |
| Flavour. Peach 17.42.3169 | 0.0125 ml |
| Purified Water | q.s. to 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

EXAMPLE 52

| Suppository | mg/suppository |
|---|---|
| Active Ingredient | 30 |
| Hard Fat, BP (Witepsol H15 - | 1970 |
| Dynamit Nobel) | 2000 |

One-fifth of the Witepsol H15 is melted in a steam-jacketed pan at 45° C. maxiumum. The active ingredient is sifted through a 200 mm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogeneous mix. The entire suspension is passed through a 250 mm stainless steel screen and, with continuous stirring, is allowed to cool to 40° C. At a temperature of 38° C. to 40° C., 2.0 g of the mixture is filled into suitable, 2 ml plastic molds. The suppositories are allowed to cool to room temperature.

EXAMPLE 53

Set out below is an illustrative formulation for pessaries comprising at least one of the diarylmethyl piperazine compounds of the present invention.

| Pessaries | mg/pessary |
|---|---|
| Active Ingredient | 30 |
| Anhydrate Dextrose | 490 |
| Potato Starch | 473 |
| Magnesium Stearate | 7 |
| | 1000 |

The above ingredients are mixed directly and pessaries prepared by direct compression of the resulting mixture.

EXAMPLE 54

Set out below are additional illustrative formulations in which the compounds of the invention may be usefully employed, including formulations in the dosage forms of oral suspensions, injectable suspensions, nebulization suspensions, aerosol formulations, powder inhalation formulations, and nasal drops.

| Tablet | |
|---|---|
| Compound of formula (I) | 25.0 mg |
| Lactose BP | 48.5 mg |
| Microcrystalline Cellulose BP ("Avicel pH 101") | 10.0 mg |
| Low-substituted Hydroxypropyl Cellulose BP ("LHPC LH-11") | 10 mg |
| Sodium Starch Glycollate BP ("Explotab") | 3 mg |
| Povidone BP ("K30") | 3.0 mg |
| Magnesium Stearate BP | 0.5 mg |
| | 100.0 mg |
| Oral Suspension | |
| Compound of formula (I) | 50 mg |
| Avicel RC 591 | 75 mg |
| Sucrose syrup | 3.5 ml |
| Methylhydroxybenzoate | 5 mg |
| Color | 0.01% w/v |
| Cherry flavor | 0.1% v/v |
| Tween 80 | 0.2% v/v |
| Water | to 5 ml |
| Injectable suspension | |
| Compound of formula (I) | 1.5 mg |
| Polyvinvl pyrrolidone (PVP) | 170 mg |
| Tween 80 | 0.2% v/v |
| Methylhydroxybenzoate | 0.1% w/v |
| Water for injection | to 3 ml |
| Capsule formulation | |
| Compound of formula (1) | 1.5 mg |
| Starch 1500 | 150 mg |
| Magnesium stearate | 2.5 mg |

Fill the above-described formulation into a hard gelatin capsule.

| Suspension for Nebulization | |
|---|---|
| Compound of formula (I), sterile | 1.0 mg |
| Water for injection | to 10.0 ml |

Disperse the compound of formula (I) in the water for injection, as previously sterilized in a sterile container. Fill into sterile glass ampoules, 10 ml/ampoule under sterile conditions, and seal each ampoule by fusion of the glass.

| Aerosol Formulation | |
|---|---|
| Compound of formula (I), micronized | 1.0 mg |
| Aerosol propellant | to 5.0 ml |

Suspend the micronized compound of formula (I) in the aerosol propellant. Fill this suspension into preformed aerosol cannisters, 5 ml/cannister under pressure, through the valve orifice.

| Powder Inhalation | |
|---|---|
| Compound of formula (I), micronized | 1.0 mg |
| Lactose | 29.0 mg |

Triturate and blend the micronized compound of formula (I) with the lactose. Fill the resulting powder blend into hard gelatin capsule shells, 30 mg per capsule.

| Nasal Drops | |
|---|---|
| Compound of formula (I) | 20.0 mg |
| Methylhydroxybenzoate | 10.0 mg |
| Water for Injection | to 10.0 ml |

Disperse the compound of formula (I) and the methylhydroxybenzoate in the water for injection. Fill this suspension into suitable dropper bottles, 10 ml/bottle and close by securing the dropper bottle and bottle cap.

EXAMPLE 55

The following formulation may be used for microinfusion applications of formulations containing at least one compound of the invention as an active ingredient component.

| Microinfusable formulation | |
|---|---|
| Active ingredient | 10 mg |
| Sodium Chloride | 16 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 20 ml |

The active ingredient and sodium chloride are dissolved in most of the water (35°–40° C.) and the pH is adjusted to between 4.0 and 7.0 using the hydrochloric acid or the sodium hydroxide as appropriate. The bath then is made up to volume with the water and filtered through a sterile micropore filter into a sterile amber glass vial 20 ml and sealed with sterile closure and overseals.

EXAMPLE 56

Transdermal Administration

Compositions comprising compounds of formula (I) as an active ingredient may be utilized in transdermal administration devices such as transdermal patches.

The patches bearing or otherwise containing the transdermal formulation are positioned on the body of a wearer in such manner as to remain in contact with the epidermis of the recipient for a prolonged period of time.

Such patches suitably comprise the active compound (1) in an optionally buffered, aqueous solution, (2) dissolved and/or dispersed in an adhesive, or (3) dispersed in a polymer.

A suitable concentration of the active compound is about 1% to about 35%, and preferably from about 3% to about 15%.

By way of example, the active compound may be delivered from the patch by electrotransport or iontophoresis, as generally described in Pharmaceutical Research, 3(6),318 (1986).

EXAMPLE 57

A specific example of a transdermal formulation comprising a compound of the invention as the active ingredient is set out below.

| Transdermal formulation | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with surface area of 10 cm$^2$.

While the invention has been illustratively described herein with respect to various illustrative aspects, features and embodiments, it will be appreciated that numerous variations, modifications and other embodiments are possible in the practice of the present invention, and the invention therefore is to be broadly construed as encompassing all such variations, modifications and other embodiments, within its spirit and scope.

We claim:

1. A method of evaluating receptor or neurotransmitter function in an animal, or cellular or histological sample therefrom, comprising comparatively binding to receptor loci of said animal or sample, a conjugate pair of agonist/antagonist receptor combinant species comprising as one of said species a compound selected from compounds of the formula:

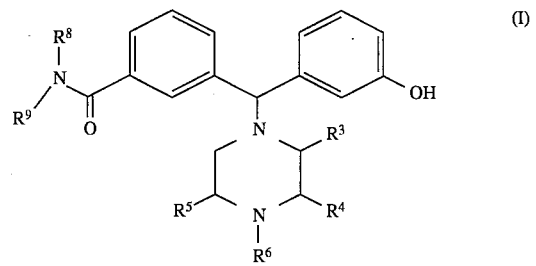

wherein:

$R^8$ and $R^9$ may be the same or different, and may be hydrogen, $C_1$–$C_6$alkyl, $C_3$–$C_6$cycloalkyl, $C_5$–$C_{10}$aryl, or $C_5$–$C_{10}$aryl $C_1$–$C_6$alkyl, or $R^8$ and $R^9$ together may form a ring of 5 or 6 atoms;

$R^3$, $R^4$, $R^5$=hydrogen or methyl, where the total number of methyl groups is one or two; and $R^6$=hydrogen, $C_1$–$C_6$alkyl, $C_2$–$C_6$methoxyalkyl, or $C_3$–$C_6$cycloalkyl, or a pharmaceutically acceptable ether, ester or salt thereof.

2. A method of evaluating receptor or neurotransmitter function in an animal, or cellular or histological sample therefrom, comprising comparatively binding to receptor loci of said animal or sample, a conjugate pair of agonist/antagonist receptor combinant species comprising a compound of formula (II)

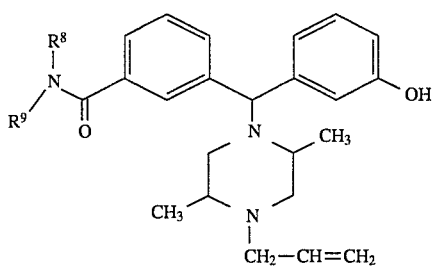

wherein:

R[8] and R[9] may be the same or different, and may be hydrogen, $C_1$–$C_6$alkyl, $C_3$–$C_6$cycloalkyl, $C_5$–$C_{10}$aryl, or R[8] and R[9] together may form a ring of 5 or 6 atoms, or a pharmaceutically acceptable ether, ester or salt thereof.

3. A method of effecting a receptor-mediated therapeutic treatment of an animal in need of such treatment for a condition selected from the group consisting of: mental, emotional, and cognitive disorder; gastrointestinal disorder; alcohol and drug abuse and overdose; cough; emesis; diarrhea; urinary incontinence; lung edema; depression; and respiratory disorders, which comprises administering to said animal an effective amount of a compound selected from compounds of the formula:

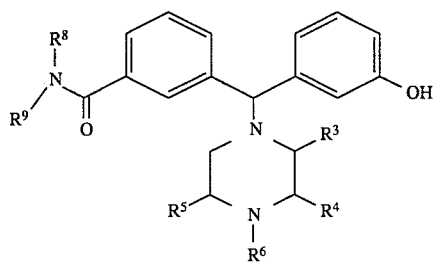

wherein:

R[8] and R[9] may be the same or different, and may be hydrogen, $C_1$–$C_6$alkyl, $C_3$–$C_6$cycloalkyl, $C_5$–$C_{10}$aryl, or $C_5$–$C_{10}$aryl $C_1$–$C_6$alkyl, or R[8] and R[9] together may form a ring of 5 or 6 atoms;

R[3], R[4], R[5]=hydrogen or methyl, where the total number of methyl groups is one or two; and R[6]=hydrogen, $C_1$–$C_6$alkyl, $C_2$–$C_6$methoxyalkyl, or $C_3$–$C_6$cycloalkyl, or a pharmaceutically acceptable ether, ester or salt thereof.

4. A method of effecting a receptor-mediated therapeutic treatment of an animal in need of such treatment, for a condition selected from the group consisting of; mental, emotional, and cognitive disorder; gastrointestinal disorder; alcohol and drug abuse and overdose; cough; emesis; diarrhea; urinary incontinence; lung edema; depression; and respiratory disorders, which comprises administering to said animal an effective amount of a compound of formula (II)

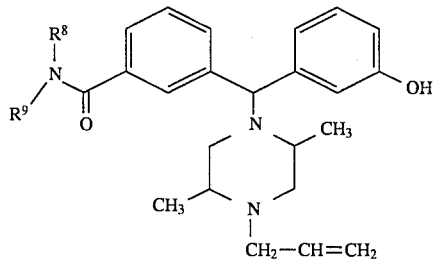

wherein:

R[8] and R[9] may be the same or different, and may be hydrogen, $C_1$–$C_6$alkyl, $C_3$–$C_6$cycloalkyl, $C_5$–$C_{10}$aryl, or R[8] and R[9] together may form a ring of 5 or 6 atoms, or a pharmaceutically acceptable ether, ester or salt thereof.

5. A method according to claim 1 or claim 3, wherein said compound comprises a pharmaceutically acceptable ester or salt of the compound of formula (I).

6. A method according to claim 1 or claim 3, wherein R[6] is $C_1$–$C_6$alkyl or $C_3$–$C_6$cycloalkyl.

7. A method according to claim 1 or claim 3, wherein R[3] and R[5] are both methyl, and R[4] is hydrogen.

8. A method according to claim 1 or claim 3, wherein one of R[8] and R[9] is phenyl, optionally substituted with one or more substituents selected from the group consisting of fluoro, chloro, bromo, iodo, trifluoromethyl and $C_1$–$C_3$alkoxy.

9. A method according to claim 1 or claim 3, wherein phenyl is substituted with one substituent selected from the group consisting of fluoro, chloro, and methoxy.

10. A method according to claim 1 or claim 3, wherein the moiety NR[8]R[9] is selected from the group consisting of:

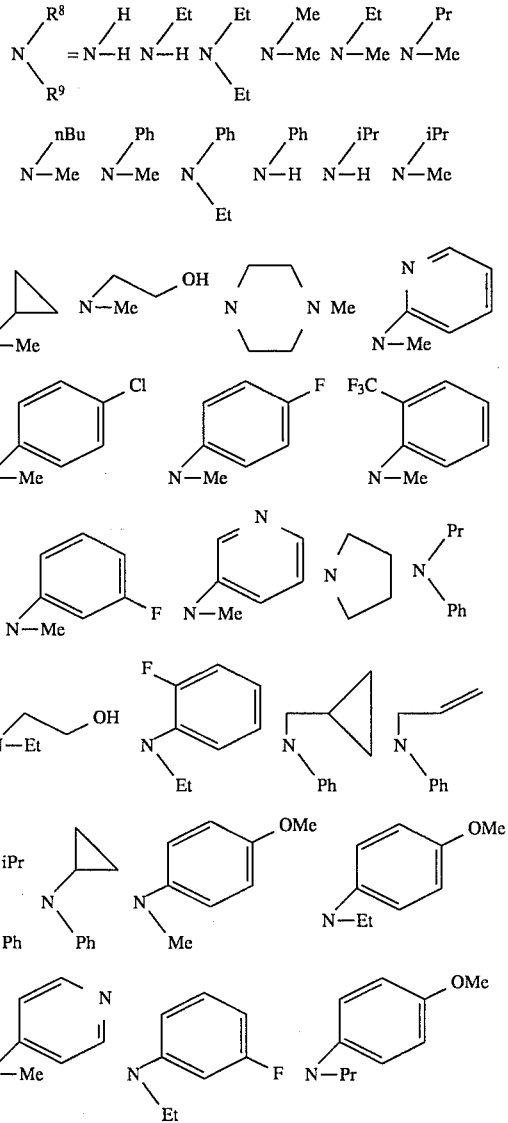

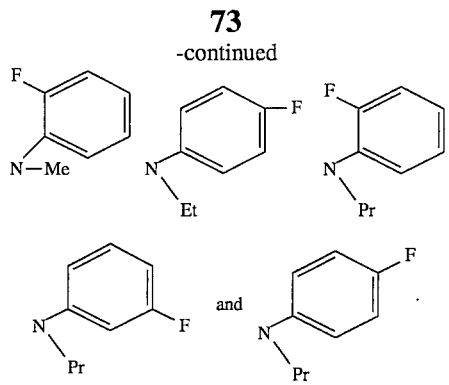

11. A method according to claim 1 or claim 3 wherein $R^6$ is allyl.

12. A method according to claim 2 or claim 4 wherein one of $R^8$ and $R^9$ is phenyl, optionally substituted with one or more substituents selected from the group consisting of fluoro, chloro, bromo, iodo, trifluoromethyl and $C_1$–$C_3$alkoxy.

13. A method according to claim 2 or claim 4 wherein phenyl is substituted with one substituent selected from the group consisting of fluoro, chloro, and methoxy.

14. A method according to claim 2 or claim 4 wherein the moiety $NR^8R^9$ is selected from the group consisting of:

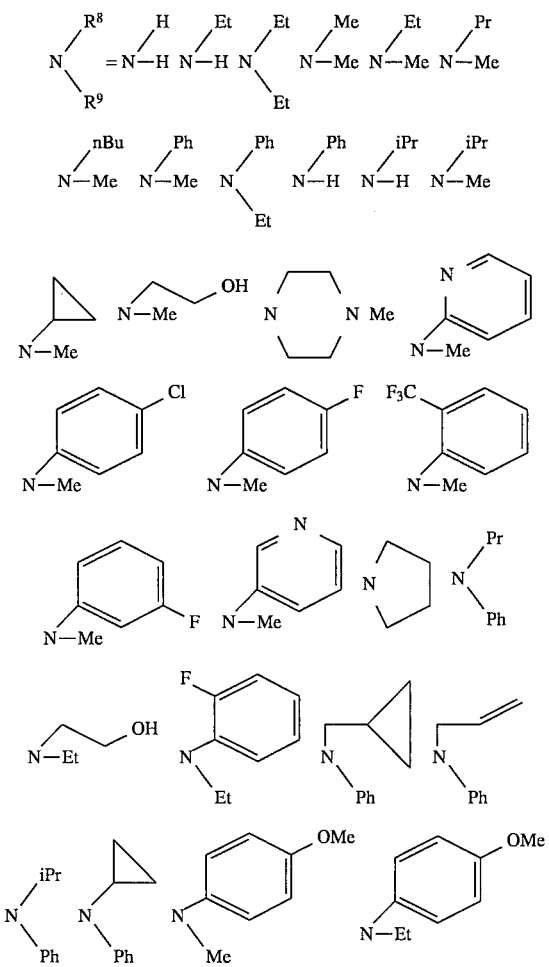

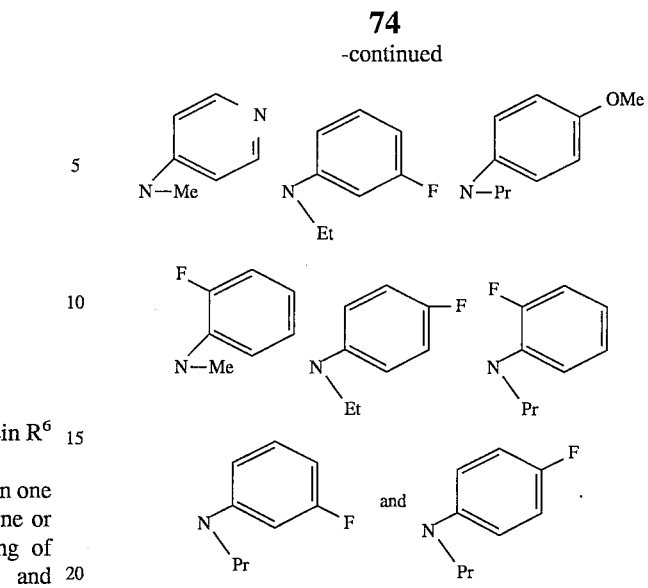

15. A method according to claim 2 or claim 4 wherein one of $R^8$ and $R^9$ is phenyl optionally substituted with one or more substituents selected from the group consisting of halogen, $C_1$–$C_3$alkoxy, $C_1$–$C_3$alkyl and trifluoromethyl, and the other of $R^8$ and $R^9$ is hydrogen or saturated $C_1$–$C_6$hydrocarbyl or unsaturated $C_3$–$C_6$hydrocarbyl.

16. A method according to claim 2 or claim 4 wherein said compound is selected from the group consisting of:

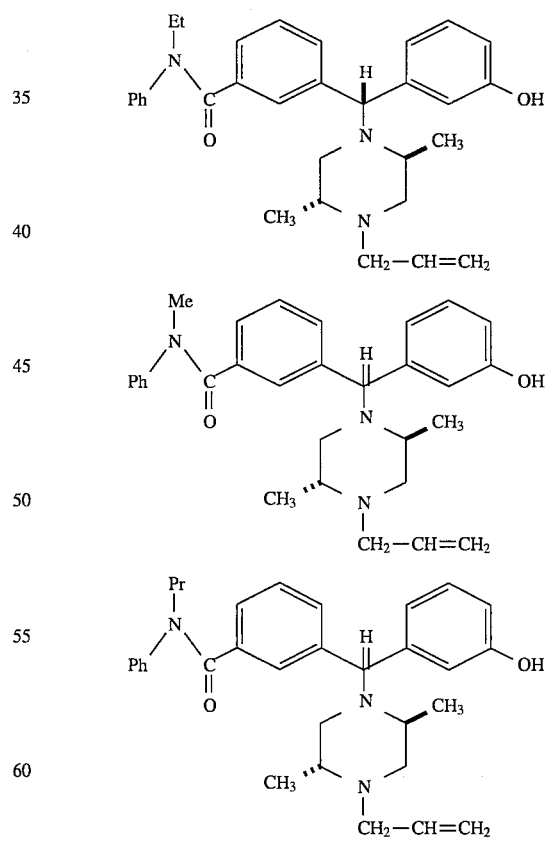

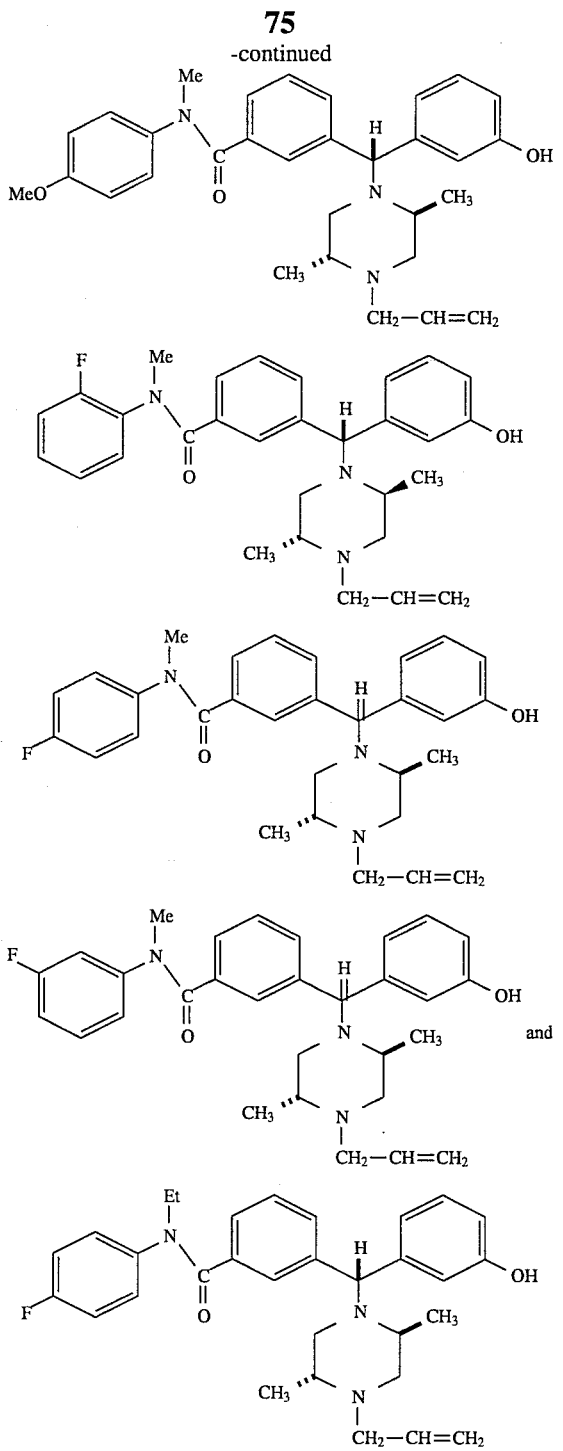

or a pharmaceutically acceptable salt thereof.

17. A method according to claim 2 or claim 4 wherein said compound is selected from those of the group consisting of:

(+)-3-((αR)-α-((2S,5R)-4-Allyl-2,5-dimethyl-1-piperazinyl)-3-hydroxybenzyl)-N-(4-fluorophenyl)-N-methylbenzamide (+)-3-((αR)-α-((2S,5R)-4-Allyl-2,5-dimethyl-1-piperazinyl)-3-hydroxybenzyl)-N-methyl-N-phenylbenzamide (+)-3-((αR)-α-((2S,5R)-4-Allyl-2,5-dimethyl-1-piperazinyl)-3-hydroxybenzyl)-N-(4-chlorophenyl)-N-methylbenzamide (+)-3-((αR)-α-((2S,5R)-4-Allyl-2,5-dimethyl-1-piperazinyl)-3-hydroxybenzyl)-N-ethyl-N-phenylbenzamide (+)-3-((αR)-α-((2S,5R)-4-Allyl-2,5-dimethyl-1-piperazinyl)-3-(((benzyloxy)carbonyl)amino)benzyl)phenol (+)-3-((αR)-α-((2S,5R)-4-Allyl-2,5-dimethyl-1-piperazinyl)-3-hydroxybenzyl)-N-methyl-N-(2-pyridyl)benzamide (−)-3-((αR)-α-((2S,5R)-4-Allyl-2,5-dimethyl-1-piperazinyl)-3-hydroxybenzyl)-N-phenylbenzamide 3-((αR)-α-((2S,5R)-4-Allyl-2,5-dimethyl-1-piperazinyl)-3-hydroxybenzyl)-N-methyl-N-(2-(trifluoromethyl)phenyl)benzamide 3-((αR)-α-((2S,5R)-4-Allyl-2,5-dimethyl-1-piperazinyl)-3-hydroxybenzyl)-N-methyl-N-(2,4,6-trichlorophenyl)-benzamide 3-((αR)-α-((2S,5R)-4-Allyl-2,5-dimethyl-1-piperazinyl)-3-hydroxybenzyl)-N-methyl-N-(4-pyridyl)benzamide 3-((αR)-α-((2S,5R)-4-Allyl-2,5-dimethyl-1-piperazinyl)-3-hydroxybenzyl)-N-methyl-N-(3-pyridyl)benzamide (+)-3-((αR)-α-((2S,5R)-4-Allyl-2,5-dimethyl-1-piperazinyl)-3-hydroxybenzyl)-N-benzyl-N-methylbenzamide (±)-cis-3-(α-(4-Allyl-3,5-dimethyl-1-piperazinyl)-3-hydroxybenzyl)-N,N-diethylbenzamide 3-((αR or αS)-α-((2S,5S)-4-Allyl-2,5-dimethyl-1-piperazinyl)-3-hydroxybenzyl)-N,N-diethylbenzamide 3-((αR or αS)-α-((2R,5R)-4-Allyl-2,5-dimethyl-1-piperazinyl)-3-hydroxybenzyl)-N,N-diethylbenzamide (+)-3-((αR)-α-((2S,5R)-4-Allyl-2,5-dimethyl-1-piperazinyl)-3-hydroxybenzyl)-N-methyl-N-phenethylbenzamide 3-((αR)-α-((2S,5R)-4-Allyl-2,5-dimethyl-1-piperazinyl)-3-hydroxybenzyl)-N-isopropyl-N-methylbenzamide (+)-3-((αR)-α-((2S,5R)-4-Allyl-2,5-dimethyl-1-piperazinyl)-3-hydroxybenzyl)-N-(3-fluorophenyl)-N-methylbenzamide (+)-3-((αR)-α-((2S,5R)-4-Allyl-2,5-dimethyl-1-piperazinyl)-3-hydroxybenzyl)-N-phenyl-N-propylbenzamide (+)-3-((αR)-α-((2S,5R)-4-Allyl-2,5-dimethyl-1-piperazinyl)-3-hydroxybenzyl)-N-(4-methoxyphenyl)-N-methylbenzamide (+)-3-((αR)-α-((2S,5R)-4-Allyl-2,5-dimethyl-1-piperazinyl)-3-hydroxybenzyl)-N-(2-fluorophenyl)-N-methylbenzamide (+)-3-((αR)-α-((2S,5R)-4-Allyl-2,5-dimethyl-1-piperazinyl)-3-hydroxybenzyl)-N-ethyl-N-(4-fluorophenyl)benzamide (+)-3-((αR)-α-((2S,5R)-4-Allyl-2,5-dimethyl-1-piperazinyl)-3-hydroxybenzyl)-N-allyl-N-phenylbenzamide (+)-3-((αR)-α-((2S,5R)-4-Allyl-2,5-dimethyl-1-piperazinyl)-3-hydroxybenzyl)-N-(cyclopropyl)methyl-N-phenylbenzamide 3-((αR)-α-((2S,5R)-4-Allyl-2,5-dimethyl-1-piperazinyl)-3-hydroxybenzyl)-N-isopropyl-N-phenylbenzamide 3-((αR)-α-((2S,5R)-4-Allyl-2,5-dimethyl-1-piperazinyl)-3-hydroxybenzyl)-N-cyclopropyl-N-phenylbenzamide 3-((αR)-α-((2S,5R)-4-Allyl-2,5-dimethyl-1-piperazinyl)-3-hydroxybenzyl)-N-(3-fluorophenyl)-N-propylbenzamide 3-((αR)-α((2S,5R)-4-Allyl-2,5-dimethyl-1-piperazinyl)-3-hydroxybenzyl)-N-ethyl-N-(3-fluorophenyl)benzamide 3-((αR)-α-((2S,5R)-4-Allyl-2,5-dimethyl-1-piperazinyl)-3-hydroxybenzyl)-N-(2-fluorophenyl)-N-propylbenzamide 3-((αR)-α-((2S,5R)-4-Allyl-2,5-dimethyl-1-piperazinyl)-3-hydroxybenzyl)-N-ethyl-N-(2-fluorophenyl)benzamide 3-((αR)-α-((2S,5R)-4-Allyl-2,5-dimethyl-1-piperazinyl)-3-hydroxybenzyl)-N-(4-methoxyphenyl)-N-propylbenzamide 3-((αR)-α-((2S,5R)-4-Allyl-2,5-dimethyl-1-piperazinyl)-3-hydroxybenzyl)-N-ethyl-N-(4-methoxyphenyl)benzamide (+)-3-((αS)-α-((2S,5R)-4-Allyl-2,5-dimethyl-1-piperazinyl)-3-hydroxybenzyl)-N-methyl-N-phenylbenzamide (+)-3-((αR)-((2S,5R)-4-Allyl-2,5-dimethyl-1-piperazinyl)-3-methoxybenzyl)-N-(3-fluorophenyl)-N-methylbenzamide and (+)-3-((αR)-((2S,5R)-4-Allyl-2,5-dimethyl-1-piperazinyl)-3-methoxybenzyl)-N-ethyl-N-(4-fluorophenyl)benzamide, or a pharmaceutically acceptable salt thereof.

18. A method according to claim 2 or claim 4 wherein said compound is of the formula:

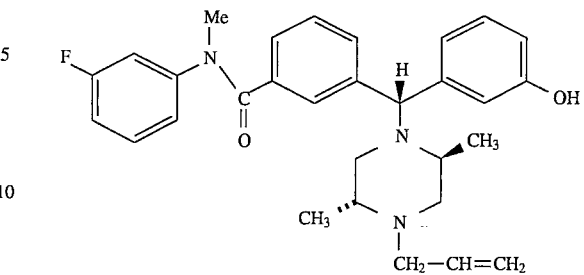

or a pharmaceutically acceptable salt thereof.

19. A method according to claim 2 or claim 4 wherein said compound is (+)-3-((αR)-α-((2S,5R)-4-Allyl-2,5-dimethyl-1-piperazinyl)-3-hydroxybenzyl)-N-(3-fluorophenyl)-N-methylbenzamide.

20. A method according to claim 2 or claim 4 wherein said compound is a pharmaceutically acceptable salt of (+)-3-((αR)-α-((2S,5R)-4-Allyl-2,5-dimethyl-1-piperazinyl)-3-hydroxybenzyl)-N-(3-fluorophenyl)-N-methylbenzamide.

* * * * *

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

Title page (under OTHER PUBLICATIONS):
Column 1, Line 5, "S. N.," should be --S. N. et al.,--

Title page (under OTHER PUBLICATIONS):
Column 1, Line 17 "Disertation" should be --Dissertation--

Title page (under OTHER PUBLICATIONS):
Column 2, Line 40 "Iwanoto, T. et a.," should be --Iwamoto, T. et al.,--

Page 2 (under OTHER PUBLICATIONS):
Column 1, Line 2, "Koper" should be --Korper--

Page 2 (under OTHER PUBLICATIONS):
Column 1, Line 7, "Diphenlpiperazines" should be --Diphenylpiperazines--

Page 2 (under OTHER PUBLICATIONS):
Column 1, Line 17, "N-Monomethylation" should be --n-Monomethylation--

Page 2 (under OTHER PUBLICATIONS):
Column 1, Line 22, "Nonpeptide" should be --Nonpeptidic--

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

Page 2 (under OTHER PUBLICATIONS):
Column 1, Line 27, "Rats" should be --Rat--

Page 2 (under OTHER PUBLICATIONS):
Column 1, Line 27, "Membrane" should be --Membranes--

Page 2 (under OTHER PUBLICATIONS):
Column 2, Line 5, "Agonist" should be --Agonists--

Page 2 (under OTHER PUBLICATIONS):
Column 2, Line 19, ""A General Route to..."" should be --Katritzky, et al., "A General Route to..."--

Page 2 (under OTHER PUBLICATIONS):
Column 2, Line 21, ""The Synthesis..."" should be --Schellenberg, K., "The Synthesis..."--

Page 2 (under OTHER PUBLICATIONS):
Column 2, Line 24, ""Diasstereoselektive..."" should be --Von Dieter Sebach, et al.,"Diastereoselektive...""--

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

Page 2 (under OTHER PUBLICATIONS):
Column 2, Line 25, "vol." should be --Vol.--

Page 2 (under OTHER PUBLICATIONS):
Column 2, Line 27, ""Copper..."" should be --Barton, et al.,"Copper..."--

Page 2 (under OTHER PUBLICATIONS):
Column 2, Line 27, "N-Phenylation" should be --n-Phenylation--

Page 2 (under OTHER PUBLICATIONS):
Column 2, Line 29, "vol." should be --Vol.--

Page 2 (under OTHER PUBLICATIONS):
Column 2, Line 30, ""Organic..."" should be --Jung, et al., "Organic..."--

Page 2 (under OTHER PUBLICATIONS):
Column 2, Line 33, ""Synthesis..."" should be --Harland, et al., "Synthesis..."--

Page 2 (under OTHER PUBLICATIONS):
Column 2, Line 37  "1985" should be deleted

Page 2 (under OTHER PUBLICATIONS):
Column 2, Line 38, "Review:" should be --Tyle, P., Review:--

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

Page 2 (under OTHER PUBLICATIONS):
Column 2, Line 39, "Reserach" should be --Research--

Page 2 (under OTHER PUBLICATIONS):
Column 2, Line 39, "vol." should be --Vol.--

Column 1, Line 42 "(kreceptors." should be --(k) receptors.--

Column 3, Line 38 "$C_5$-$C_{10}$ alkyl," should be --$C_5$-$C_{10}$ aryl$C_1$-$C_6$ alkyl,--

Column 3, Line 64 "amido." should be -amido,--

Column 4, Line 1 "ally" should be --allyl--

Column 6, Line 15

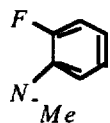 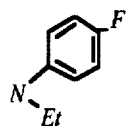 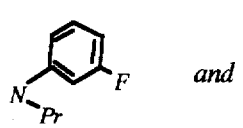

should be

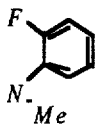 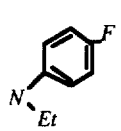 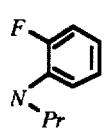 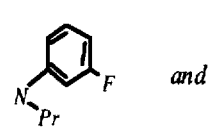

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

Column 10, Line 12    "$CH_2.CH=CH_2$" should be --$CH_2 \cdot CH=CH_2$--

Column 10, Line 22    "$CH_2.CH=CH_2$" should be --$CH_2 \cdot CH=CH_2$--

Column 10, Line 33    "$CH_2.CH=CH_2$" should be --$CH_2 \cdot CH=CH_2$--

Column 10, Line 43"   "$CH_2.CH=CH_2$" should be --$CH_2 \cdot CH=CH_2$--

Column 10, Line 64    "$CH_2.CH=CH_2$" should be --$CH_2 \cdot CH=CH_2$--

Column 11, Line 13    "$CH_2.CH=CH_2$" should be --$CH_2 \cdot CH=CH_2$--

Column 11, Line 23    "$CH_2.CH=CH_2$" should be --$CH_2 \cdot CH=CH_2$--

Column 11, Line 34    "$CH_2.CH=CH_2$" should be --$CH_2 \cdot CH=CH_2$--

Column 13, Line 60    "having conditions(s)" should be --having such condition(s)--

Column 16, Line 19    "hydroxethyl" should be --hydroxyethyl--

Column 20, Line 47    "art, illustrative" should be --art. Illustrative--

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

Column 24, Line 62 "$\xrightarrow{-H_2O}_{H-}$" should be -- $\xrightarrow{-H_2O}_{H+}$ --

Column 28, Line 18 "$SiMe_2 t-Bu$" should be --$OSiMe_2 t-Bu$--

Column 35, Line 50 "5°" should be --100°--

Column 36, Line 53 "acetatepetroleum" should be --acetate-petroleum--

Column 37, Line 21 "$(CI-_4)$" should be --$(CI-CH_4)$--

Column 37, Line 36 "($\alpha$)" should be --(+)--

Column 38, Line 20 "$J_1 13$" should be --$J_1=13$--

Column 38, Line 35 "(+)" should be --($\pm$)--

Column 39, Line 23 "C67.06" should be --C, 67.06--

Column 40, Line 10 "2with" should be --2 with--

Column 40, Line 12 "0.9(d," should be --0.9 (d,--

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

| | |
|---|---|
| Column 40, Line 16 | "2H);" should be deleted |
| Column 40, Line 24 | "2.5dimethyl" should be --2,5-dimethyl-- |
| Column 44, Line 19 | "4.88" should be --488-- |
| Column 44, Line 25 | "$C_{30}H_{34}N_3F$" should be --$C_{30}H_{34}N_3O_2F$-- |
| Column 44, Line 25 | "$H_2O$: 66.47" should be --$H_2O$: C, 66.47-- |
| Column 45, Line 42 | "(d,=5.7 Hz, 3H)" should be --(d,J=5.8 Hz, 3H)-- |
| Column 46, Line 6 | "(1H)" should be --(s, 1H)-- |
| Column 47, Line 10 | "butyldimethylsiloxy)" should be --butyldimethylsilyloxy-- |
| Column 47, Line 15 | "3H)" should be --3H);-- |
| Column 47, Line 18 | "1H" should be --1H);-- |
| Column 47, Line 39 | "125 g)" should be --(125 g)-- |
| Column 47, Line 44 | "filtration. Yielding" should be --filtration, yielding-- |

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

| | |
|---|---|
| Column 47, Line 46 | "(173 g)" should be --(173.9 g)-- |
| Column 50, Line 28 | "(3flurophenyl)" should be --(3-flurophenyl)-- |
| Column 50, Line 33 | "hours." should be --hours,-- |
| Column 50, Line 66 | "(dd, $J_1$=7.6" should be --(dd, $J_1$=7.6 Hz,-- |
| Column 51, Line 6 | "Found: C." should be --Found: C,-- |
| Column 51, Line 13 | "Methyl" should be --methyl-- |
| Column 51, Line 33 | "1.14%" should be --1, 14%-- |
| Column 51, Line 40 | "methyl" should be --Methyl-- |
| Column 52, Line 1 | ")benzoyl" should be --)benzyl)benzoyl-- |
| Column 52, Line 8 | "(s, 1H):" should be --(s, 1H);-- |
| Column 52, Line 64 | "M+1." should be --M+1,-- |
| Column 55, Line 21 | "(80%)," should be --(80%).-- |
| Column 55, Line 55 | "1.90%" should be --1, 90%-- |

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

| | |
|---|---|
| Column 55, Line 56 | "$^{20}$=6.30°" should be --$^{20}$=+6.30°-- |
| Column 56, Line 6 | "1H;" should be --1H);-- |
| Column 56, Line 17 | "3H):" should be --3H);-- |
| Column 56, Line 19 | "$J_2$32 11.3" should be --$J_2$=11.3-- |
| Column 56, Line 26 | "M+1." should be --M+1,-- |
| Column 56, Line 48 | "6.13" should be --6.73-- |
| Column 56, Line 50 | "(100%." should be --(100%).-- |
| Column 56, Line 56 | "7.61:" should be --7.61;-- |
| Column 57, Line 2 | "DMSO-$_6$)" should be --DMSO-d$_6$)-- |
| Column 57, Line 4 | "Hz" should be --Hz,-- |
| Column 57, Line 4 | "200" should be --2.00-- |
| Column 58, Line 11 | "(CI-H$_4$)" should be --(CI-CH$_4$)-- |

UNITED STATES PATENT AND TRADEMARK OFFICE
CERTIFICATE OF CORRECTION

PATENT NO. : 5,552,404
DATED : September 3, 1996
INVENTOR(S) : Kwen-Jen Chang, et al.

It is certified that error appears in the above-indentified patent and that said Letters Patent is hereby corrected as shown below:

Column 60, Line 59   After "(dq. $J_1$=7.2 Hz, $J_2$=6.5 Hz, 2H);" insert --5.30 (br m, 1H);--

Column 60, Line 63   "butyldimethylsilyloxy)benzoyl)" should be -- butyldimethylsilyloxy)benzyl)benzoyl--

Column 62, Line 23   "5.68" should be --568--

Column 65, Line 1    "meltablet" should be --mg/tablet--

Column 65, Line 39   "ingrrdient" should be --ingredient--

Column 69, Line 14   "(I), micronized" should be --(I), 1.0 mg micronized--

Column 76, Line 13   "-benzamide" should be --benzamide--

Column 76, Line 44   "fluorophenyl-" should be --fluorophenyl--

Column 77, Line 20   "fluorophenyl)-" should be --fluorophenyl)--

Signed and Sealed this

Fourth Day of August, 1998

Attest:

BRUCE LEHMAN

Attesting Officer

Commissioner of Patents and Trademarks